(12) United States Patent
Mueller et al.

(10) Patent No.: US 10,059,706 B2
(45) Date of Patent: Aug. 28, 2018

(54) PYRAZOLOPYRIDINE SULFONAMIDES AS NEMATICIDES

(71) Applicant: BAYER CROPSCIENCE AKTIENGESELLSCHAFT, Monheim am Rhein (DE)

(72) Inventors: Klaus-Helmut Mueller, Duesseldorf (DE); Susanne Kuebbeler, Duesseldorf (DE); Joerg Greul, Leverkusen (DE); Daniela Portz, Vettweiss (DE); Olga Malsam, Roesrath (DE); Kerstin Ilg, Cologne (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 2 days.

(21) Appl. No.: 15/309,183

(22) PCT Filed: May 5, 2015

(86) PCT No.: PCT/EP2015/059776
§ 371 (c)(1),
(2) Date: Nov. 6, 2016

(87) PCT Pub. No.: WO2015/169776
PCT Pub. Date: Nov. 12, 2015

(65) Prior Publication Data
US 2017/0088548 A1    Mar. 30, 2017

(30) Foreign Application Priority Data

May 8, 2014   (EP) .................................... 14167534

(51) Int. Cl.
*C07D 471/04*    (2006.01)
*A01N 43/90*    (2006.01)
(52) U.S. Cl.
CPC ........... *C07D 471/04* (2013.01); *A01N 43/90* (2013.01)
(58) Field of Classification Search
None
See application file for complete search history.

(56) References Cited

U.S. PATENT DOCUMENTS

| 8,853,125 B2 | 10/2014 | Gross et al. | |
| 2005/0282842 A1* | 12/2005 | Gudmundsson | C07D 471/04 514/275 |
| 2008/0051409 A1* | 2/2008 | Gmeiner | C07D 471/04 514/252.02 |

FOREIGN PATENT DOCUMENTS

| EP | 0 244 166 A2 | 11/1987 | |
| EP | 2 090 576 A1 | 8/2009 | |
| WO | 2006/015737 A1 | 2/2006 | |
| WO | 2010/034738 A2 | 4/2010 | |
| WO | 2010/129500 A2 | 11/2010 | |
| WO | WO 2011050284 A1 * | 4/2011 | ........... A61K 31/497 |
| WO | 2012/054233 A1 | 4/2012 | |
| WO | 2013/055584 A1 | 4/2013 | |
| WO | WO 2013088256 A1 * | 6/2013 | ........... A61K 31/437 |

OTHER PUBLICATIONS

International Search Report dated Jun. 16, 2015, issued in PCT/EP2015/059776.
CAPLUS Accession No. 1464, "FILE CAPLUS", accessed Sep. 5, 2014, C:\EPODATA\SEA\EPLOGF\sa511320.log.

* cited by examiner

*Primary Examiner* — Mina Haghighatian
*Assistant Examiner* — Erin E Hirt
(74) *Attorney, Agent, or Firm* — McBee Moore Woodward & Vanik IP, LLC

(57) ABSTRACT

Disclosed are compounds of formula (I) which possess nematicidal properties wherein the structural elements have the meaning as indicated in the description.

25 Claims, 3 Drawing Sheets

H-NMR spectrum of N-amino-3-chloro-5-trifluoromethyl-pyridinium p-tosylate ([D$_6$]-DMSO, 400 MHz)

H-NMR spectrum of dimethyl 4-chloro-6-(trifluoromethyl)pyrazolo[1,5-a]pyridine-2,3-dicarboxylate (CDCl₃, 400 MHz)

H-NMR spectrum of 4-chloro-6-(trifluoromethyl)pyrazolo[1,5-a]pyridine-2-carboxylic acid
(II-1) ([D₆]-DMSO, 400 MHz)

PYRAZOLOPYRIDINE SULFONAMIDES AS NEMATICIDES

CROSS REFERENCE TO RELATED APPLICATIONS

This application is a § 371 National Stage Application of PCT/EP2015/059776 filed 5 May 2015, which claims priority to EP 14167534.8, filed May 8, 2014.

BACKGROUND

Field of the Invention

The present invention relates to pyrazolopyridine sulfonamides, their use for the control of animal pests, especially nematodes, in agricultures, formulations containing such compounds and methods for the control of animal pests, especially nematodes. This invention relates to certain sulfonamides, their N-oxides, salts and formulations suitable for agronomic and nonagronomic uses, and methods of their use for controlling animal pests, especially nematodes, in both agronomic and nonagronomic environments. The present invention further relates to processes and intermediate compounds for the preparation of such pyrazolopyridine sulfonamides.

Description of Related Art

Nematodes cause a substantial loss in agricultural product including food and industrial crops and are combated with chemical compounds having nematicidal activity. To be useful in agriculture these compounds should have a high activity, a broad spectrum activity against different strains of nematodes and should not be toxic to non-target organisms. Due to widespread development of resistance to anthelmintic agents in nematode parasites, nematodes continue to cause problems in livestock despite the available chemical therapeutic agents. The need continues for new compounds which are more effective, less costly, less toxic, environmentally safer or have different modes of action.

European Patent Application Publication No. 0 244 166 A2 (referred to as P1) discloses compounds of formula (i) as herbicides

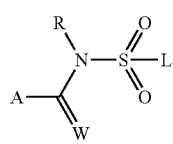

(i)

wherein, inter alia, R is H or an organic substituent, W is O or S, L is an aryl or heteroaryl moiety, and A is selected from a list of bi-, tri- and quadricyclic heterocyclic groups.

PCT patent application publication WO 2010/129500 (P2) discloses compounds of formula (ii) (including all stereoisomers), N-oxides, and salts thereof, and compositions containing them and their use for controlling a parasitic nematode:

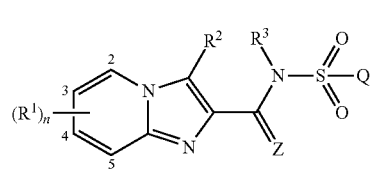

(ii)

wherein, interalia, Z is O or S and Q is phenyl, naphthalenyl, a 5- or 6-membered hetero-aromatic ring or an 8- to 10-membered heteroaromatic bicyclic ring system, each optionally substituted with 1 to 5 substituents.

Anonymously disclosed publication IP com Journal 10, 26 (2010) (P3) describes 10 explicitly listed compounds of general formula (ii) in mixtures with various insecticides in several mixture ratios.

PCT Patent Application Publication WO 2012/054233 (P4) discloses compounds of formula (iii) (including all stereoisomers), N-oxides, and salts thereof, and compositions containing them and their use for controlling a parasitic nematode:

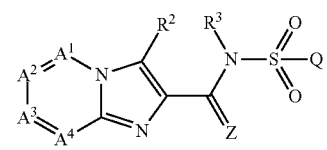

(iii)

wherein, interalia, Z is O or S, Q is phenyl, naphthalenyl, a 5- or 6-membered heteroaromatic ring or an 8- to 10-membered heteroaromatic bicyclic ring system, each optionally substituted with 1 to 5 substituents and $A^1$, $A^2$, $A^3$ and $A^4$ are independently N or $CR^1$, provided that only one of $A^1$, $A^2$, $A^3$ and $A^4$ is N.

PCT Patent Application Publication WO 2013/055584 (P5) discloses solid forms of a certain nematocidal imidazopyridine sulfonamide of formula (ii).

The compounds of the present invention are not disclosed in these publications.

It is an object of the present invention to provide compounds which can be used as nematicides with a satisfactory or improved nematicidal activity, particularly at relatively low application rates, with a high selectivity and high compatibility in crop-plant cultures.

SUMMARY OF THE INVENTION

This invention is directed to compounds of formula (I) (including all stereoisomers), N-oxides, and salts thereof, and formulations containing them and their use for controlling animal pests, especially nematodes, especially parasitic nematodes:

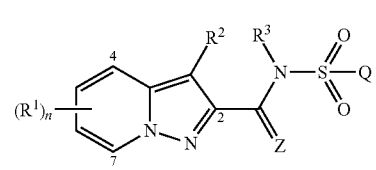

(I)

wherein
  Z is O or S;
  each $R^1$ is independently H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;
  or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;
  or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;
  or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$;
  $R^2$ is H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;
  or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;
  or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;
  or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$, $C_2$-$C_6$-alkoxyalkyl, $OC(O)R^{7a}$ and $N(R^{10})C(O)R^{7a}$;
  $R^3$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;
  or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $OR^{4a}$, and $S(O)_mR^{9a}$;
  or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;
  or $C_1$-$C_6$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;
  or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;
  Q is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C_4$-$C_8$-cycloalkylalkyl, phenyl, naphthalenyl or a 5- or 6-membered heteroaromatic ring or an 8- to 10-membered heteroaromatic bicyclic ring system, each optionally substituted with 1 to 5 substituents independently selected from the group consisting of halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;
  or Q is selected from the group consisting of (U-1) to (U-61), (U-81) to (U-87), (U-89) to (U-103) and (U-105) to (U-123):

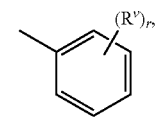

U-1

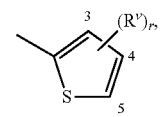

U-2

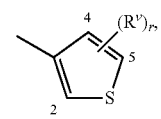

U-3

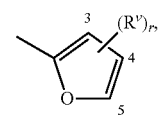

U-4

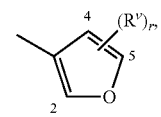

U-5

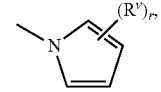

U-6

-continued
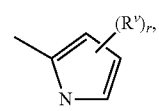 U-7
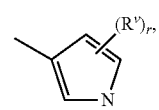 U-8
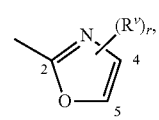 U-9
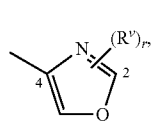 U-10
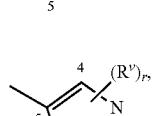 U-11
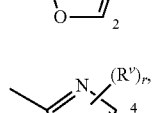 U-12
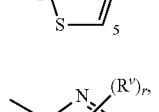 U-13
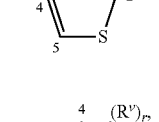 U-14
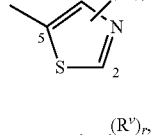 U-15
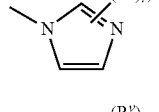 U-16
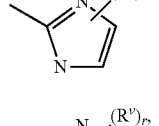 U-17
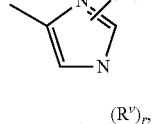 U-18
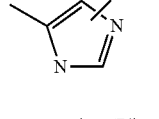 U-19
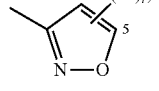
-continued
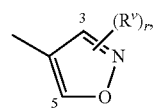 U-20
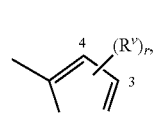 U-21
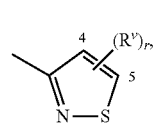 U-22
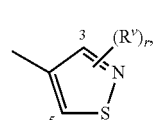 U-23
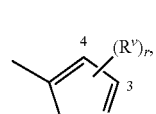 U-24
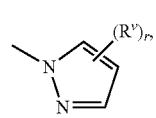 U-25
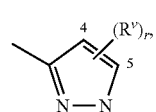 U-26
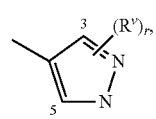 U-27
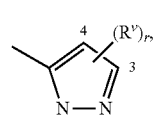 U-28
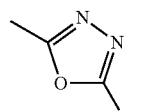 U-29
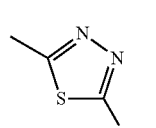 U-30
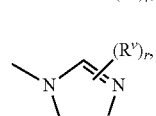 U-31

| | |
|---|---|
| 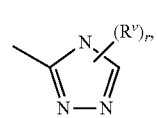 | U-32 |
| 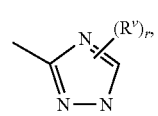 | U-33 |
| 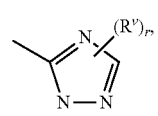 | U-34 |
| 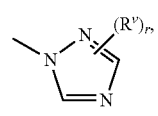 | U-35 |
| 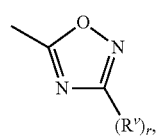 | U-36 |
| 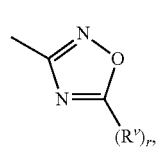 | U-37 |
| 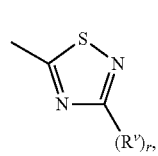 | U-38 |
| 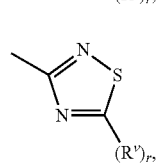 | U-39 |
| 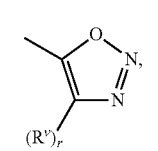 | U-40 |
| 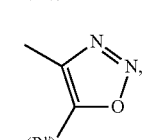 | U-41 |
| 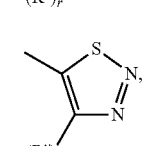 | U-42 |
| 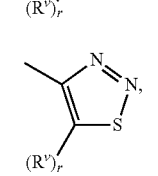 | U-43 |
| | |
|---|---|
| 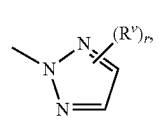 | U-44 |
| 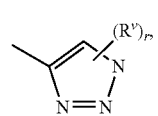 | U-45 |
| 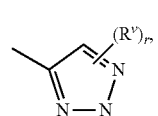 | U-46 |
| 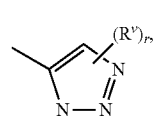 | U-47 |
| 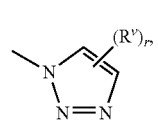 | U-48 |
| 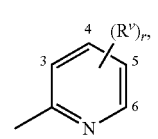 | U-49 |
| 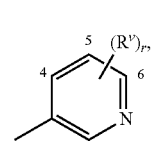 | U-50 |
| 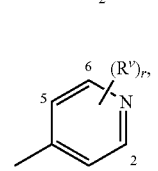 | U-51 |
| 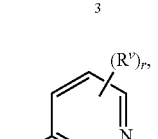 | U-52 |
| 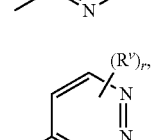 | U-53 |
| 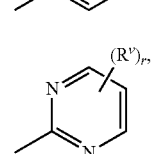 | U-54 |
| 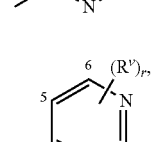 | U-55 |

-continued

U-56

U-57

U-58

U-59

U-60 and

U-61

U-81

U-82

U-83

U-84

U-85

U-86

U-87

-continued

U-89

U-90

U-91

U-92

U-93

U-94

U-95

U-96

U-97

U-98

U-99

U-100

U-101 wherein each $R^v$ is independently any substituent as defined in the Summary of the Invention for $R^1$, $R^2$, $R^3$ and r is 0, 1, 2, 3, 4 or 5, limited by the number of available positions on each U group;

each $R^4$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{4a}$ is independently H, $C_1$-$C_6$-alkyl or $C_1$-$C_6$-haloalkyl;

each $R^5$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{5a}$ is independently H or $C_1$-$C_6$-alkyl;

each $R^6$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

each $R^{6a}$ is independently H, $C_1$-$C_6$-alkyl, $C(O)R^3$ or $C(O)OR^{13}$;

each $R^7$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{7a}$ is independently $C_1$-$C_6$-alkyl or $C_1$-$C_6$-haloalkyl;

each $R^8$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_4$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{8a}$ is independently $C_1$-$C_6$-alkyl or $C_1$-$C_6$-haloalkyl;

each $R^9$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{9a}$ is independently $C_1$-$C_6$-alkyl or $C_1$-$C_6$-haloalkyl;

each $R^{10}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^{7a}$, $C(O)OR^{8a}$, $C(O)NR^{11}R^{12}$, $S(O)_mR^{9a}$ or $S(O)_2NR^{11}R^{12}$;

each $R^{11}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11a}R^{12}$, $S(O)_mR^{9a}$ and $S(O)_2NR^{11a}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11a}R^{12}$, $OR^{4a}$, $C_2$-$C_6$-alkoxyalkyl, $S(O)_mR^{9a}$, $S(O)_2NR^{11a}R^{12}$, $NR^{5a}R^{6a}$, $OC(O)R^{7a}$ and $N(R^{10})C(O)R^{7a}$;

each $R^{11a}$ is independently H, $C_1$-$C_6$-alkyl, $C_2$-$C_6$-alkenyl or $C_2$-$C_6$-alkynyl;

each $R^{12}$ is independently H, $NR^{5a}R^{5a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl, $C_6$-$C_{14}$-Cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_m R^{9a}$, $S(O)_2 NR^{11}R^{12}$, $NR^{5a}R^{6a}$, $OC(O)R^{7a}$ and $N(R^{10})C(O)R^{7a}$;

each $R^{13}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_m R^{9a}$;

each $R^{14}$ is independently $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_m R^{9a}$;

or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ and $S(O)_2 NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ and $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ and $N(R^{10})C(O)R^{7a}$;

each $R^5$ is independently $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_m R^{9a}$;

or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ and $N(R^{10})C(O)R^{7a}$;

X is O or S;

each m is independently 0, 1 or 2;

and n is 0, 1, 2, 3 or 4.

Compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions.

The diastereoisomers and/or the optical isomers can be separated according to the methods which are known per se by the man ordinary skilled in the art.

Compounds of the present invention can also exist in one or more geometric isomer forms depending on the number of double bonds in the compound, especially all syn/anti (or cis/trans) isomers and to all possible syn/anti (or cis/trans) mixtures. The invention thus relates equally to all geometric isomers and to all possible mixtures, in all proportions. The geometric isomers can be separated according to general methods, which are known per se by the man ordinary skilled in the art.

Compounds of formula (I) may be found in its tautomeric form resulting from the shift of the proton of a hydroxy, sulfanyl or amino group. Such tautomeric forms of such compounds are also part of the present invention. More generally speaking, all tautomeric forms of compounds of formula (I), as well as the tautomeric forms of the compounds which can optionally be used as intermediates in the preparation processes and which will be defined in the description of these processes, are also part of the present invention.

Further, this invention is also directed to N-oxides of the compounds of formula (I) (including all stereoisomers), and salts of the compounds of formula (I) (including all stereoisomers).

Further, this invention is directed to a formulation comprising a compound of formula (I), an N-oxide, or a salt thereof, and their use for controlling an animal pest, especially a parasitic nematode, as described above. This invention also provides a formulation comprising a compound of formula (I), an N-oxide, or a salt thereof. and at least one extender and/or at least one surfactant. In one embodiment, this invention also provides a formulation in which a compound of formula (I), an N-oxide, or a salt thereof, is present in a mixture with at least one other active compound, preferably a mixing partner as described below.

This invention provides a method for controlling an animal pest, especially a parasitic nematode, in which a compound of formula (I), an N-oxide, or a salt thereof, or a a formulation described herein is allowed to act on the animal pest and/or their habitat. In such methods, a biologically effective amount of compound or formulation is applied.

This invention also provides a method for protecting a seed and/or a germinating plant from attack by a pest, particularly a parasitic nematode, comprising the step of contacting the seed with a compound of formula (I), an N-oxide, or a salt thereof, or with a formulation described herein. In such methods, a biologically effective amount of compound or formulation is applied. This invention also relates to a seed which was obtained by such a method.

DETAILED DESCRIPTION OF A PREFERRED EMBODIMENT

Figure 1:
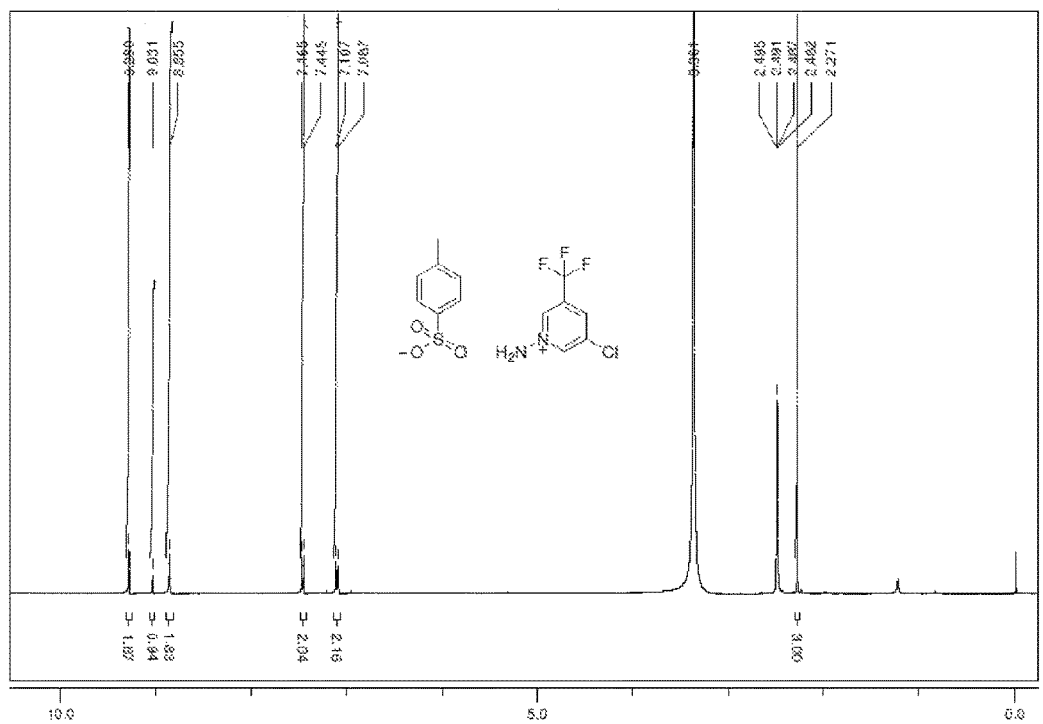
FIG. 1 depicts H-NMR spectrum of N-amino-3-chloro-5-trifluoromethyl-pyridinium p-tosylate ([$D_6$]-DMSO, 400 MHz).

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a formulation, mixture, process or method that comprises a list of elements is not necessarily limited to only those elements but may include other elements not expressly listed or inherent to such formulation, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a formulation or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used to in the present disclosure and claims, the term "nematode" refers to a living organism of the phylum Nematoda. As generally defined, a "parasite" lives or grows inside or feeds on another living organism (such as a plant, animal or human) described as the "host". As referred to in the present disclosure and claims a "parasitic nematode" is particularly a nematode that injures or damages tissue or causes other forms of disease in plants, animals (particularly vertebrates) or humans.

A parasite "infestation" refers to the presence of parasites in numbers that pose a risk to plants, humans or animals. The presence can be in the environment, e.g., in a human or animal house, or surrounding property or structures, on an agricultural crop or other type of plant, in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

As referred to in the present disclosure and claims, the terms "parasiticidal" and "parasiticidally" refers to observable effects on a parasitic nematode to provide protection to a plant, animal or human from the nematode. Parasiticidal effects typically relate to diminishing the occurrence or activity of the target parasitic nematode. Such effects on the nematode include necrosis, death, retarded growth, diminished mobility or lessened ability to remain on or in the host plant, animal or human, reduced feeding and inhibition of reproduction. These effects on parasitic nematodes provide control (including prevention, reduction or elimination) of parasitic infestation or infection of the plant, animal or human. Therefore "control" of a parasitic nematode means achieving a parasiticidal effect on the nematode. The expressions "parasiticidally effective amount" and "biologically effective amount" in the context of applying a chemical compound to control a parasitic nematode refer an amount of the compound that is sufficient to control the parasitic nematode. Likewise, the expressions "parasiticidally effective amount" and "biologically effective amount" in the context of applying a chemical compound to control an animal pest refer an amount of the compound that is sufficient to control the animal pest.

The term "agronomic" refers to the production of field crops such as for food and fiber and includes the growth of soybeans and other legumes, cereal (e.g., wheat, oats, barley, rye, rice, maize/corn), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from a parasitic nematode by administering a parasiticidally effective (i.e. biologically effective) amount of a compound of the invention, typically in the form of a formulation formulated for veterinary use, to the animal to be protected.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than one double bond such as 1,3- and 1,4-cyclohexadienyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when 20 used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkenyl", "haloalkynyl", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkenyl" include $(Cl)_2C=CHCH_2$ and $CF_3CH_2CH=CHCH_2$. Examples of "haloalkynyl" include $HC \equiv CCHCl$, $CF_3C \equiv C$, $CCl_3C \equiv C$ and $FCH_2C \equiv CCH_2$.

The chemical abbreviation C(O) as used herein represents a carbonyl moiety. For example, $C(O)CH_3$ represents an acetyl group. The chemical abbreviations $CO_2$ and C(O)O as used herein represent an ester moiety. For example, $CO_2Me$ and C(O)OMe represent a methyl ester.

"OCN" means —O—C≡N, and "SCN" means —S—C≡N.

The total number of carbon atoms in a substituent group is indicated by the "$C_j$-$C_j$" prefix where i and j are numbers from 1 to 14. $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can exceed 1, said substituents (when they exceed 1) are independently selected from the group of defined substituents, e.g., $R^1$, n is 0, 1, or 2. However, it is to be understood that n is limited by the maximum number of available positions to which the residue in question, e.g. $R^1$, can be bonded to. When a group contains a substituent which can be hydrogen, for example $R^2$ or $R^3$, then when this substituent is taken as hydrogen, it is recognized that this is equivalent to said group being unsubstituted. When a variable group is shown to be optionally attached to a position, for example $(R^v)_r$ in U-29 wherein r may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of formula (I) (e.g., substituent Q) is carbocyclic or heterocyclic. The term "ring system" denotes two or more fused rings. The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "heterocyclic ring system" denotes a ring system in which at least one ring of the ring system is a heterocyclic ring. Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a π-orbital perpendicular to the ring plane, and in which (4n+2) π electrons, where π is a positive integer, are associated with the ring to comply with Hückel's rule. When a fully unsaturated heterocyclic ring satisfies Hückel's rule, then said ring is also called a "heteroaromatic ring". The term "heteroaromatic ring system" denotes a heterocyclic ring system in which at least one ring of the ring system is aromatic.

As used herein, the following definitions shall apply unless otherwise indicated. The term "optionally substituted" is used interchangeably with the phrase "substituted or unsubstituted" or with the term "(un)substituted". The expression "optionally substituted with 1 to 4 substituents" means that no substituent is present (i.e. unsubstituted) or that 1, 2, 3 or 4 substituents are present (limited by the number of available bonding positions). Unless otherwise indicated, an optionally substituted group may have a substituent at each substitutable position of the group, and each substitution is independent of the other.

When a substituent is a 5- or 6-membered nitrogen-containing heteroaromatic ring, it may be attached to the remainder of formula (I) though any available carbon or nitrogen ring atom, unless otherwise described.

An example of phenyl optionally substituted with one to five substituents is the ring illustrated as U-1. Examples of further optionally substituted 5- or 6-membered heteroaromatic ring include the rings U-2 through U-61 wherein $R^1$ is any substituent as defined in the Summary of the Invention for $R^1$, $R^2$, $R^3$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Further and as noted above, Q can also be (among others) an 8- to 10-membered heteroaromatic bicyclic ring system optionally substituted with substituents selected from a group of substituents as defined in the Summary of Invention. Examples of optionally substituted 8-, 9- or 10-membered heteroaromatic bicyclic ring systems include the rings U-81 through U-123 wherein $R^v$ is any substituent as defined in the Summary of the Invention for Q, and r is typically an integer from 0 to 4.

Although $R^v$ groups are shown in the structures U-1 through U-123, it is noted that they do not need to be present since they are optional substituents. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of formula (I) through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

The compounds of the invention are defined in general terms by the formula (I). In the compounds of the invention, each $R^1$ preferably is independently H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, each $R^1$ is independently halogen, cyano, $OR^4$, $C_1$-$C_4$-alkyl, $C_1$-$C_4$-haloalkyl;

or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl.

Especially preferably, each $R^1$ is independently chlorine or trifluoromethyl.

$R^2$ preferably is

H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is

H, halogen, cyano, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_mR^9$.

Especially preferably, $R^2$ is hydrogen.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is

H, $C_1$-$C_4$-alkyl, $C_2$-$C_3$-alkenyl, $C(X)R^7$ or $C(O)OR$;

or $C_1$-$C_2$-alkyl substituted with $OR^4$;

or $C_1$-$C_2$-alkyl substituted with phenyl.

Especially preferably, $R^3$ is hydrogen.

Q preferably is $C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_5$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

or Q is selected from the group consisting of (U-1) to (U-61), (U-81) to (U-87), (U-89) to (U-103) and (U-105) to (U-123).

More preferably, Q is $C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;

or Q is selected from the group consisting of (U-1) to (U-61), (U-81) to (U-87), (U-89) to (U-103) and (U-105) to (U-123).

Even more preferably, Q is $C_1$-$C_6$-alkyl, $C_1$-$C_6$-haloalkyl or $C_3$-$C_7$-cycloalkyl;

or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is independently methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_mR^{9a}$.

More preferably, each $R^5$ is independently

H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$.

Especially preferably, each $R^5$ is independently

H, methyl or ethyl.

Each $R^{5a}$ preferably is independently
H or $C_1$-$C_4$-alkyl.
More preferably, each $R^{5a}$ is independently
H or $C_1$-$C_2$-alkyl.
Especially preferably, each $R^{5a}$ is independently
methyl or ethyl.
Each $R^6$ preferably is independently
H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^6$ is independently
H, $C_1$-$C_4$-alkyl, $C_1$-$C_4$-haloalkyl, $C_2$-$C_4$-alkenyl or $C_2$-$C_4$-haloalkenyl;
or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.
Especially preferably, each $R^6$ is independently
H, methyl or ethyl.
Each $R^{6a}$ preferably is independently
H, $C_1$-$C_4$-alkyl, $C(O)R^{13}$ or $C(O)OR^{13}$.
More preferably, each $R^{6a}$ is independently
H or $C_1$-$C_4$-alkyl.
Especially preferably, each $R^{6a}$ is independently
H, methyl or ethyl.
Each $R^7$ preferably is independently
H, $C_1$-$C_6$-alkyl, $C_1$-$C_6$-haloalkyl, $C_2$-$C_6$-alkenyl or $C_2$-$C_6$-haloalkenyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.
Especially preferably, each $R^7$ is independently
H, methyl, ethyl or trifluoromethyl.
Each $R^{7a}$ preferably is independently
$C_1$-$C_4$-alkyl or $C_1$-$C_4$-haloalkyl.
More preferably, each $R^{7a}$ is independently
$C_1$-$C_4$-alkyl or $C_1$-$C_2$-haloalkyl.
Especially preferably, each $R^{7a}$ is independently
methyl or ethyl.
Each $R^8$ preferably is independently
H, $C_1$-$C_4$-alkyl or $C_1$-$C_4$-haloalkyl.
More preferably, each $R^8$ is independently
$C_1$-$C_2$-alkyl or $C_1$-$C_2$-haloalkyl.
Especially preferably, each $R^8$ is independently
methyl or ethyl.
Each $R^{8a}$ preferably is independently
$C_1$-$C_4$-alkyl or $C_1$-$C_4$-haloalkyl.
More preferably, each $R^{8a}$ is independently
$C_1$-$C_4$-alkyl.
Especially preferably, each $R^{8a}$ is independently
methyl or ethyl.
Each $R^9$ preferably is independently
$C_1$-$C_4$-alkyl or $C_1$-$C_4$-haloalkyl.
More preferably, each $R^9$ is independently
$C_1$-$C_2$-alkyl, $C_1$-$C_2$-haloalkyl.
Especially preferably, each $R^9$ is independently
methyl, ethyl or trifluoromethyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently
methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{11}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.
Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ or $S(O)_2 NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.

More preferably, each $R^{15}$ is independently
$C_1$-$C_4$-alkyl or $C_1$-$C_4$-haloalkyl.
Especially preferably, each $R^{15}$ is independently methyl.

n preferably is 1, 2, 3 or 4. More preferably, n is 1, 2 or 3. Especially preferably, n is 1 or 2.

m preferably is 0, 1 or 2. More preferably, m is 0, 1 or 2. Especially preferably, m is 0 or 2.

X preferably is O or S. Especially preferably X is O.

Z preferably is O or S. Especially preferably Z is O.

In an individual embodiment, Q is U-1. In another individual embodiment, Q is U-2. In another individual embodiment, Q is U-3. In another individual embodiment, Q is U-4. In another individual embodiment, Q is U-5. In another individual embodiment, Q is U-6. In another individual embodiment, Q is U-7. In another individual embodiment, Q is U-8. In another individual embodiment, Q is U-9. In another individual embodiment, Q is U-10. In another individual embodiment, Q is U-11. In another individual embodiment, Q is U-12. In another individual embodiment, Q is U-13. In another individual embodiment, Q is U-14. In another individual embodiment, Q is U-15. In another individual embodiment, Q is U-16. In another individual embodiment, Q is U-17. In another individual embodiment, Q is U-18. In another individual embodiment, Q is U-19. In another individual embodiment, Q is U-20. In another individual embodiment, Q is U-21. In another individual embodiment, Q is U-22. In another individual embodiment, Q is U-23. In another individual embodiment, Q is U-24. In another individual embodiment, Q is U-25. In another individual embodiment, Q is U-26. In another individual embodiment, Q is U-27. In another individual embodiment, Q is U-28. In another individual embodiment, Q is U-29. In another individual embodiment, Q is U-30. In another individual embodiment, Q is U-31. In another individual embodiment, Q is U-32. In another individual embodiment, Q is U-33. In another individual embodiment, Q is U-34. In another individual embodiment, Q is U-35. In another individual embodiment, Q is U-36. In another individual embodiment, Q is U-37. In another individual embodiment, Q is U-38. In another individual embodiment, Q is U-39. In another individual embodiment, Q is U-40. In another individual embodiment, Q is U-41. In another individual embodiment, Q is U-42. In another individual embodiment, Q is U-43. In another individual embodiment, Q is U-44. In another individual embodiment, Q is U-45. In another individual embodiment, Q is U-46. In another individual embodiment, Q is U-47. In another individual embodiment, Q is U-48. In another individual embodiment, Q is U-49. In another individual embodiment, Q is U-50. In another individual embodiment, Q is U-51. In another individual embodiment, Q is U-52. In another individual embodiment, Q is U-53. In another individual embodiment, Q is U-54. In another individual embodiment, Q is U-55. In another individual embodiment, Q is U-56. In another individual embodiment, Q is U-57. In another individual embodiment, Q is U-58. In another individual embodiment, Q is U-59. In another individual embodiment, Q is U-60. In another individual embodiment, Q is U-61. In another individual embodiment, Q is U-81. In another individual embodiment, Q is U-82. In another individual embodiment, Q is U-83. In another individual embodiment, Q is U-84. In another individual embodiment, Q is U-85. In another individual embodiment, Q is U-86. In another individual embodiment, Q is U-87. In another individual embodiment, Q is U-89. In another individual embodiment, Q is U-90. In another individual embodiment, Q is U-91. In another individual embodiment, Q is U-92. In another individual embodiment, Q is U-93. In another individual embodiment, Q is U-94. In another individual embodiment, Q is U-95. In another individual embodiment, Q is U-96. In another individual embodiment, Q is U-97. In another individual embodiment, Q is U-98. In another individual embodiment, Q is U-99. In another individual embodiment, Q is U-100. In another individual embodiment, Q is U-101. In another individual embodiment, Q is U-102. In another individual embodiment, Q is U-103. In another individual embodiment, Q is U-105. In another individual embodiment, Q is U-106. In another individual embodiment, Q is U-107. In another individual embodiment, Q is U-108. In another individual embodiment, Q is U-109. In another individual embodiment, Q is U-110. In another individual embodiment, Q is U-111. In another individual embodiment, Q is U-112. In another individual embodiment, Q is U-113. In another individual embodiment, Q is U-114. In another individual embodiment, Q is U-115. In another individual embodiment, Q is U-116. In another individual embodiment, Q is U-117. In another individual embodiment, Q is U-118. In another individual embodiment, Q is U-119. In another individual embodiment, Q is U-120. In another individual embodiment, Q is U-121. In another individual embodiment, Q is U-122. In another individual embodiment, Q is U-123.

In all cases with Q is defined to be one of (U-1) to (U-61), (U-81) to (U-87), (U-89) to (U-103) or (U-105) to (U-123), each $R^v$ preferably is independently
halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;
$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

More preferably, each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently fluor, chlor, methoxy, trifluoromethyl, trifluoromethoxy or methyl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

A wide variety of synthetic methods are known in the art to enable preparation of aromatic and nonaromatic heterocyclic rings and ring systems; for extensive reviews see the eight volume set of Comprehensive Heterocyclic Chemistry, A. R. Katritzky and C. W. Rees editors-in-chief, Pergamon Press, Oxford, 1984 and the twelve volume set of Comprehensive Heterocyclic Chemistry II, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds selected from formula (I), (including all stereoisomers, N-oxides, and salts thereof), typically exist in more than one form, and formula (I) thus includes all crystalline and non-crystalline forms of the compounds that formula (I) represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by formula (I) can exhibit beneficial effects (e.g., suitability for preparation of useful formulations, improved biological performance) relative to another polymorph or a mixture of polymorphs of the same compound represented by formula (I). Preparation and isolation of a particular polymorph of a compound represented by formula (I) can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in Comprehensive Organic Synthesis, vol. 7, pp 748-750, S. V. Ley, Ed., Pergamon Press; M. Tisler and B. Stanovnik in Comprehensive Heterocyclic Chemistry, vol. 3, pp 18-20, A. J. Boulton and A. McKillop, Eds., Pergamon Press; M. R. Grimmett and B. R. T. Keene in Advances in Heterocyclic Chemistry, vol. 43, pp 149-161, A. R. Katritzky, Ed., Academic Press; M. Tisler and B. Stanovnik in Advances in Heterocyclic Chemistry, vol. 9, pp 285-291, A. R. Katritzky and A. J. Boulton, Eds., Academic Press; and G. W. H. Cheeseman and E. S. G. Werstiuk in Advances in Heterocyclic Chemistry, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of formula (I) are useful for control of parasitic nematodes. The salts of the compounds of formula (I) include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of formula (I) contains an acidic moiety such as a carboxylic acid, phenol or sulfonylamide (i.e. when $R^3$ is H), salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from formula (I), N-oxides and salts thereof.

Embodiments of the present invention as described in the Summary of the Invention include those described below. In the following Embodiments, formula (I) includes stereoisomers, N-oxides, and salts thereof, and reference to "a compound of formula (I)" includes the definitions of substituents specified in the Summary of the Invention unless further defined in the embodiments.

EMBODIMENTS

Embodiment 1

The compounds of the invention are defined in general terms by the formula (I). In a preferred embodiment, the compounds of the invention are defined by formula (Ia):

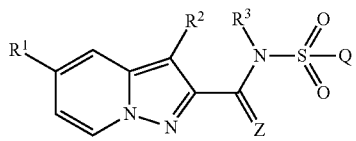

(Ia)

wherein
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^2$, $R^{13}$, $R^{14}$, $R^{15}$,
Z, Q, $R^v$, r, X, m and n are as defined above in the Summary of the Invention.

$R^1$ preferably is
  H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;
  or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;
  or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, $R^1$ is
halogen, cyano, $OR^4$, $C_1$-$C_4$-alkyl, $C_1$-$C_4$-haloalkyl;
  or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

Especially preferably, $R^1$ is
trifluoromethyl.

$R^2$ preferably is
  H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;
  or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;
  or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is
H, halogen, cyano, $S(O)_mR^9$ or $S(O)_2NR^{11}R^{12}$;
  or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;
  or $C_1$-$C_4$-alkyl substituted with 1 to 2 substituents independently selected from the group consisting of cyano, $OR^4$ and $S(O)_mR^9$.

Especially preferably, $R^2$ is hydrogen.

$R^3$ preferably is
  H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;
  or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{5a}$;
  or $C_1$-$C_4$-alkyl substituted with 1 to 4 substituents independently selected from the group consisting of cyano, $OR^4$, $C(X)R^7$ and $C(O)OR^8$;
  or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is
H, $C_1$-$C_4$-alkyl, $C_2$-$C_3$-alkenyl, $C(X)R^7$ or $C(O)OR^8$;
  or $C_1$-$C_2$-alkyl substituted with $OR^4$;
  or $C_1$-$C_2$-alkyl substituted with phenyl.

Especially preferably, $R^3$ is hydrogen.

Q preferably is
  $C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;
  or Q is selected from the group consisting of (U-1) to (U-61), (U-81) to (U-87), (U-89) to (U-103) and (U-105) to (U-123).

More preferably, Q is
$C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;
  or Q is selected from the group consisting of (U-1) to (U-61), (U-81) to (U-87), (U-89) to (U-103) and (U-105) to (U-123).

Even more preferably, Q is
$C_1$-$C_6$-alkyl, $C_1$-$C_6$-haloalkyl or $C_3$-$C_7$-cycloalkyl;
  or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently
H, $C_1$-$C_4$-alkyl or $C_1$-$C_4$-haloalkyl;
  or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently
H, $C_1$-$C_4$-alkyl or $C_1$-$C_4$-haloalkyl.

Especially preferably, each $R^4$ is independently methyl, ethyl, propyl, isopropyl, difluoromethyl or trifluoromethyl.

Each $R^{4a}$ preferably is independently
H, $C_1$-$C_6$-alkyl or $C_1$-$C_6$-haloalkyl.

More preferably, each $R^{4a}$ is independently
$C_1$-$C_4$-alkyl or $C_1$-$C_4$-haloalkyl.

Especially preferably, each $R^{4a}$ is independently
methyl or ethyl.

Each $R^5$ preferably is independently
H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_m R^{9a}$.

More preferably, each $R^5$ is independently
H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11} R^{12}$.

Especially preferably, each $R^5$ is independently
H, methyl or ethyl.

Each $R^{5a}$ preferably is independently
H or $C_1$-$C_4$-alkyl.

More preferably, each $R^{5a}$ is independently
H or $C_1$-$C_2$-alkyl.

Especially preferably, each $R^{5a}$ is independently
methyl or ethyl.

Each $R^6$ preferably is independently
H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$ More preferably, each $R^6$ is independently
H, $C_1$-$C_4$-alkyl, $C_1$-$C_4$-haloalkyl, $C_2$-$C_4$-alkenyl or $C_2$-$C_4$-haloalkenyl;
or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently
H, methyl or ethyl.

Each $R^{6a}$ preferably is independently
H, $C_1$-$C_4$-alkyl, $C(O)R^{13}$ or $C(O)OR^{13}$.

More preferably, each $R^{6a}$ is independently
H or $C_1$-$C_4$-alkyl.

Especially preferably, each $R^{6a}$ is independently
H, methyl or ethyl.

Each $R^7$ preferably is independently
H, $C_1$-$C_6$-alkyl, $C_1$-$C_6$-haloalkyl, $C_2$-$C_6$-alkenyl or $C_2$-$C_6$-haloalkenyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently
H, methyl, ethyl or trifluoromethyl.

Each $R^7$ preferably is independently
$C_1$-$C_4$-alkyl or $C_1$-$C_4$-haloalkyl.

More preferably, each $R^{7a}$ is independently
$C_1$-$C_4$-alkyl or $C_1$-$C_2$-haloalkyl.

Especially preferably, each $R^{7a}$ is independently
methyl or ethyl.

Each $R^8$ preferably is independently
H, $C_1$-$C_4$-alkyl or $C_1$-$C_4$-haloalkyl.

More preferably, each $R^8$ is independently
$C_1$-$C_2$-alkyl or $C_1$-$C_2$-haloalkyl.

Especially preferably, each $R^8$ is independently
methyl or ethyl.

Each $R^{8a}$ preferably is independently
$C_1$-$C_4$-alkyl or $C_1$-$C_4$-haloalkyl.

More preferably, each $R^{8a}$ is independently
$C_1$-$C_4$-alkyl.

Especially preferably, each $R^{8a}$ is independently
methyl or ethyl.

Each $R^9$ preferably is independently
$C_1$-$C_4$-alkyl or $C_1$-$C_4$-haloalkyl.

More preferably, each $R^9$ is independently
$C_1$-$C_2$-alkyl, $C_1$-$C_2$-haloalkyl.

Especially preferably, each $R^9$ is independently
methyl, ethyl or trifluoromethyl.

Each $R^{9a}$ preferably is independently
$C_1$-$C_4$-alkyl or $C_1$-$C_4$-haloalkyl.

More preferably, each $R^{9a}$ is independently
$C_1$-$C_4$-alkyl or $C_1$-$C_2$-haloalkyl.

Especially preferably, each $R^{9a}$ is independently
methyl, ethyl or trifluoromethyl.

Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.

More preferably, each $R^{10}$ is independently
H, $C_1$-$C_4$-alkyl, $C_2$-$C_3$-alkenyl or $C_3$-$C_7$-cycloalkyl.

Especially preferably, each $R^{10}$ is independently
H or methyl.

Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.

More preferably, each $R^{11}$ is independently
H, $C_1$-$C_4$-alkyl, $C_1$-$C_4$-haloalkyl.

Especially preferably, each $R^{11}$ is independently
H, methyl or ethyl.

Each $R^{11a}$ preferably is independently
H, $C_1$-$C_4$-alkyl, $C_2$-$C_3$-alkenyl or $C_2$-$C_3$-alkynyl.

More preferably, each $R^{11a}$ is independently
H, $C_1$-$C_4$-alkyl, allyl or propargyl.

Especially preferably, each $R^{11a}$ is independently
H, methyl or ethyl.

Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{12}$ is independently
H, $C_1$-$C_4$-alkyl or $C_1$-$C_4$-haloalkyl.

Especially preferably, each $R^{12}$ is independently
H, methyl or ethyl.

Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{13}$ is independently
H, $C_1$-$C_4$-alkyl or $C_1$-$C_4$-haloalkyl.

Especially preferably, each $R^{13}$ is independently
methyl.

Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$;
or $C_1$-$C_6$-alkyl, each substituted with 1 to 4 substituents independently selected from the group consisting of cyano, nitro, $OR^4$, $NR^5 R^6$, $C(X)R^7$, $C(O)OR^8$, $C(O)NR^{11}R^{12}$, $S(O)_m R^9$ or $S(O)_2 NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5 R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^{14}$ is independently $C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Especially preferably, each $R^{14}$ is independently $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Each $R^{15}$ preferably is independently $C_1$-$C_4$-alkyl or $C_1$-$C_4$-haloalkyl;

or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.

More preferably, each $R^{15}$ is independently $C_1$-$C_4$-alkyl or $C_1$-$C_4$-haloalkyl.

Especially preferably, each $R^{15}$ is independently methyl.

n preferably is 1, 2, 3 or 4. More preferably, n is 1, 2 or 3. Especially preferably, n is 1 or 2.

m preferably is 0, 1 or 2. More preferably, m is 0, 1 or 2. Especially preferably, m is 0 or 2.

X preferably is O or S. Especially preferably X is O.

Z preferably is O or S. Especially preferably Z is O.

In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$; $C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

More preferably, each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently fluor, chlor, methoxy, trifluoromethyl, trifluoromethoxy or methyl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

A specific aspect of the compounds of this embodiment are compounds which are represented by formula (Ia-1)

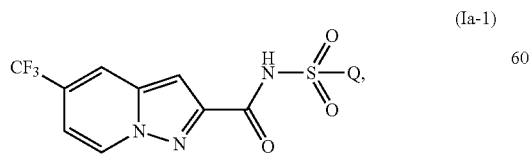

(Ia-1)

wherein the structural elements are defined as given above for embodiment 1.

Embodiment 2

The compounds of the invention are defined in general terms by the formula (I). In another preferred embodiment, the compounds of the invention are defined by formula (Ib):

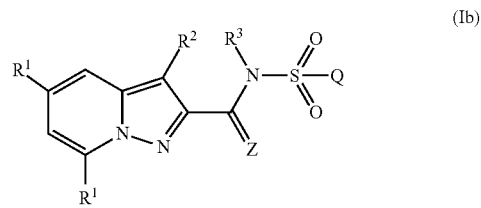

(Ib)

wherein $R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, $R^v$, r, X, m and n are as defined above in the Summary of the Invention.

$R^1$ preferably is

H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, $R^1$ is halogen, cyano, $OR^4$, $C_1$-$C_4$-alkyl, $C_1$-$C_4$-haloalkyl;

or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

Especially preferably, $R^1$ is chlorine or trifluoromethyl.

$R^2$ preferably is

H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is

H, halogen, cyano, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_mR^9$.

Especially preferably, $R^2$ is hydrogen.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^1$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is

H, $C_1$-$C_4$-alkyl, $C_2$-$C_3$-alkenyl, $C(X)R^7$ or $C(O)OR^8$;

or $C_1$-$C_2$-alkyl substituted with $OR^4$;

or $C_1$-$C_2$-alkyl substituted with phenyl.

Especially preferably, $R^3$ is hydrogen.

Q preferably is $C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

or Q is selected from the group consisting of (U-1) to (U-61), (U-81) to (U-87), (U-89) to (U-103) and (U-105) to (U-123).

More preferably, Q is $C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;

or Q is selected from the group consisting of (U-1) to (U-61), (U-81) to (U-87), (U-89) to (U-103) and (U-105) to (U-123).

Even more preferably, Q is $C_1$-$C_6$-alkyl, $C_1$-$C_6$-haloalkyl or $C_3$-$C_7$-cycloalkyl;

or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is independently methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_mR^{9a}$.

More preferably, each $R^5$ is independently

H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$.

Especially preferably, each $R^5$ is independently

H, methyl or ethyl.

Each $R^{5a}$ preferably is independently

H or $C_1$-$C_4$-alkyl.

More preferably, each $R^{5a}$ is independently

H or $C_1$-$C_2$-alkyl.

Especially preferably, each $R^{5a}$ is independently methyl or ethyl.

Each $R^6$ preferably is independently

H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^6$ is independently

H, $C_1$-$C_4$-alkyl, $C_1$-$C_4$-haloalkyl, $C_2$-$C_4$-alkenyl or $C_2$-$C_4$-haloalkenyl;

or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently

H, methyl or ethyl.

Each $R^{6a}$ preferably is independently

H, $C_1$-$C_4$-alkyl, $C(O)R^{13}$ or $C(O)OR^{13}$.

More preferably, each $R^{6a}$ is independently

H or $C_1$-$C_4$-alkyl.

Especially preferably, each $R^{6a}$ is independently

H, methyl or ethyl.

Each $R^7$ preferably is independently

H, $C_1$-$C_6$-alkyl, $C_1$-$C_6$-haloalkyl, $C_2$-$C_6$-alkenyl or $C_2$-$C_6$-haloalkenyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^4a$ and $S(O)R^{9a}$.

More preferably, each $R^7$ is independently

H, $C_1$-$C_4$-alkyl or $C_1$-$C_4$-haloalkyl;

or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently

H, methyl, ethyl or trifluoromethyl.

Each $R^{7a}$ preferably is independently $C_1$-$C_4$-alkyl or $C_1$-$C_4$-haloalkyl.

More preferably, each $R^{7a}$ is independently $C_1$-$C_4$-alkyl or $C_1$-$C_2$-haloalkyl.

Especially preferably, each $R^{7a}$ is independently methyl or ethyl.

Each $R^8$ preferably is independently
H, $C_1$-$C_4$-alkyl or $C_1$-$C_4$-haloalkyl.

More preferably, each $R^8$ is independently
$C_1$-$C_2$-alkyl or $C_1$-$C_2$-haloalkyl.

Especially preferably, each $R^8$ is independently
methyl or ethyl.

Each $R^{8a}$ preferably is independently
$C_1$-$C_4$-alkyl or $C_1$-$C_4$-haloalkyl.

More preferably, each $R^{8a}$ is independently
$C_1$-$C_4$-alkyl.

Especially preferably, each $R^{8a}$ is independently
methyl or ethyl.

Each $R^9$ preferably is independently
$C_1$-$C_4$-alkyl or $C_1$-$C_4$-haloalkyl.

More preferably, each $R^9$ is independently
$C_1$-$C_2$-alkyl, $C_1$-$C_2$-haloalkyl.

Especially preferably, each $R^9$ is independently
methyl, ethyl or trifluoromethyl.

Each $R^{9a}$ preferably is independently
$C_1$-$C_4$-alkyl or $C_1$-$C_4$-haloalkyl.

More preferably, each $R^{9a}$ is independently
$C_1$-$C_4$-alkyl or $C_1$-$C_2$-haloalkyl.

Especially preferably, each $R^{9a}$ is independently
methyl, ethyl or trifluoromethyl.

Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.

More preferably, each $R^{10}$ is independently
H, $C_1$-$C_4$-alkyl, $C_2$-$C_3$-alkenyl or $C_3$-$C_7$-cycloalkyl.

Especially preferably, each $R^{10}$ is independently
H or methyl.

Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.

More preferably, each $R^{11}$ is independently
H, $C_1$-$C_4$-alkyl, $C_1$-$C_4$-haloalkyl.

Especially preferably, each $R^{11}$ is independently
H, methyl or ethyl.

Each $R^{11a}$ preferably is independently
H, $C_1$-$C_4$-alkyl, $C_2$-$C_3$-alkenyl or $C_2$-$C_3$-alkynyl.

More preferably, each $R^{11a}$ is independently
H, $C_1$-$C_4$-alkyl, allyl or propargyl.

Especially preferably, each $R^{11a}$ is independently
H, methyl or ethyl.

Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{12}$ is independently
H, $C_1$-$C_4$-alkyl or $C_1$-$C_4$-haloalkyl.

Especially preferably, each $R^{12}$ is independently
H, methyl or ethyl.

Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{13}$ is independently
H, $C_1$-$C_4$-alkyl or $C_1$-$C_4$-haloalkyl.

Especially preferably, each $R^{13}$ is independently
methyl.

Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$;

or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^{14}$ is independently
$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)R^9$ or $S(O)_2NR^{11}R^{12}$;

Each $R^{15}$ preferably is independently
$C_1$-$C_4$-alkyl or $C_1$-$C_4$-haloalkyl;

or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.

More preferably, each $R^{15}$ is independently
$C_1$-$C_4$-alkyl or $C_1$-$C_4$-haloalkyl.

Especially preferably, each $R^{15}$ is independently
methyl.

n preferably is 1, 2, 3 or 4. More preferably, n is 1, 2 or 3. Especially preferably, n is 1 or 2.

m preferably is 0, 1 or 2. More preferably, m is 0, 1 or 2. Especially preferably, m is 0 or 2.

X preferably is O or S. Especially preferably X is O.

Z preferably is O or S. Especially preferably Z is O.

In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-19. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR$, $C(O)NR^{11}R^{12}$, $S(O)_mR^9$ or $S(O)_2NR^{11}R^{12}$.

More preferably, each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently fluor, chlor, methoxy, trifluoromethyl, trifluoromethoxy or methyl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

A specific aspect of the compounds of this embodiment are compounds which are represented by formula (Ib-1)

(Ib-1)

[Chemical structure: pyrazolopyridine with CF₃, Cl substituents and N-S(O)₂-Q sulfonamide group]

wherein the structural elements are defined as given above for embodiment 2.

Embodiment 3

The compounds of the invention are defined in general terms by the formula (I). In another preferred embodiment, the compounds of the invention are defined by formula (Ic):

(Ic)

[Chemical structure with R¹, R², R³ substituents]

wherein
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, $R^v$, r, X, m and n are as defined above in the Summary of the Invention.

$R^1$ preferably is
H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^9$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, $R^1$ is
halogen, cyano, $OR^4$, $C_1$-$C_4$-alkyl, $C_1$-$C_4$-haloalkyl;
or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

Especially preferably, $R^1$ is
trifluoromethyl.

$R^2$ preferably is
H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is
H, halogen, cyano, $S(O)_mR^9$ or $S(O)_2NR^{11}R^{12}$;
or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;
or $C_1$-$C_4$-alkyl substituted with 1 to 2 substituents independently selected from the group consisting of cyano, $OR^4$ and $S(O)_mR^9$.

Especially preferably, $R^2$ is hydrogen.

$R^3$ preferably is
H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is
H, $C_1$-$C_4$-alkyl, $C_2$-$C_3$-alkenyl, $C(X)R^7$ or $C(O)OR^8$;
or $C_1$-$C_2$-alkyl substituted with $OR^4$;
or $C_1$-$C_2$-alkyl substituted with phenyl.

Especially preferably, $R^3$ is hydrogen.

Q preferably is
$C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

or Q is selected from the group consisting of (U-1) to (U-61), (U-81) to (U-87), (U-89) to (U-103) and (U-105) to (U-123).

More preferably, Q is
$C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;

or Q is selected from the group consisting of (U-1) to (U-61), (U-81) to (U-87), (U-89) to (U-103) and (U-105) to (U-123).

Even more preferably, Q is
$C_1$-$C_6$-alkyl, $C_1$-$C_6$-haloalkyl or $C_3$-$C_7$-cycloalkyl;
or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently
H, $C_1$-$C_4$-alkyl or $C_1$-$C_4$-haloalkyl;
or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently
H, $C_1$-$C_4$-alkyl or $C_1$-$C_4$-haloalkyl.

Especially preferably, each $R^4$ is independently methyl, ethyl, propyl, isopropyl, difluoromethyl or trifluoromethyl.

Each $R^{4a}$ preferably is independently
H, $C_1$-$C_6$-alkyl or $C_1$-$C_6$-haloalkyl.

More preferably, each $R^{4a}$ is independently
$C_1$-$C_4$-alkyl or $C_1$-$C_4$-haloalkyl.

Especially preferably, each $R^{4a}$ is independently
methyl or ethyl.

Each $R^5$ preferably is independently
H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2NR^{11}R^{12}$;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_m R^{9a}$.

More preferably, each $R^5$ is independently
H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2NR^{11}R^{12}$.

Especially preferably, each $R^5$ is independently
H, methyl or ethyl.

Each $R^{5a}$ preferably is independently
H or $C_1$-$C_4$-alkyl.

More preferably, each $R^{5a}$ is independently
H or $C_1$-$C_2$-alkyl.

Especially preferably, each $R^5$ is independently
methyl or ethyl.

Each $R^6$ preferably is independently
H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^6$ is independently
H, $C_1$-$C_4$-alkyl, $C_1$-$C_4$-haloalkyl, $C_2$-$C_4$-alkenyl or $C_2$-$C_4$-haloalkenyl;
or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently
H, methyl or ethyl.

Each $R^{6a}$ preferably is independently
H, $C_1$-$C_4$-alkyl, $C(O)R^{13}$ or $C(O)OR^{13}$.

More preferably, each $R^{6a}$ is independently
H or $C_1$-$C_4$-alkyl.

Especially preferably, each $R^{6a}$ is independently
H, methyl or ethyl.

Each $R^7$ preferably is independently
H, $C_1$-$C_6$-alkyl, $C_1$-$C_6$-haloalkyl, $C_2$-$C_6$-alkenyl or $C_2$-$C_6$-haloalkenyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently
H, methyl, ethyl or trifluoromethyl.

Each $R^{7a}$ preferably is independently
$C_1$-$C_4$-alkyl or $C_1$-$C_4$-haloalkyl.

More preferably, each $R^{7a}$ is independently
$C_1$-$C_4$-alkyl or $C_1$-$C_2$-haloalkyl.

Especially preferably, each $R^{7a}$ is independently
methyl or ethyl.

Each $R^8$ preferably is independently
H, $C_1$-$C_4$-alkyl or $C_1$-$C_4$-haloalkyl.

More preferably, each $R^8$ is independently
$C_1$-$C_2$-alkyl or $C_1$-$C_2$-haloalkyl.

Especially preferably, each $R^8$ is independently
methyl or ethyl.

Each $R^{8a}$ preferably is independently
$C_1$-$C_4$-alkyl or $C_1$-$C_4$-haloalkyl.

More preferably, each $R^{8a}$ is independently
$C_1$-$C_4$-alkyl.

Especially preferably, each $R^{8a}$ is independently
methyl or ethyl.

Each $R^9$ preferably is independently
$C_1$-$C_4$-alkyl or $C_1$-$C_4$-haloalkyl.

More preferably, each $R^9$ is independently
$C_1$-$C_2$-alkyl, $C_1$-$C_2$-haloalkyl.

Especially preferably, each $R^9$ is independently
methyl, ethyl or trifluoromethyl.

Each $R^{9a}$ preferably is independently
$C_1$-$C_4$-alkyl or $C_1$-$C_4$-haloalkyl.

More preferably, each $R^{9a}$ is independently
$C_1$-$C_4$-alkyl or $C_1$-$C_2$-haloalkyl.

Especially preferably, each $R^{9a}$ is independently
methyl, ethyl or trifluoromethyl.

Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.

More preferably, each $R^{10}$ is independently
H, $C_1$-$C_4$-alkyl, $C_2$-$C_3$-alkenyl or $C_3$-$C_7$-cycloalkyl.

Especially preferably, each $R^{10}$ is independently
H or methyl.

Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.

More preferably, each $R^{11}$ is independently
H, $C_1$-$C_4$-alkyl, $C_1$-$C_4$-haloalkyl.

Especially preferably, each $R^{11}$ is independently
H, methyl or ethyl.

Each $R^{11a}$ preferably is independently
H, $C_1$-$C_4$-alkyl, $C_2$-$C_3$-alkenyl or $C_2$-$C_3$-alkynyl.

More preferably, each $R^{11a}$ is independently
H, $C_1$-$C_4$-alkyl, allyl or propargyl.

Especially preferably, each $R^{11a}$ is independently
H, methyl or ethyl.

Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{12}$ is independently
H, $C_1$-$C_4$-alkyl or $C_1$-$C_4$-haloalkyl.
Especially preferably, each $R^{12}$ is independently
H, methyl or ethyl.
Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;
Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.
More preferably, each $R^{15}$ is independently
$C_1$-$C_4$-alkyl or $C_1$-$C_4$-haloalkyl.

Especially preferably, each $R^{15}$ is independently
methyl.
n preferably is 1, 2, 3 or 4. More preferably, n is 1, 2 or 3. Especially preferably, n is 1 or 2.
m preferably is 0, 1 or 2. More preferably, m is 0, 1 or 2. Especially preferably, m is 0 or 2.
X preferably is O or S. Especially preferably X is O.
Z preferably is O or S. Especially preferably Z is O.
In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-18. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

More preferably, each $R^v$ is independently
halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently
fluor, chlor, methoxy, trifluoromethyl, trifluoromethoxy or methyl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

Embodiment 4

The compounds of the invention are defined in general terms by the formula (I). In a preferred embodiment, the compounds of the invention are defined by formula (Id):

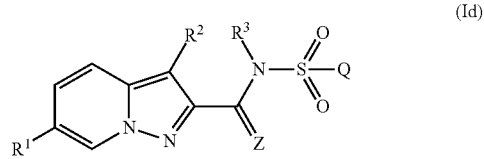

(Id)

wherein
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, $R^v$, r, X, m and n are as defined above in the Summary of the Invention.

$R^1$ preferably is
H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_1R^9$ and $S(O)_2NR^{11}R^{12}$.

More preferably, $R^1$ is
halogen, cyano, $OR^4$, $C_1$-$C_4$-alkyl, $C_1$-$C_4$-haloalkyl;
or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

Especially preferably, $R^1$ is
trifluoromethyl.

$R^2$ preferably is
H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is

H, halogen, cyano, $S(O)_m R^9$ or $S(O)_2 NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_m R^9$.

Especially preferably, $R^2$ is hydrogen.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_m R^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_m R^9$ and $S(O)_2 NR^{11}R^{12}$.

More preferably, $R^3$ is

H, $C_1$-$C_4$-alkyl, $C_2$-$C_3$-alkenyl, $C(X)R^7$ or $C(O)OR$;

or $C_1$-$C_2$-alkyl substituted with $OR^4$;

or $C_1$-$C_2$-alkyl substituted with phenyl.

Especially preferably, $R^3$ is hydrogen.

Q preferably is $C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_m R^9$, $S(O)_2 NR^{11}R^{12}$, $N(R^{10})C(O)R^7$, $N(R^{10})C(O)NR^{11}R^{12}$, $N(R^{10})S(O)_2 R^9$, $N(R^{10})S(O)_2 NR^{11}R^{12}$ and $R^{14}$;

or Q is selected from the group consisting of (U-1) to (U-61), (U-81) to (U-87), (U-89) to (U-103) and (U-105) to (U-123).

More preferably, Q is $C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_m R^9$ and $S(O)_2 NR^{11}R^{12}$;

or Q is selected from the group consisting of (U-1) to (U-61), (U-81) to (U-87), (U-89) to (U-103) and (U-105) to (U-123).

Even more preferably, Q is $C_1$-$C_6$-alkyl, $C_1$-$C_6$-haloalkyl or $C_3$-$C_7$-cycloalkyl;

or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is independently methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_m R^{9a}$.

More preferably, each $R^5$ is independently

H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$.

Especially preferably, each $R^5$ is independently

H, methyl or ethyl.

Each $R^{5a}$ preferably is independently

H or $C_1$-$C_4$-alkyl.

More preferably, each $R^{5a}$ is independently

H or $C_1$-$C_2$-alkyl.

Especially preferably, each $R^5$ is independently methyl or ethyl.

Each $R^6$ preferably is independently

H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^4$ and $S(O)_m R^{9a}$.

More preferably, each $R^6$ is independently

H, $C_1$-$C_4$-alkyl, $C_1$-$C_4$-haloalkyl, $C_2$-$C_4$-alkenyl or $C_2$-$C_4$-haloalkenyl;

or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently

H, methyl or ethyl.

Each $R^{6a}$ preferably is independently

H, $C_1$-$C_4$-alkyl, $C(O)R^{13}$ or $C(O)OR^{13}$.

More preferably, each $R^{6a}$ is independently

H or $C_1$-$C_4$-alkyl.

Especially preferably, each $R^{6a}$ is independently

H, methyl or ethyl.

Each $R^7$ preferably is independently

H, $C_1$-$C_6$-alkyl, $C_1$-$C_6$-haloalkyl, $C_2$-$C_6$-alkenyl or $C_2$-$C_6$-haloalkenyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.
Especially preferably, each $R^7$ is independently
H, methyl, ethyl or trifluoromethyl.
Each $R^{7a}$ preferably is independently
$C_1$-$C_4$-alkyl or $C_1$-$C_4$-haloalkyl.
More preferably, each $R^{7a}$ is independently
$C_1$-$C_4$-alkyl or $C_1$-$C_2$-haloalkyl.
Especially preferably, each $R^{7a}$ is independently
methyl or ethyl.
Each $R^8$ preferably is independently
H, $C_1$-$C_4$-alkyl or $C_1$-$C_4$-haloalkyl.
More preferably, each $R^8$ is independently
$C_1$-$C_2$-alkyl or $C_1$-$C_2$-haloalkyl.
Especially preferably, each $R^8$ is independently
methyl or ethyl.
Each $R^{8a}$ preferably is independently
$C_1$-$C_4$-alkyl or $C_1$-$C_4$-haloalkyl.
More preferably, each $R^{8a}$ is independently
$C_1$-$C_4$-alkyl.
Especially preferably, each $R^{8a}$ is independently
methyl or ethyl.
Each $R^9$ preferably is independently
$C_1$-$C_4$-alkyl or $C_1$-$C_4$-haloalkyl.
More preferably, each $R^9$ is independently
$C_1$-$C_2$-alkyl, $C_1$-$C_2$-haloalkyl.
Especially preferably, each $R^9$ is independently
methyl, ethyl or trifluoromethyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently
methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{10}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.

Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ or $S(O)_2 NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2 NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2 NR^{11}R^{12}$;
Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_m R^9$ and $S(O)_2 NR^{11}R^{12}$.
More preferably, each $R^{15}$ is independently
$C_1$-$C_4$-alkyl or $C_1$-$C_4$-haloalkyl.
Especially preferably, each $R^{15}$ is independently
methyl.

n preferably is 1, 2, 3 or 4. More preferably, n is 1, 2 or 3. Especially preferably, n is 1 or 2.

m preferably is 0, 1 or 2. More preferably, m is 0, 1 or 2. Especially preferably, m is 0 or 2.

X preferably is O or S. Especially preferably X is O.

Z preferably is O or S. Especially preferably Z is O.

In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$; $C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

More preferably, each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently
fluor, chlor, methoxy, trifluoromethyl, trifluoromethoxy or methyl.
In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

Embodiment 5

The compounds of the invention are defined in general terms by the formula (I). In another preferred embodiment, the compounds of the invention are defined by formula (Ie):

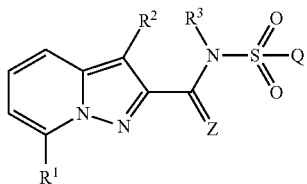

(Ie)

wherein
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, $R^v$, r, X, m and n are as defined above in the Summary of the Invention.

$R^1$ preferably is
H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, $R^1$ is
halogen, cyano, $OR^4$, $C_1$-$C_4$-alkyl, $C_1$-$C_4$-haloalkyl;
or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;
Especially preferably, $R^1$ is
trifluoromethyl.

$R^2$ preferably is
H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is
H, halogen, cyano, $S(O)_mR^9$ or $S(O)_2NR^{11}R^{12}$;
or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;
or $C_1$-$C_4$-alkyl substituted with 1 to 2 substituents independently selected from the group consisting of cyano, $OR^4$ and $S(O)_mR^9$.

Especially preferably, $R^2$ is hydrogen.

$R^3$ preferably is
H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is
H, $C_1$-$C_4$-alkyl, $C_2$-$C_3$-alkenyl, $C(X)R^7$ or $C(O)OR^8$;
or $C_1$-$C_2$-alkyl substituted with $OR^4$;
or $C_1$-$C_2$-alkyl substituted with phenyl.

Especially preferably, $R^3$ is hydrogen.

Q preferably is
$C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

or Q is selected from the group consisting of (U-1) to (U-61), (U-81) to (U-87), (U-89) to (U-103) and (U-105) to (U-123).

More preferably, Q is
$C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;

or Q is selected from the group consisting of (U-1) to (U-61), (U-81) to (U-87), (U-89) to (U-103) and (U-105) to (U-123).

Even more preferably, Q is
$C_1$-$C_6$-alkyl, $C_1$-$C_6$-haloalkyl or $C_3$-$C_7$-cycloalkyl;
or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently
H, $C_1$-$C_4$-alkyl or $C_1$-$C_4$-haloalkyl;
or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently
H, $C_1$-$C_4$-alkyl or $C_1$-$C_4$-haloalkyl.
Especially preferably, each $R^4$ is independently methyl, ethyl, propyl, isopropyl, difluoromethyl or trifluoromethyl.
Each $R^{4a}$ preferably is independently
H, $C_1$-$C_6$-alkyl or $C_1$-$C_6$-haloalkyl.
More preferably, each $R^{4a}$ is independently
$C_1$-$C_4$-alkyl or $C_1$-$C_4$-haloalkyl.
Especially preferably, each $R^{4a}$ is independently methyl or ethyl.
Each $R^5$ preferably is independently
H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_m R^9$.
More preferably, each $R^5$ is independently
H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$.
Especially preferably, each $R^5$ is independently
H, methyl or ethyl.
Each $R^{5a}$ preferably is independently
H or $C_1$-$C_4$-alkyl.
More preferably, each $R^{5a}$ is independently
H or $C_1$-$C_2$-alkyl.
Especially preferably, each $R^{5a}$ is independently methyl or ethyl.
Each $R^6$ preferably is independently
H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^6$ is independently
H, $C_1$-$C_4$-alkyl, $C_1$-$C_4$-haloalkyl, $C_2$-$C_4$-alkenyl or $C_2$-$C_4$-haloalkenyl;
or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.
Especially preferably, each $R^6$ is independently
H, methyl or ethyl.
Each $R^{6a}$ preferably is independently
H, $C_1$-$C_4$-alkyl, $C(O)R^{13}$ or $C(O)OR^{13}$.
More preferably, each $R^{6a}$ is independently
H or $C_1$-$C_4$-alkyl.
Especially preferably, each $R^{6a}$ is independently
H, methyl or ethyl.
Each $R^7$ preferably is independently
H, $C_1$-$C_6$-alkyl, $C_1$-$C_6$-haloalkyl, $C_2$-$C_6$-alkenyl or $C_2$-$C_6$-haloalkenyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.
Especially preferably, each $R^7$ is independently
H, methyl, ethyl or trifluoromethyl.
Each $R^{7a}$ preferably is independently
$C_1$-$C_4$-alkyl or $C_1$-$C_4$-haloalkyl.
More preferably, each $R^{7a}$ is independently
$C_1$-$C_4$-alkyl or $C_1$-$C_2$-haloalkyl.
Especially preferably, each $R^{7a}$ is independently methyl or ethyl.
Each $R^8$ preferably is independently
H, $C_1$-$C_4$-alkyl or $C_1$-$C_4$-haloalkyl.
More preferably, each $R^8$ is independently
$C_1$-$C_2$-alkyl or $C_1$-$C_2$-haloalkyl.
Especially preferably, each $R^8$ is independently methyl or ethyl.
Each $R^{8a}$ preferably is independently
$C_1$-$C_4$-alkyl or $C_1$-$C_4$-haloalkyl.
More preferably, each $R^{8a}$ is independently
$C_1$-$C_4$-alkyl.
Especially preferably, each $R^{8a}$ is independently methyl or ethyl.
Each $R^9$ preferably is independently
$C_1$-$C_4$-alkyl or $C_1$-$C_4$-haloalkyl.
More preferably, each $R^9$ is independently
$C_1$-$C_2$-alkyl, $C_1$-$C_2$-haloalkyl.
Especially preferably, each $R^9$ is independently methyl, ethyl or trifluoromethyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{10}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.

Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently methyl.

Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$; or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ or $S(O)_2NR^{11}R^{12}$; or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2NR^{11}R^{12}$;
Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_m R^9$ and $S(O)_2NR^{11}R^{12}$.
More preferably, each $R^{15}$ is independently
$C_1$-$C_4$-alkyl or $C_1$-$C_4$-haloalkyl.
Especially preferably, each $R^{15}$ is independently methyl.

n preferably is 1, 2, 3 or 4. More preferably, n is 1, 2 or 3. Especially preferably, n is 1 or 2.
m preferably is 0, 1 or 2. More preferably, m is 0, 1 or 2. Especially preferably, m is 0 or 2.
X preferably is O or S. Especially preferably X is O.
Z preferably is O or S. Especially preferably Z is O.
In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

More preferably, each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently
fluor, chlor, methoxy, trifluoromethyl, trifluoromethoxy or methyl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

Embodiment 6

The compounds of the invention are defined in general terms by the formula (I). In another preferred embodiment, the compounds of the invention are defined by formula (If):

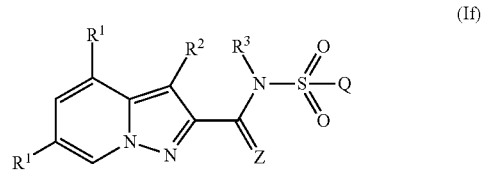

(If)

wherein
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, $R^v$, r, X, m and n are as defined above in the Summary of the Invention.

$R^1$ preferably is
H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, $R^1$ is
halogen, cyano, $OR^4$, $C_1$-$C_4$-alkyl, $C_1$-$C_4$-haloalkyl;
or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

Especially preferably, $R^1$ is
chlorine or trifluoromethyl.

$R^2$ preferably is
H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is
H, halogen, cyano, $S(O)_mR^9$ or $S(O)_2NR^{11}R^{12}$;
or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_mR^9$.

Especially preferably, $R^2$ is hydrogen.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is H, $C_1$-$C_4$-alkyl, $C_2$-$C_3$-alkenyl, $C(X)R^7$ or $C(O)OR^8$;

or $C_1$-$C_2$-alkyl substituted with $OR^4$;

or $C_1$-$C_2$-alkyl substituted with phenyl.

Especially preferably, $R^3$ is hydrogen.

Q preferably is $C_1$-$C_6$-alkyl, $C_1$-$C_6$-haloalkyl, $C_2$-$C_6$-alkenyl, $C_2$-$C_6$-haloalkenyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

or Q is selected from the group consisting of (U-1) to (U-61), (U-81) to (U-87), (U-89) to (U-103) and (U-105) to (U-123).

More preferably, Q is $C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;

or Q is selected from the group consisting of (U-1) to (U-61), (U-81) to (U-87), (U-89) to (U-103) and (U-105) to (U-123).

Even more preferably, Q is $C_1$-$C_6$-alkyl, $C_1$-$C_6$-haloalkyl or $C_3$-$C_7$-cycloalkyl;

or Q is selected from the group consisting of (U-1) to (U-61) and (U-103).

Especially preferably, Q is methyl, ethyl or cyclopropyl or is selected from the group consisting of (U-1), (U-49) and (U-103), particularly (U-1).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is independently methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_mR^{9a}$.

More preferably, each $R^5$ is independently

H, $C_1$-$C_4$-alkyl, $C_1$—$C$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$.

Especially preferably, each $R^5$ is independently

H, methyl or ethyl.

Each $R^{5a}$ preferably is independently

H or $C_1$-$C_1$-alkyl.

More preferably, each $R^{5a}$ is independently

H or $C_1$-$C_2$-alkyl.

Especially preferably, each $R^{5a}$ is independently methyl or ethyl.

Each $R^6$ preferably is independently

H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^6$ is independently

H, $C_1$-$C_4$-alkyl, $C_1$-$C_4$-haloalkyl, $C_2$-$C_4$-alkenyl or $C_2$-$C_4$-haloalkenyl;

or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently

H, methyl or ethyl.

Each $R^{6a}$ preferably is independently

H, $C_1$-$C_4$-alkyl, $C(O)R^{13}$ or $C(O)OR^{13}$.

More preferably, each $R^{6a}$ is independently

H or $C_1$-$C_4$-alkyl.

Especially preferably, each $R^{6a}$ is independently

H, methyl or ethyl.

Each $R^7$ preferably is independently

H, $C_1$-$C_6$-alkyl, $C_1$-$C_6$-haloalkyl, $C_2$-$C_6$-alkenyl or $C_2$-$C_6$-haloalkenyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^7$ is independently

H, $C_1$-$C_4$-alkyl or $C_1$-$C_4$-haloalkyl;

or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently

H, methyl, ethyl or trifluoromethyl.

Each $R^{7a}$ preferably is independently $C_1$-$C_4$-alkyl or $C_1$-$C_4$-haloalkyl.

More preferably, each $R^{7a}$ is independently
$C_1$-$C_4$-alkyl or $C_1$-$C_2$-haloalkyl.
Especially preferably, each $R^{7a}$ is independently
methyl or ethyl.
Each $R^8$ preferably is independently
H, $C_1$-$C_4$-alkyl or $C_1$-$C_4$-haloalkyl.
More preferably, each $R^8$ is independently
$C_1$-$C_2$-alkyl or $C_1$-$C_2$-haloalkyl.
Especially preferably, each $R^8$ is independently
methyl or ethyl.
Each $R^{8a}$ preferably is independently
$C_1$-$C_4$-alkyl or $C_1$-$C_4$-haloalkyl.
More preferably, each $R^{8a}$ is independently
$C_1$-$C_4$-alkyl.
Especially preferably, each $R^{8a}$ is independently
methyl or ethyl.
Each $R^9$ preferably is independently
$C_1$-$C_4$-alkyl or $C_1$-$C_4$-haloalkyl.
More preferably, each $R^9$ is independently
$C_1$-$C_2$-alkyl, $C_1$-$C_2$-haloalkyl.
Especially preferably, each $R^9$ is independently
methyl, ethyl or trifluoromethyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently
methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{10}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.
Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ or $S(O)_2 NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2 NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2 NR^{11}R^{12}$;
Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_m R^9$ and $S(O)_2 NR^{11}R^{12}$.
More preferably, each $R^{15}$ is independently
$C_1$-$C_4$-alkyl or $C_1$-$C_4$-haloalkyl.
Especially preferably, each $R^{15}$ is independently
methyl.
n preferably is 1, 2, 3 or 4. More preferably, n is 1, 2 or 3. Especially preferably, n is 1 or 2.
m preferably is 0, 1 or 2. More preferably, m is 0, 1 or 2. Especially preferably, m is 0 or 2.
X preferably is O or S. Especially preferably X is O.
Z preferably is O or S. Especially preferably Z is O.
In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $N(R^{10})C(O)R^7$. $N(R^{10})C(O)NR^{11}R^{12}$, $N(R^{10})S(O)_2R^9$, $N(R^{10})S(O)_2NR^{11}R^{12}$;

$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

More preferably, each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$.

Especially preferably, each $R^v$ is independently fluor, chlor, methoxy, trifluoromethyl, trifluoromethoxy or methyl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 0, 1, 2 or 3. Especially preferably, r is 1, 2 or 3.

A specific aspect of the compounds of this embodiment are compounds which are represented by formula (If-1)

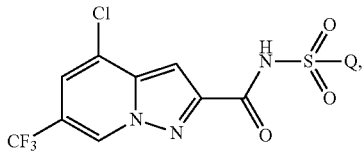

(If-1)

wherein the structural elements are defined as given above for embodiment 6.

The definitions of radicals, and explanations, that are given above in general or in ranges of preference may be combined arbitrarily with one another, thus including combinations between the respective ranges and ranges of preference. The definitions and explanations apply to the end products and also to the precursors and intermediates accordingly.

Preferred in accordance with the invention are the compounds of the formula (I) in which each structural element is defined as given above as being preferred ("preferably"). For those structural elements lacking the preferred definition, the definition in the summary of the invention shall apply.

Likewise preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (I) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (I) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (I) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (I) in which each structural element is defined as given above as being especially preferred (especially preferably). For those structural elements lacking the especially preferred definition, the definition in the summary of the invention shall apply.

Likewise especially preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 1 as defined above, the following applies:

Preferred in accordance with the invention are the compounds of the formula (Ia) in which each structural element is defined as given above as being preferred ("preferably"). For those structural elements lacking the preferred definition, the definition in the summary of the invention shall apply.

Likewise preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ia) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ia) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ia) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ia) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 2 as defined above, the following applies:

Preferred in accordance with the invention are the compounds of the formula (Ib) in which each structural element is defined as given above as being preferred ("preferably"). For those structural elements lacking the preferred definition, the definition in the summary of the invention shall apply.

Likewise preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ib) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ib) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ib) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ib) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 3 as defined above, the following applies:

Preferred in accordance with the invention are the compounds of the formula (Ic) in which each structural element is defined as given above as being preferred ("preferably"). For those structural elements lacking the preferred definition, the definition in the summary of the invention shall apply.

Likewise preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ic) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ic) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ic) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ic) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 4 as defined above, the following applies:

Preferred in accordance with the invention are the compounds of the formula (Id) in which each structural element is defined as given above as being preferred ("preferably"). For those structural elements lacking the preferred definition, the definition in the summary of the invention shall apply.

Likewise preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Id) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Id) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Id) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Id) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 5 as defined above, the following applies:

Preferred in accordance with the invention are the compounds of the formula (Ie) in which each structural element is defined as given above as being preferred ("preferably").

For those structural elements lacking the preferred definition, the definition in the summary of the invention shall apply.

Likewise preferred in accordance with the invention are the compounds of the formula (Ie) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ie) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ie) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ie) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ie) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ie) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ie) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ie) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ie) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 6 as defined above, the following applies:

Preferred in accordance with the invention are the compounds of the formula (If) in which each structural element is defined as given above as being preferred ("preferably"). For those structural elements lacking the preferred definition, the definition in the summary of the invention shall apply.

Likewise preferred in accordance with the invention are the compounds of the formula (If) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (If) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (If) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (If) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (If) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (If) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (If) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (If) in which each structural element is defined as given above as being especially preferred (especially preferably). For those structural elements lacking the especially preferred definition, the definition in the summary of the invention shall apply.

Likewise especially preferred in accordance with the invention are the compounds of the formula (If) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to compounds of formula (Ia-1) as defined above, the following applies:

Preferred in accordance with the invention are the compounds of the formula (Ia-1) in which each structural element is defined as given above as being preferred ("preferably"). For those structural elements lacking the preferred definition, the definition in the summary of the invention shall apply.

Likewise preferred in accordance with the invention are the compounds of the formula (Ia-1) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ia-1) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ia-1) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ia-1) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ia-1) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ia-1) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ia-1) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ia-1) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ia-1) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to compounds of formula (Ib-1) as defined above, the following applies:

Preferred in accordance with the invention are the compounds of the formula (Ib-1) in which each structural element is defined as given above as being preferred ("preferably"). For those structural elements lacking the preferred definition, the definition in the summary of the invention shall apply.

Likewise preferred in accordance with the invention are the compounds of the formula (Ib-1) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ib-1) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ib-1) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ib-1) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ib-1) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ib-1) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ib-1) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ib-1) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ib-1) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to compounds of formula (If-1) as defined above, the following applies:

Preferred in accordance with the invention are the compounds of the formula (If-1) in which each structural element is defined as given above as being preferred ("preferably"). For those structural elements lacking the preferred definition, the definition in the summary of the invention shall apply.

Likewise preferred in accordance with the invention are the compounds of the formula (If-1) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (If-1) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (If-1) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (If-1) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (If-1) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (If-1) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (If-1) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (If-1) in which each structural element is defined as given above as being especially preferred (especially preferably). For those structural elements lacking the especially preferred definition, the definition in the summary of the invention shall apply.

Likewise especially preferred in accordance with the invention are the compounds of the formula (If-1) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

Saturated or unsaturated hydrocarbon radicals such as alkyl, alkanediyl or alkenyl may in each case, both alone and in conjunction with heteroatoms, as in alkoxy, for example, be—where possible—either straight-chain or branched.

Any substituted radicals may, unless indicated otherwise, be substituted one or more times, and the substituents in the case of multiple substitutions may be alike or different.

In the definitions of radicals that are stated as being preferred, halogen (halo) is fluoro, chloro, bromo and iodo, very preferably fluoro, chloro and bromo, and especially preferably fluoro and chloro.

Further specific embodiments of the invention are described hereafter:

A specific embodiment of the invention are the compounds of the formula (Ia) in which Z is O;

X is O;

Q is selected from the group consisting of cyclopropyl and (U-1);

each m is independently 0 or 2;

$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 1.

A specific embodiment of the invention are the compounds of the formula (Ia) in which Z is O;

X is O;

Q is selected from the group consisting of cyclopropyl and (U-1);
each m is independently 0 or 2;
$R^1$, $R^2$, $R^3$, $R^4$, $R^7$, $R^8$, $R^9$, $R^{11}$, $R^{12}$, $R^v$ and r are as defined as being more preferred ("more preferably") in embodiment 1.

A specific embodiment of the invention are the compounds of the formula (Ia) in which
Z is O;
Q is selected from the group consisting of cyclopropyl and (U-1);
$R^1$, $R^2$, $R^3$, $R^4$, $R^v$ and r are as defined as being especially preferred ("especially preferably") in embodiment 1.

A specific embodiment of the invention are the compounds of the formula (Ia) in which
Z is O;
X is O;
Q is selected from the group consisting of cyclopropyl and (U-1);
each m is independently 0 or 2;
$R^v$ is chlor or methoxy;
r is 1 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$ and $R^{15}$ are as defined as preferred ("preferably") in embodiment 1.

A specific embodiment of the invention are the compounds of the formula (Ia) in which
Z is O;
X is O;
Q is selected from the group consisting of cyclopropyl and (U-1);
each m is independently 0 or 2;
$R^1$ is chlor or methoxy;
r is 1 or 2;
$R^1$, $R^2$, $R^3$, $R^4$, $R^7$, $R^8$, $R^9$, $R^{11}$ and $R^{12}$ are as defined as being more preferred ("more preferably") in embodiment 1.

A specific embodiment of the invention are the compounds of the formula (Ia) in which
Z is O;
Q is selected from the group consisting of cyclopropyl and (U-1);
$R^1$ is chlor or methoxy;
r is 1 or 2;
$R^1$, $R^2$, $R^3$ and $R^4$ are as defined as being especially preferred ("especially preferably") in embodiment 1.

A specific embodiment of the invention are the compounds of the formula (Ib) in which
Z is O;
X is O;
Q is selected from the group consisting of methyl, ethyl, cyclopropyl and (U-1);
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 2.

A specific embodiment of the invention are the compounds of the formula (Ib) in which
Z is O;
X is O;
Q is selected from the group consisting of methyl, ethyl, cyclopropyl and (U-1);
each m is independently 0 or 2;
$R^1$, $R^2$, $R^3$, $R^4$, $R^7$, $R^8$, $R^9$, $R^{11}$, $R^{12}$, $R^v$ and r are as defined as being more preferred ("more preferably") in embodiment 2.

A specific embodiment of the invention are the compounds of the formula (Ib) in which
Z is O;
Q is selected from the group consisting of methyl, ethyl, cyclopropyl and (U-1);
$R^1$, $R^2$, $R^3$, $R^4$, R and r are as defined as especially preferred ("especially preferably") in embodiment 2.

A specific embodiment of the invention are the compounds of the formula (Ib) in which
Z is O;
X is O;
Q is selected from the group consisting of methyl, ethyl, cyclopropyl and (U-1);
each m is independently 0 or 2;
$R^1$ is fluor, chlor or methoxy;
r is 1 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$ and $R^{15}$ are as defined as preferred ("preferably") in embodiment 2.

A specific embodiment of the invention are the compounds of the formula (Ib) in which
Z is O;
X is O;
Q is selected from the group consisting of methyl, ethyl, cyclopropyl and (U-1);
each m is independently 0 or 2;
$R^v$ is fluor, chlor or methoxy;
r is 1 or 2;
$R^1$, $R^2$, $R^3$, $R^4$, $R^7$, $R^8$, $R^9$, $R^{11}$ and $R^{12}$ are as defined as being more preferred ("more preferably") in embodiment 2.

A specific embodiment of the invention are the compounds of the formula (Ib) in which
Z is O;
Q is selected from the group consisting of methyl, ethyl, cyclopropyl and (U-1);
$R^1$ is fluor, chlor or methoxy;
r is 1 or 2;
$R^1$, $R^2$, $R^3$ and $R^4$ are as defined as being especially preferred ("especially preferably") in embodiment 2.

A specific embodiment of the invention are the compounds of the formula (If) in which
Z is O;
X is O;
Q is selected from the group consisting of methyl, ethyl, cyclopropyl, (U-1), (U-49) and (U-103);
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 6.

A specific embodiment of the invention are the compounds of the formula (If) in which
Z is O;
X is O;
Q is selected from the group consisting of methyl, ethyl, cyclopropyl, (U-1), (U-49) and (U-103);
each m is independently 0 or 2;
$R^1$, $R^2$, $R^3$, $R^4$, $R^7$, $R^8$, $R^9$, $R^{11}$, $R^{12}$, $R^v$ and r are as defined as being more preferred ("more preferably") in embodiment 6.

A specific embodiment of the invention are the compounds of the formula (If) in which
Z is O;
Q is selected from the group consisting of methyl, ethyl, cyclopropyl, (U-1), (U-49) and (U-103);
$R^1$, $R^2$, $R^3$, $R^4$, $R^v$ and r are as defined as being especially preferred ("especially preferably") in embodiment 6.

A specific embodiment of the invention are the compounds of the formula (If) in which Z is O;
X is O;
Q is selected from the group consisting of methyl, ethyl, cyclopropyl, (U-1), (U-49) and (U-103);
each m is independently 0 or 2;
$R^1$ is fluor, chlor, methoxy, trifluoromethoxy, methyl or trifluoromethyl;
r is 1, 2 or 3;
$R^1, R^2, R^3, R^4, R^{4a}, R^5, R^{5a}, R^6, R^{6a}, R^7, R^{7a}, R^8, R^{8a}, R^9, R^{9a}, R^{10}, R^{11}, R^{11a}, R^{12}, R^{13}, R^{14}$ and $R^{15}$ are as defined as preferred ("preferably") in embodiment 6.

A specific embodiment of the invention are the compounds of the formula (If) in which Z is O;
X is O;
Q is selected from the group consisting of methyl, ethyl, cyclopropyl, (U-1), (U-49) and (U-103);
each m is independently 0 or 2;
$R^1$ is fluor, chlor, methoxy, trifluoromethoxy, methyl or trifluoromethyl;
r is 1, 2 or 3;
$R^1, R^2, R^3, R^4, R^7, R^8, R^9, R^{11}$ and $R^{12}$ are as defined as being more preferred ("more preferably") in embodiment 6.

A specific embodiment of the invention are the compounds of the formula (If) in which Z is O;
Q is selected from the group consisting of methyl, ethyl, cyclopropyl, (U-1), (U-49) and (U-103);
$R^1$ is fluor, chlor, methoxy, trifluoromethoxy, methyl or trifluoromethyl;
r is 1, 2 or 3;
$R^1, R^2, R^3$ and $R^4$ are as defined as being especially preferred ("especially preferably") in embodiment 6.

Procedures and Methods

One or more of the following methods and variations as described in Schemes 1-8 can be used to prepare the compounds of formula (I). The definitions of Z, Q, n, $R^1, R^2$ and $R^3$ in the compounds of formulae (IA), (IB), (IC) and (II)-(XIII) below are as defined above in the Summary of the Invention unless otherwise noted. Formulae (IA)-(IC) are various subsets of formula (I), and all substituents for formulae (IA)-(IC) are as defined above for formula (I) unless otherwise noted. Room temperature is between about 20 and 25° C.

Compounds of formula (IA) (i.e. formula (I) wherein Z is oxygen and $R^3$ is H) can be prepared by the reaction of carboxylic acids of formula (II) with aryl or heteroaryl sulfonamides of formula (IIIA) as shown in Scheme 1. Typically, an amide coupling reagent and a catalyst such as N,N-dimethylaminopyridine (DMAP) are used in the method of Scheme 1. Amide coupling reagents include 1-ethyl-3-(3-dimethylaminopropyl)-carbodiimide hydrochloride (EDC), N,N'-dicyclohexylcarbodiimide (DCC) and 1,1'-carbonyldiimidazole (CDI). The reaction can be carried out at temperatures ranging from room temperature to the reflux temperature of the solvent. Typical solvents include alcohols, ethers, esters, amides and halogenated hydrocarbons. Synthesis Example 1 describes a particularly useful set of conditions utilizing EDC/DMAP in dichloromethane.

Scheme 1:

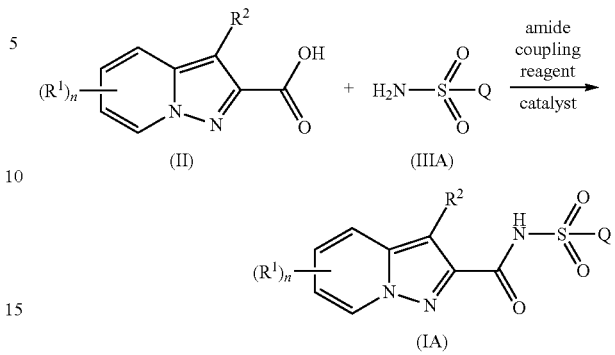

Compounds of formula (IA) can also be prepared by the reaction of carboxylic acid chlorides of formula (IV) with aryl or heteroaryl sulfonamides of formula (IIIA) as shown in Scheme 2. The reaction typically involves use of a base such as triethylamine or pyridine and optionally a catalyst such as DMAP in the presence of a solvent. The reaction can be carried out at temperatures ranging from room temperature to the reflux temperature of the solvent. Typical solvents include ethers, esters and halogenated hydrocarbons.

Scheme 2:

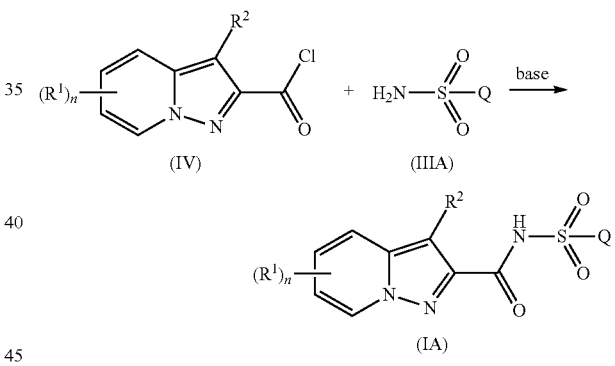

Compounds of formula (IB) wherein $R^3$ is optionally substituted alkyl, alkenyl, alkynyl or cycloalkylalkyl and Z is oxygen can be prepared by the reaction of compounds of formula (IA) with appropriately substituted alkyl, alkenyl, alkynyl or cycloalkylalkyl halides and base as shown in Scheme 3. Typical reaction conditions comprise potassium carbonate as the base and DMF as the solvent.

Scheme 3:

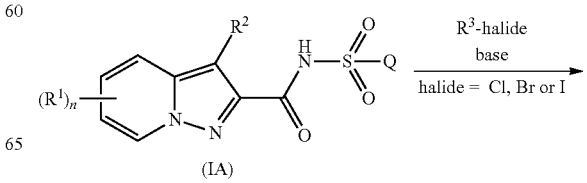

-continued

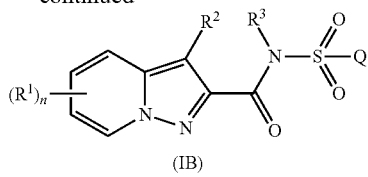

(IB)

Compounds of formula (IB) wherein $R^3$ is $C(X)R^7$, $C(O)OR^8$, $C(O)NR^{11}R^{12}$, $S(O)_2R^9$ or $S(O)_2NR^{11}R^{12}$ can be prepared by the reaction of compounds of formula (IA) with acyl or sulfonyl halides (e.g., Cl—$C(X)R^7$, Cl—$C(O)OR^8$, Cl—$C(O)NR^{11}R^{12}$, Cl—$S(O)_2R^9$ or Cl—$S(O)_2NR^{11}R^{12}$) by acylation or sulfonylation methods well known in the art.

Compounds of formula (IB) wherein $R^3$ is optionally substituted alkyl, alkenyl, alkynyl, cycloalkyl or phenyl can be prepared by the reaction of acid chlorides of formula (IV) with sulfonamides of formula (IIIB) as shown in Scheme 4. Alternatively, compounds of formula (IB) wherein $R^3$ is optionally substituted alkyl, alkenyl, alkynyl, cycloalkyl or phenyl can be prepared by the reaction of carboxylic acids of formula (II) with sulfonamides of formula (IIIB) by the method of Scheme 1.

Scheme 4:

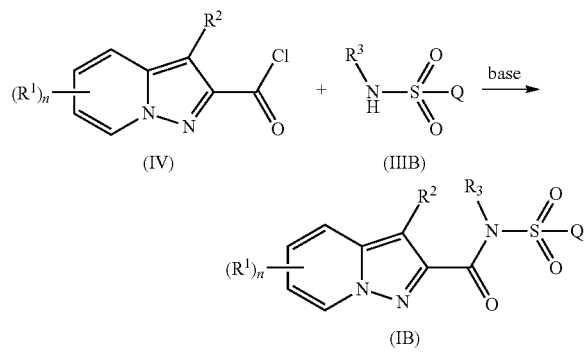

$R^3$ is optionally substituted alkyl, alkenyl, alkynyl, cycloalkyl or phenyl

Thioamides of formula (IC) (i.e. formula (I) wherein Z is sulfur) can be prepared by the reaction of compounds of formula (IA) or (IB) (i.e. formula (I) wherein Z is oxygen) with thiation reagents such as phosphorus pentasulfide or Lawesson's reagent as depicted in Scheme 5.

Scheme 5:

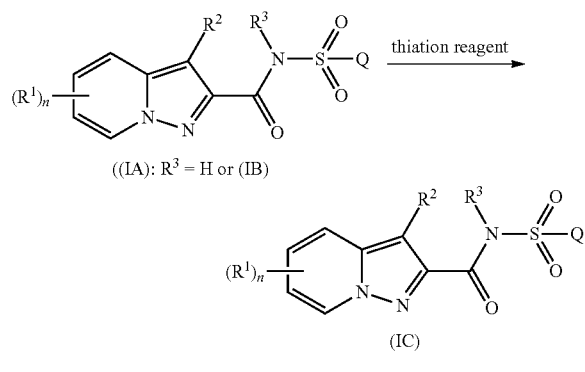

Compounds of formula (IIB) (i.e. formula (II) wherein $R^2$ is bromine) can be prepared by the reaction of compounds of formula (IIA) (i.e. formula (II) wherein $R^2$ is H) with 1,2-dibromotetrachloroethane in tetrahydrofurane in the presence of n-butyl-Li as described in WO 2009/023179.

Scheme 6:

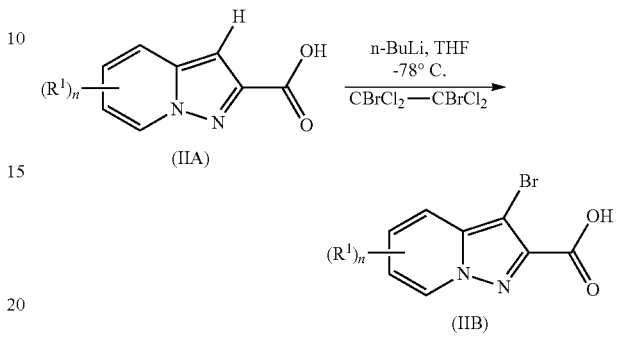

Compounds of formula (II) wherein $R^2$ is cyano can be prepared by reaction of compounds of formula (IIB) with CuCN by methods known in the art. Compounds of formula (II) wherein $R^2$ is nitro can be prepared by reaction of compounds of formula (IIA) by methods known in the art with nitric acid/sulfuric acid (cf. Chinese Journal of Chemistry 25, 241-245 (2007), WO 2009/023179). Compounds of formula (II) wherein $R^2$ is $OR^4$, $NR^5R^6$ or $SR^9$ can be prepared from compounds of formula (II) wherein $R^2$ is halogen by standard displacement reactions well known in the art (cf. WO 2009/023179). Compounds of formula (II) wherein $R^2$ is F can be prepared by methods known in the art (cf. WO 2002/008224).

Carboxylic acids of formula (II) and acid chlorides of Formula (IV) can be prepared by the reactions shown in Scheme 7. Reaction of a suitably substituted pyridine of formula (V) with an aminating agent of formula (VI) at temperatures ranging from room temperature to the boiling temperature of the solvent like methylene chloride or chloroform affords the N-amino-pyridinium salt of formula (VII) (see, for example, Chemistry,—A European Journal 1, 557-563 (1995)). Treatment of salt (VII) with acetylene dicarboxylic acid dialkyl ester an inert solvent such as dimethylformamide in the presence of a base like potassium carbonate results in formation of diester (VIII) (cf. WO 2008/124153). Reaction of (VIII) with aqueous sulfuric acid affords the carboxylic acid (IIA). The carboxylic acid of formula (IIA) can be converted to the acid chloride of formula (IVA) by well-known conventional means such as treatment with thionyl chloride or oxalyl chloride with a catalytic amount of N,N-dimethylformamide (DMF) in moderately polar, aprotic solvents including dichloromethane, dichloroethane, toluene and ethyl acetate. Intermediates of formula (VI) can be prepared by a variety of well-known synthetic methods (cf. Chemistry—A European Journal 1, 557-563 (1995) and WO 2011/112186).

Scheme 7:

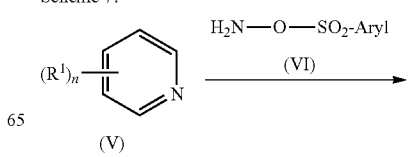

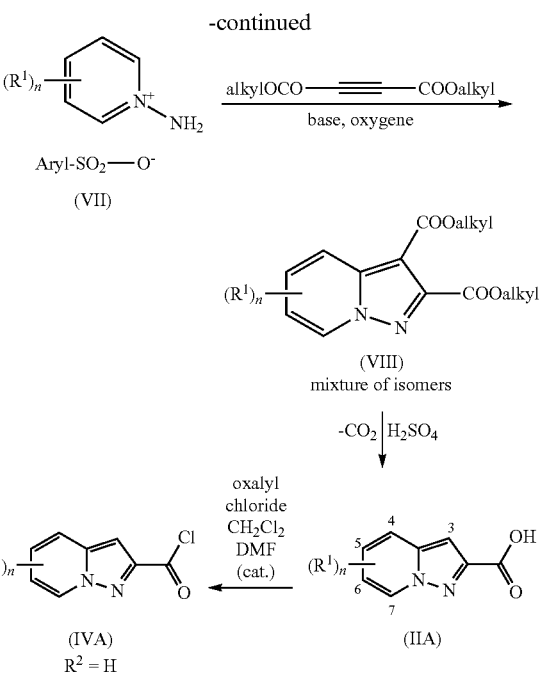

Examples for intermediates of formula (II) or (VIII) are in several cases commercially available ("Comm. av.") or can be prepared according to well-known procedures, for example as indicated in table 1.

TABLE 1

| $R^1$ | n | $R^2$ | alkyl | intermediate | remarks |
|---|---|---|---|---|---|
| 6-Br | 1 | COOMe | Me | (VIII) | Comm. av. |
| 7-OMe | 1 | COOMe | Me | (VIII) | Comm. av. |
| 4-Br | 1 | COOMe | Me | (VIII) | Comm. av. |
| 7-CF$_3$ | 1 | COOMe | Me | (VIII) | Comm. av. |
| 4-Me | 1 | H | — | (IIA) | Comm. av. |
| 5-Me | 1 | H | — | (IIA) | Comm. av. |
| 6-Me | 1 | H | — | (IIA) | Comm. av. |
| 7-Me | 1 | H | — | (IIA) | Comm. av. |
| 6-Br | 1 | H | — | (IIA) | Comm. av. |
| 6-F | 1 | H | — | (IIA) | Comm. av. |
| 6-Cl | 1 | H | — | (IIA) | Comm. av. |
| 5-Br | 1 | H | — | (IIA) | Comm. av. |
| 5-F | 1 | H | — | (IIA) | Comm. av. |
| 5-Cl | 1 | H | — | (IIA) | Comm. av. |
| 7-Br | 1 | H | — | (IIA) | Comm. av. |
| 7-F | 1 | H | — | (IIA) | Comm. av. |
| 4-F | 1 | H | — | (IIA) | Comm. av. |
| 4-Br | 1 | H | — | (IIA) | Comm. av. |
| 6-Me | 1 | Br | — | (IIB) | Comm. av. |
| 6-Br | 1 | Cl | — | (II) | Comm. av. |
| 5-CF$_3$ | 1 | H | — | (IIA) | Comm. av. |
| 4-Br, 6-Br | 2 | H | — | (IIA) | Comm. av. |
| 4-Me, 6-Br | 2 | H | — | (IIA) | Comm. av. |
| 5-Br, 7-CF$_3$ | 2 | H | — | (IIA) | Comm. av. |
| 5-OMe, 7-CF$_3$ | 2 | H | — | (IIA) | Comm. av. |
| 5-Cl, 7-CF$_3$ | 2 | Cl | — | (II) | Comm. av. |

Sulfonamides of formulae (IIIA) and (IIIB) are known in the chemical literature or are available commercially. As shown in Scheme 8, sulfonamides of formula (IIIA) are readily prepared from the corresponding sulfonyl chlorides of formula (IX) by reaction with ammonia, while sulfonamides of formula (IIIB) are readily prepared from the corresponding sulfonyl chlorides of formula (IX) by reaction with $R^3NH_2$. The sulfonyl chloride intermediates are available commercially or can be prepared by a large variety of methods known in the literature. Three of the most common methods of sulfonyl chloride preparation are shown in Scheme 8, including (a) direct chlorosulfonylation of aromatic and heteroaromatic systems with chlorosulfonic acid, (b) oxidation of sulfides (for example with sodium hypochlorite) in the presence of hydrochloric acid, and (c) diazotization and chlorosulfonylation of aromatic and heteroaromatic amines. These three methods are meant only to be illustrative; a large variety of other synthetic methods are available for the preparation of sulfonyl chlorides and sulfonamides.

Scheme 8:

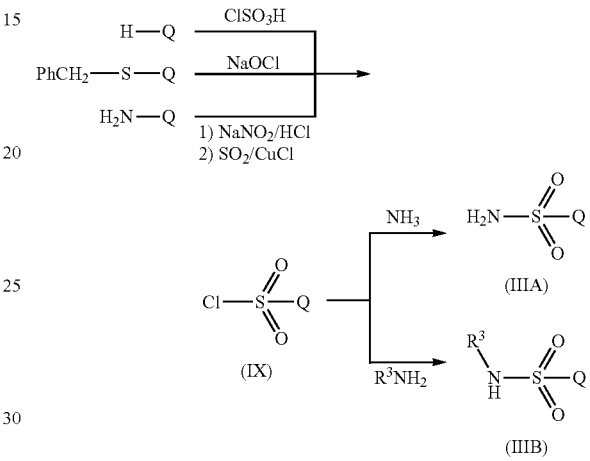

Pyridines of general formula (V) or their salts with organic or inorganic acids like hydrochloric acid are known in the chemical literature or are available commercially.

The compound according to the present invention can be prepared according to the processes described above. It will nevertheless be understood that, on the basis of his general knowledge and of available publications, the skilled worker will be able to adapt this method according to the specifics of each of the compounds, which it is desired to synthesize.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded herefrom are methods for the surgical or therapeutic treatment of the human or animal body and diagnostic methods carried out on the human or animal body.

The invention furthermore relates to the use of the compounds of the formula (I) as pesticides, in particular crop protection agents.

In the context of the present application, the term "pesticide" in each case also always comprises the term "crop protection agent".

The compounds of the formula (I), having good plant tolerance, favourable homeotherm toxicity and good environmental compatibility, are suitable for protecting plants and plant organs against biotic and abiotic stressors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and against all or some stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;

from the order or the class of the Collembola, for example *Onychiurus armatus; Sminthurus viridis*;

from the class of the Diplopoda, for example *Blaniulus guttulatus*;

from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa*; from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris cacrulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricome, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calli-*

*phora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex*;

from the order of the Hemiptera, for example *Acizzia acaciaebaileyanae, Acizzia dodonaeae, Acizzia uncatoides, Acrida turrita, Acyrthosiphon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus vibumi, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplo-*

*campa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platylminthes and Nematoda, for example *Aelurostrongylus* spp., *Amidostomum* spp., *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp.,

*Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, in particular *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivius*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

Furthermore, it is possible to control, from the subkingdom of the Protozoa, the order of the Coccidia, for example *Eimeria* spp.

Nematodes

In the present context, the term "nematodes" comprises all species of the phylum Nematoda and here in particular species acting as parasites on plants or fungi (for example species of the order Aphelenchida, Meloidogyne, Tylenchida and others) or else on humans and animals (for example species of the orders Trichinellida, Tylenchida, Rhabditina and Spirurida) and causing damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per soil volume, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, particularly preferably 51-79% and very particularly preferably the complete kill or the complete prevention of development and growth of the nematodes by a reduction of 80 to 100%. The control of nematodes as described herein also comprises the control of proliferation of the nematodes (development of cysts and/or eggs). Compounds of the formula (I) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp., *Criconemoides ferniae*, *Criconemoides onoense*, *Criconemoides ornatum* and *Criconemoides* spp., *Ditylenchus destructor*, *Ditylenchus dipsaci*, *Ditylenchus myceliophagus* and also the stem and leaf endoparasites *Ditylenchus* spp., *Dolichodorus heterocephalus*, *Globodera pallida* (=*Heterodera pallida*), *Globodera rostochiensis* (yellow potato cyst nematode), *Globodera solanacearum*, *Globodera tabacum*, *Globodera virginia* and the non-migratory cyst-forming parasites *Globodera* spp., *Helicotylenchus digonicus*, *Helicotylenchus dihystera*, *Helicotylenchus erythrine*, *Helicotylenchus multicinctus*, *Helicotylenchus nannus*, *Helicotylenchus pseudorobustus* and *Helicotylenchus* spp., *Hemicriconemoides*, *Hemicycliophora arenaria*, *Hemicycliophora nudata*, *Hemicycliophora parvana*, *Heterodera avenae*, *Heterodera cruciferae*, *Heterodera glycines* (soya bean cyst nematode), *Heterodera oryzae*, *Heterodera schachtii*, *Heterodera zeae* and the non-migratory cyst-forming parasites *Heterodera* spp., *Hirschmaniella gracilis*, *Hirschmaniella* oryzae, Hirschmaniella spinicaudata and the stem and leaf endoparasites Hirschmaniella spp., Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola and the ectoparasites Longidorus spp., Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi and the non-migratory parasites Meloidogyne spp., Meloinema spp., Nacobbus abcrrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres and Paratrichodorus spp., Paratylenchus hamatus, Paratylenchus minutus, Paratylenchus projectus and Paratylenchus spp., Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae and the migratory endoparasites Pratylenchus spp., Pseudohalenchus minutus, Psilenchus magnidens, Psilenchus tumidus, Punctodera chalcoensis, Quinisulcius acutus, Radopholus citrophilus, Radopholus similis, the migratory endoparasites Radopholus spp., Rotylenchulus borealis, Rotylenchulus parvus, Rotylenchulus reniformis and Rotylenchulus spp., Rotylenchus laurentinus, Rotylenchus macrodoratus, Rotylenchus robustus, Rotylenchus uniformis and Rotylenchus spp., Scutellonema brachyurum, Scutellonema bradys, Scutellonema clathricaudatum and the migratory endoparasites Scutellonema spp., Subanguina radiciola, Tetylenchus nicotianae, Trichodorus cylindricus, Trichodorus minor, Trichodorus primitivus, Trichodorus proximus, Trichodorus similis, Trichodorus sparsus and the ectoparasites Trichodorus spp., Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris and Tylenchorhynchus spp., Tylenchulus semipenetrans and the semiparasites Tylenchulus spp., Xiphinema americanum, Xiphinema brevicolle, Xiphinema dimorphicaudatum, Xiphinema index and the ectoparasites Xiphinema spp.

Nematodes for the control of which a compound of the formula (I) may be used include nematodes of the genus Meloidogyne such as the Southern root-knot nematode (Meloidogyne incognita), the Javanese root-knot nematode (Meloidogyne javanica), the Northern root-knot nematode (Meloidogyne hapla) and the peanut root-knot nematode (Meloidogyne arenaria); nematodes of the genus Ditylenchus such as the potato rot nematode (Ditylenchus destructor) and stem and bulb eelworm (Ditylenchus dipsaci); nematodes of the genus Pratylenchus such as the cob root-lesion nematode (Pratylenchus penetrans), the chrysanthemum root-lesion nematode (Pratylenchus fallax), the coffee root nematode (Pratylenchus coffeae), the tea root nematode (Pratylenchus loosi) and the walnut root-lesion nematode (Pratylenchus vulnus); nematodes of the genus Globodera such as the yellow potato cyst nematode (Globodera rostochiensis) and the white potato cyst nematode (Globodera pallida); nematodes of the genus Heterodera such as the soya bean cyst nematode (Heterodera glycines) and beet cyst eelworm (Heterodera schachtii); nematodes of the genus Aphelenchoides such as the rice white-tip nematode (Aphelenchoides besseyi), the chrysanthemum nematode (Aphelenchoides ritzemabosi) and the strawberry nematode (Aphelenchoides fragariae); nematodes of the genus Aphelenchus such as the fungivorous nematode (Aphelenchus avenae); nematodes of the genus Radopholus, such as the burrowing nematode (Radopholus similis); nematodes of the genus Tylenchulus such as the citrus root nematode (Tylenchulus semipenetrans); nematodes of the genus Rotylenchulus such as the reniform nematode (Rotylenchulus reniformis); tree-dwelling nematodes such as the pine wood nematode (Bursaphelenchus xylophilus) and the red ring nematode (Bursaphelenchus cocophilus) and the like.

Plants for the protection of which a compound of the formula (I) can be used include plants such as cereals (for example rice, barley, wheat, rye, oats, maize and the like), beans (soya bean, aduki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plant for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, water melon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular Pratylenchus brachyurus, Pratylenchus coffeae, Meloidogyne exigua, Meloidogyne incognita, Meloidogyne coffeicola, Helicotylenchus spp. and also Meloidogyne paranaensis, Rotylenchus spp., Xiphinema spp., Tylenchorhynchus spp. and Scutellonema spp.

The compounds of the formula (I) are particularly suitable for controlling potato nematodes, in particular Pratylenchus brachyurus, Pratylenchus pratensis, Pratylenchus scribneri, Pratylenchus penetrans, Pratylenchus coffeae, Ditylenchus dipsaci and of Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus

*similis, Rotylenchulus reniformis, Neotylenchus vigissi, Paraphelenchus pseudoparietinus, Aphelenchoides fragariae* and *Meloinema* spp.

The compounds of the formula (I) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei*.

The compounds of the formula (I) are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae*, (*Belonolaimus gracilis*), *Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola*.

The compounds of the formula (I) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus,* (*Belonolaimus gracilis*), *Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans*.

The compounds of the formula (I) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) are particularly suitable for controlling pineapple nematodes, in particular *Pratylenchus zeae, Pratylenchus pratensis, Pratylenchus brachyurus, Pratylenchus goodeyi, Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum*.

The compounds of the formula (I) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans*.

The compounds of the formula (I) are particularly suitable for controlling nematodes in tree crops—pome fruit, in particular *Pratylenchus penetrans* and also *Pratylenchus vulnus, Longidorus elongatus, Meloidogyne incognita* and *Meloidogyne hapla*.

The compounds of the formula (I) are particularly suitable for controlling nematodes in tree crops-stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus*.

The compounds of the formula (I) are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp, *Xiphinema* spp. and *Cacopaurus pestis*.

In the present context, the term "nematodes" also refers to nematodes damaging humans or animals.

Specific nematode species harmful to humans or to animals are:

Trichinellida, for example: *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp.;

*Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.

Many known nematicides also act against other parasitic helminths and are therefore used for controlling worms—not necessarily belonging to the group Nematoda—which are parasites in humans and animals.

The present invention also relates to the use of the compounds of the formula (I) as anthelmintic medicaments. The pathogenic endoparasitic helminths include Platyhelminthes (e.g. Monogenea, cestodes and trematodes), Acanthocephala and Pentastoma. The following helminths may be mentioned as being preferred:

Monogenea: e.g.: *Gyrodactylus* spp., *Dactylogyrus* spp., *Polystoma* spp.;

Cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the administration of the compounds of the formula (I) is carried out by methods generally known in the art, directly or enterally, parenterally, dermally or nasally in the form of suitable preparations. Administration can be carried out prophylactically or therapeutically.

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are prepared either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms is usually between 0.00000001 and 95% by weight of the compound of the formula (I), preferably between 0.00001 and 1% by weight, based on the weight of the use form. The compounds are employed in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, cyclodiene-organochlorines, for example chlordane and endosulfan or phenylpyrazoles (fiproles), for example ethiprole and fipronil.

(3) Sodium channel modulators/voltage-gated sodium channel blockers such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinergic acetylcholine receptor (nAChR) agonists, such as, for example, neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR) such as, for example, spinosyns, e.g. spinetoram and spinosad.

(6) Chloride channel activators, such as, for example, avermectins/milbemycins, for example abamectin, emamectin benzoate, lepimectin and milbemectin.

(7) Juvenile hormone imitators such as, for example, juvenile hormone analogues, e.g. hydroprene, kinoprene and methoprene or fenoxycarb or pyriproxyfen.

(8) Active compounds with unknown or nonspecific mechanisms of action such as, for example, alkyl halides, e.g. methyl bromide and other alkyl halides; or chloropicrine or sulphuryl fluoride or borax or tartar emetic.

(9) Selective antifeedants, for example pymetrozine or flonicamid.

(10) Mite growth inhibitors, for example clofentezine, hexythiazox and diflovidazin or etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron or organotin compounds, for example azocyclotin, cyhexatin and fenbutatin oxide or propargite or tetradifon;

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocylam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone or acequinocyl or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase such as, for example, tetronic and tetramic acid derivatives, e.g. spirodiclofen, spiromesifen and spirotetramat.

(24) Complex-IV electron transport inhibitors such as, for example, phosphines, e.g. aluminium phosphide, calcium phosphide, phosphine and zinc phosphide or cyanide.

(25) Complex II electron transport inhibitors, such as, for example, cyenopyrafen and cyflumetofen.

(28) Ryanodine receptor effectors, such as, for example, diamides, e.g. chlorantraniliprole, cyantraniliprole and flubendiamide, further active compounds such as, for example, afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; furthermore preparations based on *Bacillus firmus* (I-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl) pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Inhibitors of ergosterol biosynthesis such as, for example, (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) 0-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors) such as, for example, (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl) pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) acting on complex III of the respiratory chain such as, for example, (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy] methyl}phenyl)ethanamide, (3.25) (2E)-2-(methoxyimino)-N-methyl-2-{2-[(E)-({1-[3-(trifluoromethyl)phenyl] ethoxy}imino)methyl]phenyl}ethanamide, (3.26) (2E)-2-{2-[({[(1E)-1-(3-{[(E)-1-fluoro-2-phenylethenyl] oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene] amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl) phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino] methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division such as, for example, (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers such as, for example, (6.1) acibenzolar-S-methyl, (6.2) isotianil, (6.3) probenazole, (6.4) tiadinil and (6.5) laminarin.

(7) Inhibitors of amino acid and protein biosynthesis such as, for example, (7.1), (7.2) blasticidin-S, (7.3) cyprodinil, (7.4)

kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Inhibitors of cell wall synthesis such as, for example, (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Inhibitors of lipid and membrane synthesis such as, for example, (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Inhibitors of nucleic acid synthesis such as, for example, (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors such as, for example, (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers such as, for example, (14.1) binapacryl, (14.2) dinocap, (14.3) ferimzone, (14.4) fluazinam and (14.5) meptyldinocap.

(15) Further compounds such as, for example, (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7 (2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(l-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91)phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95)

1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All mixing components mentioned in classes (1) to (15) can, if they are capable on the basis of their functional groups, optionally form salts with suitable bases or acids.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as spore-forming bacteria, root-colonising bacteria and bacteria which act as biological insecticides, fungicides or nematicides.

Examples of such bacteria which are employed or can be used as biological pesticides are:
*Bacillus amyloliquefaciens*, strain FZB42 (DSM 231179), or *Bacillus cereus*, in particular *B. cereus* strain CNCM I-1562 or *Bacillus firmus*, strain I-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are employed or can be used as biological pesticides are:
*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM I-952).

Examples of viruses which are employed or can be used as biological pesticides are: *Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:
*Agrobacterium* spp., *Azorhizobium caulinodans*, *Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., in particular *Rhizobium trifolii*, *Rhizopogon* spp., *Scleroderma* spp., *Suillus* spp., *Streptomyces* spp.

Examples of plant extracts and products formed by microorganisms including proteins and secondary metabolites which are employed or can be used as biological pesticides are:
*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), Pyrethrum/Pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, in particular oilseed rape powder or mustard powder.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl) amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), furthermore increased resistance of the plants against phytopathogenic fungi, bacteria and/or viruses owing, for example, to systemic acquired resistance (SAR), systemin, phytoalexins, elicitors and also resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants. In the case of paddy rice crops, this can also be done by metering the compound of the formula (I) in a solid application form (for example as granules) into a flooded paddy field.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water to a certain stage of the rice embryo ('pigeon breast stage'), stimulating the germination and a more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions.

Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz—and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term endoparasites includes in particular helminths and protozoans, such as coccidia. Ectoparasites are typically and preferably arthropods, in particular insects and acarids.

In the field of veterinary medicine the compounds of the formula (I) are suitable, with favourable homeotherm toxicity, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffaloes, rabbits, reindeers, fallow deers, and in particular cattle and pigs; or poultry such as turkeys, ducks, geese, and in particular chickens; fish and crustaceans, for example in aquaculture; and also insects such as bees.

Domestic animals include, for example, mammals, such as hamsters, guinea pigs, rats, mice, chinchillas, ferrets and in particular dogs, cats, cage birds, reptiles, amphibians and aquarium fish.

According to a preferred embodiment, the compounds of the formula (I) are administered to mammals.

According to another preferred embodiment, the compounds of the formula (I) are administered to birds, namely cage birds and in particular poultry.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the compounds of the formula (I) are effective in reducing the incidence of the respective parasite in an animal infected with such parasites to innocuous levels. More specifically, "controlling", as used herein, means that the compound of the formula (I) is effective in killing the respective parasite, inhibiting its growth, or inhibiting its proliferation.

Arthropods include:
from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;
from the order of the Heteropterida, for example *Cimex* spp., *Triatoma* spp., *Rhodnius* spp., *Panstrongylus* spp.; as well as nuisance and hygiene pests from the order of the Blattarida.

Arthropods furthermore include:
from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi-host ticks); from the order of mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyleticlla* spp., *Ornithocheyletia* spp., *Myobia* spp., *Psorergates* spp., *Demodex* spp., *Trombicula* spp., *Neotrombicula* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa include:
Mastigophora (*Flagellata*) such as, for example, Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, such as, for example, Trichomonadidae, for example, *Giardia lamblia*, *G. canis*; Sarcomastigophora (Rhizopoda) such as Entamoebidae, for example, *Entamoeba histolytica*, Hartmanellidae, for example, *Acanthamoeba* sp., *Harmanella* sp.;
Apicomplexa (Sporozoa) such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidalcs*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, Globidium spec., *Isospora belli*, *I. canis*, *I. felis*, *I. ohioensis*, *I. rivolta*, *I. spec.*, *I. suis*, *Cystisospora* spec., *Cryptosporidium* spec., in particular *C. parvum*; such as Toxoplasmadiidae, for example, *Toxoplasma gondii*, *Hammondia heydornii*, *Neospora caninum*, *Besnoitia besnoitii*; such as Sarcocystidae, for example, *Sarcocystis bovicanis*, *S. bovihominis*, *S. ovicanis*, *S. ovifelis*, *S. neurona*, S. spec., *S. suihominis*, such as Leucozoidae, for example, *Leucozytozoon simondi*, such as Plasmodiidae, for example, *Plasmodium berghei*, *P. falciparum*, *P. malariae*, *P. ovale*, *P. vivax*, P. spec., such as Piroplasmea, for example, *Babesia argentina*, *B. bovis*, *B. canis*, B. spec., *Theileria parva*, *Theileria* spec., such as Adeleina, for example, *Hepatozoon canis*, H. spec.

Pathogenic endoparasites, which are helminths, include Platyhelmintha (e.g. Monogenea, cestodes and trematodes), nematodes, Acanthocephala, and Pentastoma, including:
Monogenea: e.g.: *Gyrodactylus* spp., *Dactylogyrus* spp., *Polystoma* spp.;
Cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.;
from the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;
Trematodes: from the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.;
Nematodes: *Trichinellida zum Beispiel: Trichuris* spp., *Capillaria* spp., *Paracapillaria* spp., *Eucoleus* spp., *Trichomosoides* spp., *Trichinella* spp.;
from the order of the Tylenchida for example: *Micronema* spp., *Strongyloides* spp.;
from the order of the Rhabditida for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Creno-*

*soma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, administration of the compounds of the formula (I) is carried out by methods generally known in the art, such as enterally, parenterally, dermally or nasally in the form of suitable preparations. Administration can be carried out prophylactically or therapeutically.

Thus, one embodiment of the present invention refers to the use of a compound of the formula (I) as medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, in particular a helminthicidal agent or antiprotozoic agent, for example in animal husbandry, in animal breeding, in animal housing and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in stables or in the hygiene sector.

Anthelmintic Mixing Components

The following anthelmintic mixing components may be mentioned by way of example:

Anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, menichlopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the sense of the present invention are insects, for example aphids, flies, leafhoppers or *thrips*, which are capable of transmitting plant viruses to plants. Other vectors capable of transmitting plant viruses are spider mites, lice, beetles and nematodes.

Further examples of vectors in the sence of the present invention are insects and arachnids such as mosquitoes, in particular of the genera *Aedes, Anopheles*, for example *A. gambiae, A. arabiensis, A. funestus, A. dirus* (malaria) and

*Culex*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids and mites encountered in enclosed spaces such as dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The various aspects of the invention will now be illustrated with reference to the following production and use examples in a non limiting manner.

PREPARATION EXAMPLES

It is recognized that some reagents and reaction conditions described above for preparing compounds of formula (I) may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M.

Protective Groups in Organic Synthesis, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of formula (I). One skilled in the art will also recognize that it may be necessary to perform a combination of the steps illustrated in the above schemes in an order other than that implied by the particular sequence presented to prepare the compounds of formula (I).

One skilled in the art will also recognize that compounds of formula (I) and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps.

$^1$H-NMR Data $^1$H-NMR-data were determined with a Bruker Avance 400 equipped with a flow cell (60 µl volume) or with a Bruker AVIII 400 equipped with 1.7 mm cryo-CPTCI probe head or with a Bruker AVII 600 (600.13 MHz) equipped with a cyroTCI probe head or with a Bruker AVIII 600 (601.6 MHz) equipped with a cryo CPMNP probe head with tetramethylsilane as reference (0.0) and the solvents $CD_3CN$, $CDCl_3$, $[D_6]$-DMSO.

$^1$H-NMR-data of selected examples are listed in classic format (chemical shift δ, multiplicity, number of hydrogen atoms) or as NMR-peak-lists.

$^1$H NMR spectra are reported in ppm downfield from tetramethylsilane.

"s" means singlet, "d" means doublet, "dd" means doublet of doublets, "t" means triplet, "q" means quartet, "br s" means broad singlet, "m" means multiplet.

NMR-Peak-Lists:

If NMR-data of selected examples are provided in form of $^1$H-NMR-peak lists, then for every peak first the chemical shift δ in ppm and then, separated by a blank, the intensity of the signal in round brackets is listed. Between the δ-value-signal intensity pairs are semicolons as delimiters.

The peak list of an example is therefore listed as: δ$_1$ (intensity$_1$); δ$_2$ (intensity$_2$); ... ; δ$_i$ (intensity$_i$); ... ; δ$_n$ (intensity$_n$).

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

The solvent, in which the NMR-spectrum was measured, is specified in squared brackets.

Synthesis Example 1

Preparation of N-[(2-chlorophenyl)sulfonyl]-5-(trifluoromethyl)pyrazolo[1,5-a]pyridine-2-carboxamide (Table 2, Example (I-1))

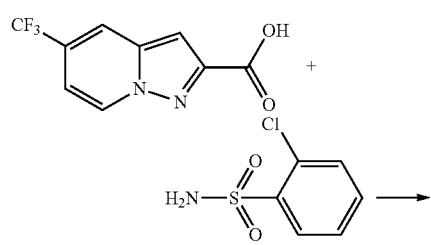

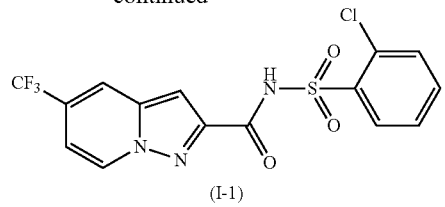

(I-1)

To 69 mg 5-(trifluoromethyl)pyrazolo[1,5-a]pyridine-2-carboxylic acid (0.30 mmol) was added a solution of 4-(dimethylamino)pyridine (110 mg, 0.90 mmol) and 1-(3-dimethyl-aminopropyl)-3-ethylcarbodiimide hydrochloride (205 mg, 0.90 mmol) in dichloromethane (9 mL). The reaction mixture was stirred for 15 min, 2-chloro-benzene-sulfonamide (57.5 mg, 0.30 mmol) was added, and the reaction mixture was stirred at room temperature overnight. Dichloromethane (50 mL) was then added, the mixture was washed with 1 N hydrochloric acid (50 mL). The aqueous phase was reextracted two times with dichloromethane, all organic phases were combined and dried over magnesium sulfate. The solvent was evaporated and the remaining solid was rinsed with diethyl ether to afford 121 mg (purity 90%, 89.7%) of the title compound, a compound of the present invention, as a colorless solid, $^1$H-NMR, Table 3.

Preparation of Intermediates of General Formula (II)

Preparation of 4-chloro-6-(trifluoromethyl)pyrazolo[1,5-a]pyridine-2-carboxylic Acid (II-1)

Step 1: Preparation of N-amino-3-chloro-5-trifluoromethyl-pyridinium p-tosylate

To a solution of 1-[(aminooxy)sulfonyl]-4-methylbenzene (15 g, 80 mmol) in dichloromethane was added 3-chloro-5-(trifluoromethyl)pyridine (9.9 g, 68 mmol), and the mixture stirred at 20° C. for 2 h. Then the solvent was removed under reduced pressure to give 7.4 g of the desired product as a white solid, which was used directly in the next step without further purification.

See FIG. 1, which depicts the $^1$H-NMR spectrum of N-amino-3-chloro-5-trifluoromethyl-pyridinium p-tosylate ([D$_6$]-DMSO, 400 MHz)

Step 2: Preparation of dimethyl 4-chloro-6-(trifluoromethyl)pyrazolo[1,5-a]pyridine-2,3-dicarboxylate (Isomer A)

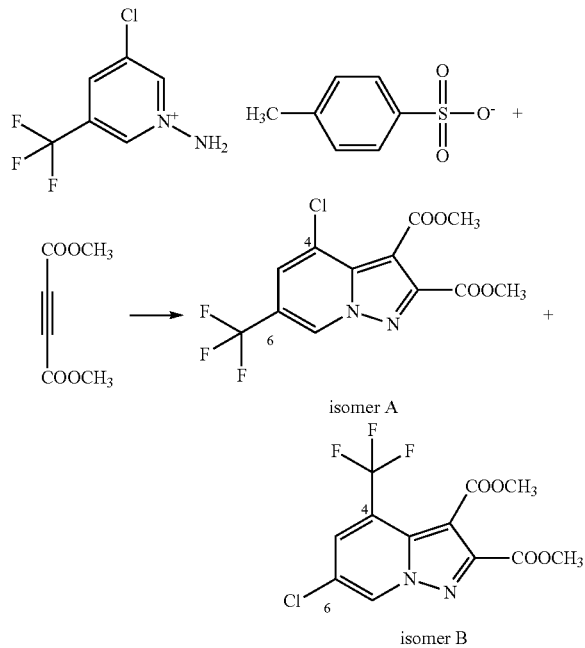

isomer A isomer B

To a solution of N-amino-3-chloro-5-trifluoromethylpyridinium p-tosylate (28.5 g, 77 mmol) in dimethylformamide (300 mL) was added dimethyl acetylenedicarboxylate (16 g, 116 mmol) and potassium carbonate (21 g, 155 mmol) at 0° C. The resulting mixture was stirred at room temperature overnight with the existence of oxygene via introducing a steam of dry air to the reaction with a pressure pump. Thin layer chromatography check showed complete consumption of the starting material, water and ethyl acetate was added to the mixture and the organic phase was separated and combined, dried over sodium sulfate, filtered, concentrated, and purified by silica gel column chromatography (n-hexane: EtOAc=6:1) to isolate the two isomers separately. Desired dimethyl 4-chloro-6-(trifluoromethyl)pyrazolo[1,5-a]pyridine-2,3-dicarboxylate (isomer A, 7.1 g) was obtained as an red solid. The structure of isomers was elucidated and characterized by $^1$H-NMR, $^{13}$C-NMR, HMBC ((Heteronuclear Multiple Bond Correlation) and HSQC (Heteronuclear Single Quantum Correlation) based on the J(C,F) coupling patterns in both isomers.

Figure 2:
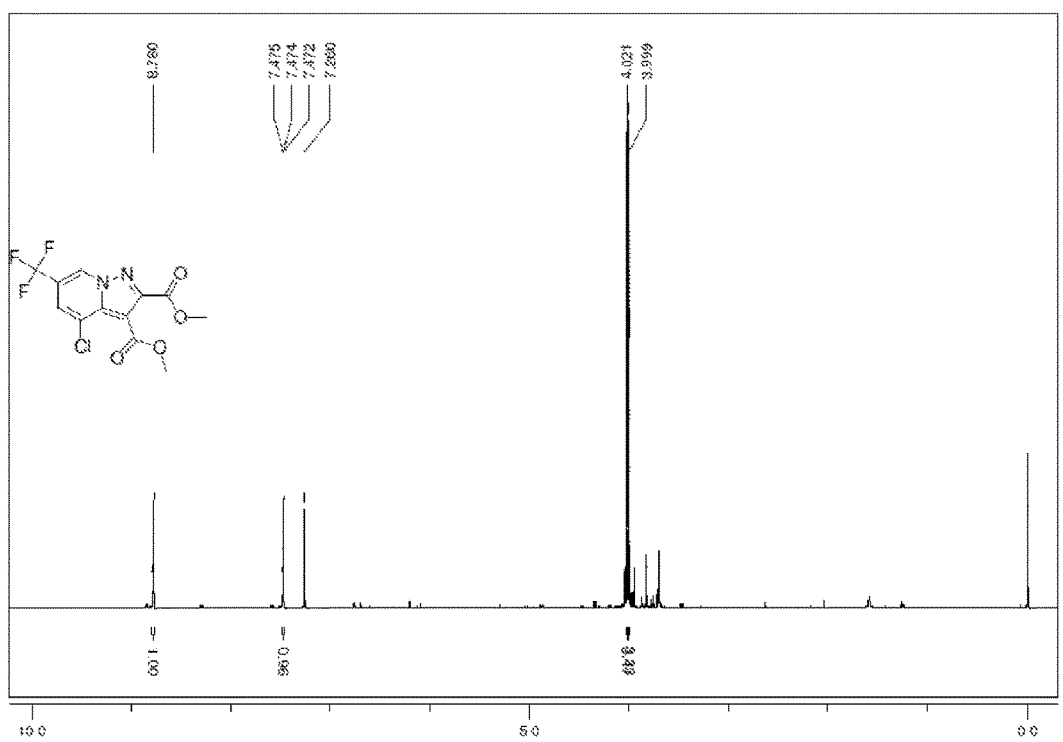
FIG. 2 depicts H-NMR spectrum of dimethyl 4-chloro-6-(trifluoromethyl)pyrazolo[1,5-a]pyridine-2,3-dicarboxylate ($CDCl_3$, 400 MHz).

See FIG. 2, which depicts the $^1$H-NMR spectrum of dimethyl 4-chloro-6-(trifluoromethyl)pyrazolo[1,5-a]pyridine-2,3-dicarboxylate (CDCl$_3$, 400 MHz)

Step 3: Preparation of 4-chloro-6-(trifluoromethyl) pyrazolo[1,5-a]pyridine-2-carboxylic Acid (II-1)

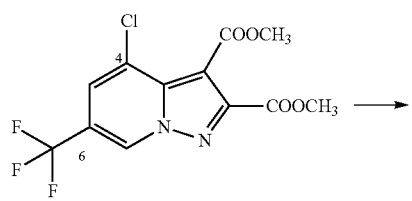

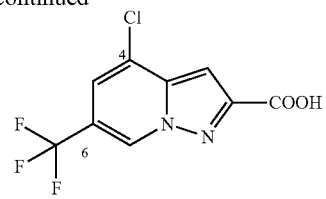

A solution of dimethyl 4-chloro-6-(trifluoromethyl)pyrazolo[1,5-a]pyridine-2,3-dicarboxylate (7.1 g, 21 mmol) in aq. sulfuric acid (150 mL, v/v 50%) was heated to 90° C. for 24 h. Then the mixture was cooled to room temperature, neutralized with 5 N NaOH followed by treatment with 2 N aq. HCl until pH=2-3 was reached. The mixture was extracted with ethyl acetate (3×80 mL) and the combined organic phases were washed with brine, dried over sodium sulfate, filtered, and evaporated, followed by re-crystallization from dichloromethane/n-hexane (2/1, v/v) to give 3.7 g pure target compound 4-chloro-6-(trifluoromethyl)pyrazolo[1,5-a]pyridine-2-carboxylic acid (II-1) as a white solid.

Figure 3:
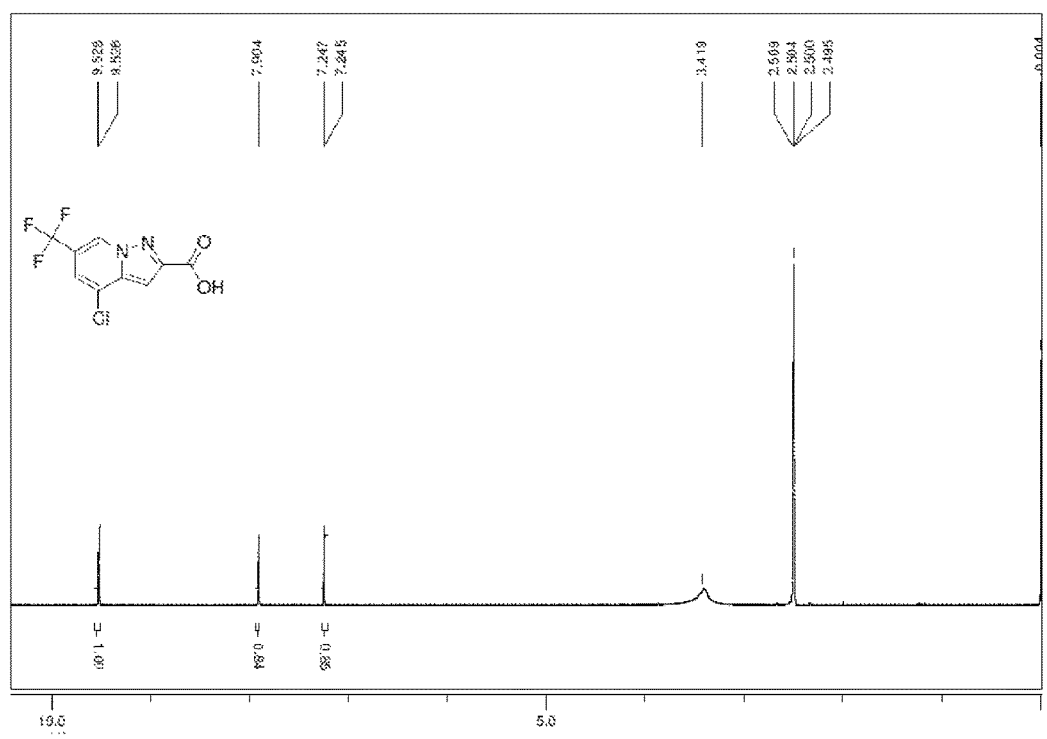
FIG. 3 depicts the H-NMR spectrum of 4-chloro-6-(trifluoromethyl)pyrazolo[1,5-a]pyridine-2-carboxylic acid (II-1) ([$D_6$]-DMSO, 400 MHz).

See FIG. 3, which depicts the $^1$H-NMR spectrum of 4-chloro-6-(trifluoromethyl)pyrazolo[1,5-a]pyridine-2-carboxylic acid (II-1) ([D$_6$]-DMSO, 400 MHz)

According to the method described above, the following compounds of general formula (I) have been prepared.

Compounds of General Formula (I):

TABLE 2

(I)

$Z = O$, $R^2$ and $R^3$ are H and Q = substituted aryl, alkyl or cycloalkyl as indicated

| Example | $R^1$ | n | Q | Remarks |
|---|---|---|---|---|
| I-1 | 5-CF$_3$ | 1 | Cl-phenyl | NMR |
| I-2 | 4-Cl, 6-CF$_3$ | 2 | Cl, CF$_3$-pyridyl | NMR |
| I-3 | 4-Cl, 6-CF$_3$ | 2 | Cl, OMe-phenyl | NMR |
| I-4 | 4-Cl, 6-CF$_3$ | 2 | CF$_3$-phenyl | NMR |

TABLE 2-continued (I)

Z = O, R² and R³ are H and Q = substituted aryl, alkyl or cycloalkyl as indicated

| Example | R¹ | n | Q | Remarks |
|---|---|---|---|---|
| I-5 | 4-Cl, 6-CF₃ | 2 | 2-(OCF₃)phenyl | NMR |
| I-6 | 4-Cl, 6-CF₃ | 2 | 2-Cl-phenyl | NMR |
| I-7 | 4-Cl, 6-CF₃ | 2 | 2,6-diF-phenyl | NMR |
| I-8 | 4-Cl, 6-CF₃ | 2 | 2-MeO-phenyl | NMR |
| I-9 | 4-Cl, 6-CF₃ | 2 | 4-Cl-phenyl | NMR |
| I-10 | 4-Cl, 6-CF₃ | 2 | 2-Me-phenyl | NMR |
| I-11 | 4-Cl, 6-CF₃ | 2 | 2,4-diCl-phenyl | NMR |
| I-12 | 4-Cl, 6-CF₃ | 2 | 3-Cl-phenyl | NMR |
| I-13 | 4-Cl, 6-CF₃ | 2 | phenyl | NMR |
| I-14 | 4-Cl, 6-CF₃ | 2 | 5-Cl-2,2-difluoro-benzo[1,3]dioxole | NMR |
| I-15 | 4-Cl, 6-CF₃ | 2 | CH₃ | NMR |
| I-16 | 4-Cl, 6-CF₃ | 2 | Et | NMR |
| I-17 | 4-Cl, 6-CF₃ | 2 | cyclopropyl | NMR |
| I-18 | 4-Cl, 6-CF₃ | 2 | 2,6-diCl-phenyl | NMR |
| I-19 | 5-CF₃, 7-Cl | 2 | 2-Cl-phenyl | NMR |
| I-20 | 5-CF₃, 7-Cl | 2 | 4-Cl-phenyl | NMR |
| I-21 | 5-CF₃, 7-Cl | 2 | 2,6-diCl-phenyl | NMR |
| I-22 | 5-CF₃, 7-Cl | 2 | 2,4-diCl-phenyl | NMR |
| I-23 | 5-CF₃, 7-Cl | 2 | 2-Cl-4-OMe-phenyl | NMR |

TABLE 2-continued

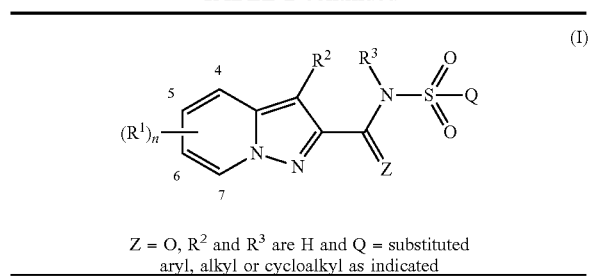

Z = O, R² and R³ are H and Q = substituted aryl, alkyl or cycloalkyl as indicated

| Example | R¹ | n | Q | Remarks |
|---|---|---|---|---|
| I-24 | 5-CF₃, 7-Cl | 2 | 2,6-difluorophenyl | NMR |
| I-25 | 5-CF₃ | 1 | 2,3-dichlorophenyl | NMR |
| I-26 | 5-CF₃ | 1 | 2,5-dichlorophenyl | NMR |
| I-27 | 5-CF₃ | 1 | 2-Cl-5-OMe-phenyl | NMR |
| I-28 | 5-CF₃, 7-Cl | 2 | —CH₃ | NMR |
| I-29 | 5-CF₃ | 1 | cyclopropyl | NMR |
| I-30 | 5-CF₃, 7-Cl | 2 | 3-chlorophenyl | NMR |
| I-31 | 5-CF₃, 7-Cl | 2 | cyclopropyl | NMR |
| I-32 | 5-CF₃, 7-Cl | 2 | Et | NMR |
| I-33 | 5-CF₃ | 1 | 2-Cl-5-CF₃-phenyl | NMR |

TABLE 2-continued

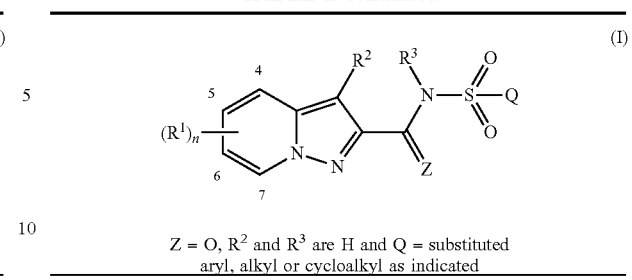

Z = O, R² and R³ are H and Q = substituted aryl, alkyl or cycloalkyl as indicated

| Example | R¹ | n | Q | Remarks |
|---|---|---|---|---|
| I-34 | 5-CF₃ | 1 | 2-Cl-5-OEt-phenyl | NMR |
| I-35 | 5-CF₃ | 1 | 2-Cl-5-OProp-phenyl | NMR |
| I-36 | 5-CF₃ | 1 | 2-Cl-5-Et-phenyl | NMR |
| I-37 | 5-CF₃ | 1 | 2-Br-5-OMe-phenyl | NMR |
| I-38 | 5-CF₃ | 1 | 2-F-5-OMe-phenyl | NMR |
| I-39 | 5-CF₃ | 1 | 2-(SMe)-3-Cl-phenyl | NMR |
| I-40 | 5-CF₃ | 1 | 2-(SEt)-3-Cl-phenyl | NMR |

TABLE 2-continued

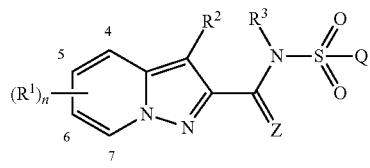

(I)

Z = O, R² and R³ are H and Q = substituted aryl, alkyl or cycloalkyl as indicated

| Example | R¹ | n | Q | Remarks |
|---|---|---|---|---|
| I-41 | 5-CF₃ | 1 | 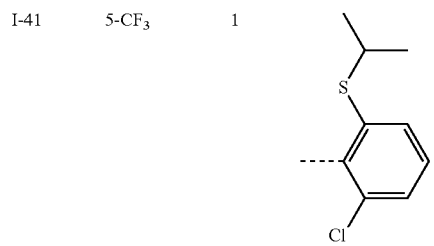 | NMR |
| I-42 | 5-CF₃ | 1 | 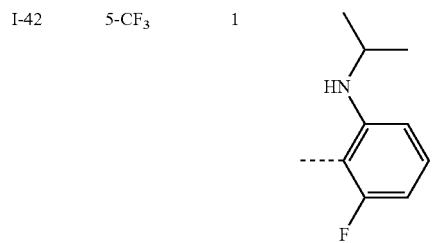 | NMR |
| I-43 | 5-CF₃ | 1 | 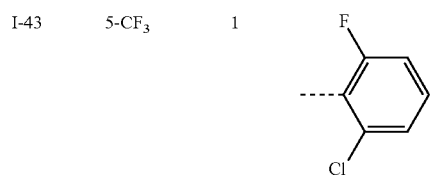 | NMR |
| I-44 | 5-CF₃, 7-Cl | 2 | 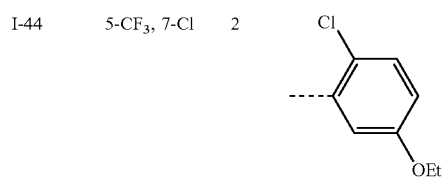 | NMR |
| I-45 | 5-CF₃, 7-Cl | 2 | 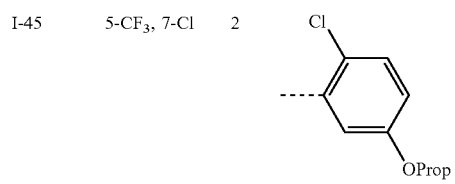 | NMR |
| I-46 | 5-Cl, 7-Cl | 2 |  | NMR |

TABLE 2-continued

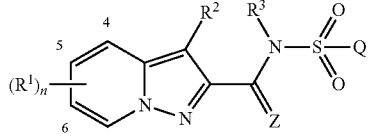

(I)

Z = O, R² and R³ are H and Q = substituted aryl, alkyl or cycloalkyl as indicated

| Example | R¹ | n | Q | Remarks |
|---|---|---|---|---|
| I-47 | 5-Cl, 7-Cl | 2 | 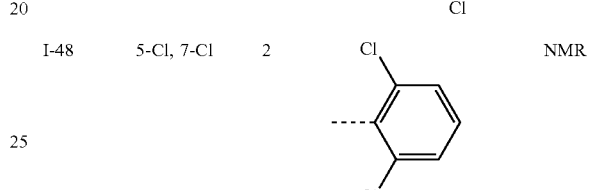 | NMR |
| I-48 | 5-Cl, 7-Cl | 2 | 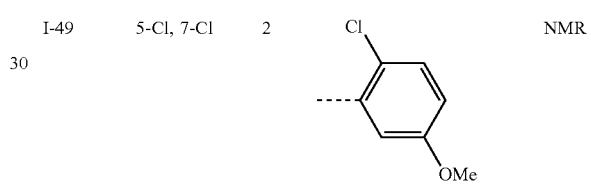 | NMR |
| I-49 | 5-Cl, 7-Cl | 2 | 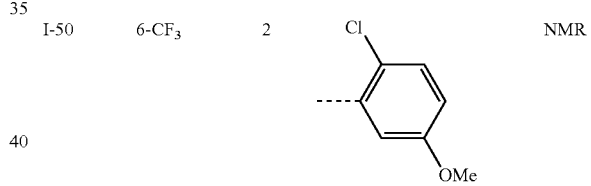 | NMR |
| I-50 | 6-CF₃ | 2 | 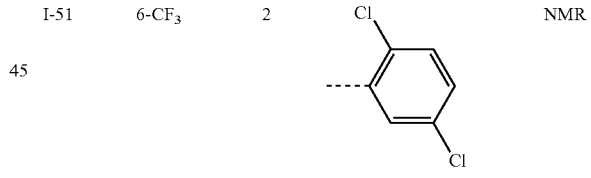 | NMR |
| I-51 | 6-CF₃ | 2 | 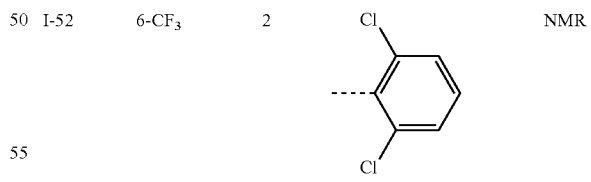 | NMR |
| I-52 | 6-CF₃ | 2 | 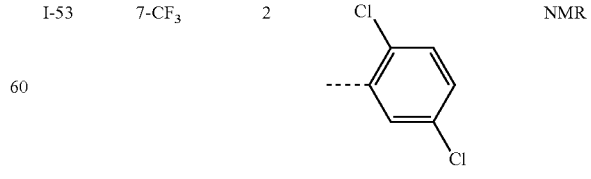 | NMR |
| I-53 | 7-CF₃ | 2 | 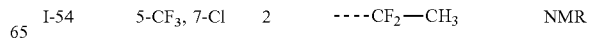 | NMR |
| I-54 | 5-CF₃, 7-Cl | 2 | ----CF₂—CH₃ | NMR |

TABLE 2-continued

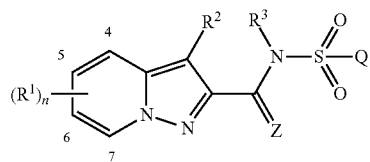

(I)

Z = O, R² and R³ are H and Q = substituted aryl, alkyl or cycloalkyl as indicated

| Example | R¹ | n | Q | Remarks |
|---|---|---|---|---|
| I-55 | 5-CF₃, 7-Cl | 2 | ----CF₃ | NMR |
| I-56 | 5-Cl, 7-Cl | 2 | 2-Cl, 5-CF₃ phenyl | NMR |
| I-57 | 5-Cl, 7-Cl | 2 | 2-Cl, 5-OEt phenyl | NMR |
| I-58 | 5-Cl, 7-Cl | 2 | 2-Cl, 5-OProp phenyl | NMR |
| I-59 | 5-Cl, 7-Cl | 2 | 2-Cl, 5-Et phenyl | NMR |
| I-60 | 5-Cl, 7-Cl | 2 | 4-Cl, 3-SMe phenyl | NMR |
| I-61 | 5-Cl, 7-Cl | 2 | 2-SEt, 3-Cl phenyl | NMR |

TABLE 2-continued

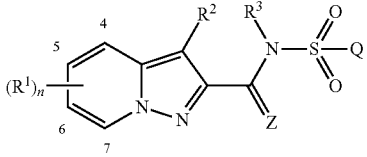

(I)

Z = O, R² and R³ are H and Q = substituted aryl, alkyl or cycloalkyl as indicated

| Example | R¹ | n | Q | Remarks |
|---|---|---|---|---|
| I-62 | 5-CF₃, 7-Cl | 2 | 2-Cl, 5-Et phenyl | NMR |
| I-63 | 5-CF₃, 7-Cl | 2 | 2-SEt, 3-Cl phenyl | NMR |
| I-64 | 5-CF₃, 7-Cl | 2 | 2-SiPr, 3-Cl phenyl | NMR |
| I-65 | 5-CF₃, 7-Cl | 2 | 2-F, 3-Cl phenyl | NMR |
| I-66 | 5-Cl, 7-Cl | 2 | 2-NHiPr, 3-F phenyl | NMR |
| I-67 | 5-Cl, 7-Cl | 2 | 2-F, 3-Cl phenyl | NMR |

TABLE 2-continued

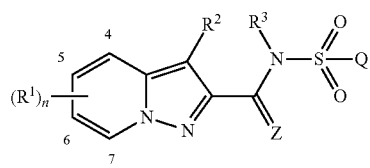

(I)

Z = O, R² and R³ are H and Q = substituted aryl, alkyl or cycloalkyl as indicated

| Example | R¹ | n | Q | Remarks |
|---|---|---|---|---|
| I-68 | 5-Cl, 7-Cl | 2 | 3-F, 4-OMe phenyl | NMR |
| I-69 | 5-Cl, 7-Cl | 2 | 3-Br, 5-OMe phenyl | NMR |
| I-70 | 5-CF₃, 7-Cl | 2 | 3-Br, 5-OMe phenyl | NMR |
| I-71 | 5-CF₃, 7-Cl | 2 | 2-SMe, 3-Cl phenyl | NMR |
| I-72 | 5-CF₃, 7-Cl | 2 | 2-Cl, 4-CF₃ phenyl | NMR |
| I-73 | 5-CF₃ | 1 | 2-Br, 4-CF₃ phenyl | NMR |
| I-74 | 5-CF₃, 7-Cl | 2 | 3-F, 4-OMe phenyl | NMR |

TABLE 2-continued

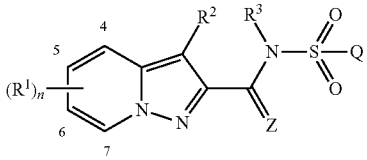

(I)

Z = O, R² and R³ are H and Q = substituted aryl, alkyl or cycloalkyl as indicated

| Example | R¹ | n | Q | Remarks |
|---|---|---|---|---|
| I-75 | 5-Cl, 7-Cl | 2 | 2-Me, 4-Et phenyl | NMR |
| I-76 | 5-Cl, 7-Cl | 2 | 2-SMe, 3-Cl phenyl | NMR |
| I-77 | 5-CF₃, 7-Cl | 2 | 2-Me, 4-Et phenyl | NMR |
| I-78 | 5-CF₃ | 1 | 2-Me, 4-Et phenyl | NMR |

¹H-NMR Data of Compounds of General Formula (I):

TABLE 3

| Example | NMR data |
| --- | --- |
| I-1 | ¹H-NMR, Solvent [D₆]-DMSO, spectrometer: 399.95 MHz:<br>δ = 7.681 (0.3); 7.508 (0.4); 3.187 (0.4); 3.170 (16.0); 2.512 (2.8); 2.508 (5.6); 2.503 (7.5); 2.499 (5.6); 2.494 (2.8); 0.008 (0.4); 0.000 (9.6); −0.009 (0.4). |
| I-2 | ¹H-NMR, Solvent [D₆]-DMSO, spectrometer: 399.95 MHz:<br>δ = 9.449 (10.2); 9.086 (9.9); 9.085 (9.9); 8.798 (9.0); 7.924 (12.6); 7.475 (11.3); 5.758 (16.0); 4.540 (0.4); 4.525 (0.4); 4.172 (0.6); 4.045 (0.6); 3.975 (0.6); 3.817 (0.5); 3.801 (0.4); 3.787 (0.4); 2.676 (0.6); 2.672 (1.0); 2.667 (0.6); 2.507 (178.2); 2.502 (241.8); 2.498 (190.2); 2.334 (1.9); 2.329 (2.3); 2.325 (2.0); 2.110 (0.4); 2.076 (0.4); 1.575 (0.7); 1.570 (0.4); 1.352 (0.4); 1.259 (0.4); 1.233 (0.8); 1.188 (1.7); 0.008 (0.4); 0.000 (14.1); −0.008 (1.1). |
| I-3 | ¹H-NMR, Solvent [D₆]-DMSO, spectrometer: 399.95 MHz:<br>δ = 9.436 (2.2); 7.928 (2.8); 7.652 (2.8); 7.644 (2.8); 7.593 (2.4); 7.581 (2.5); 7.571 (2.8); 7.316 (1.3); 7.308 (1.3); 7.294 (1.2); 7.286 (1.1); 5.759 (0.8); 3.870 (16.0); 2.671 (0.4); 2.511 (22.7); 2.507 (44.0); 2.502 (57.7); 2.498 (42.9); 2.494 (21.9); 2.329 (0.4); 0.000 (2.8). |
| I-4 | ¹H-NMR, Solvent [D₆]-DMSO, spectrometer: 399.95 MHz:<br>δ = 9.437 (9.6); 8.415 (5.6); 8.396 (6.2); 8.024 (4.1); 8.005 (6.5); 7.991 (2.3); 7.975 (5.3); 7.956 (4.4); 7.941 (4.6); 7.922 (16.0); 7.905 (2.1); 7.529 (9.4); 7.388 (0.5); 5.759 (4.0); 3.891 (0.4); 3.687 (0.7); 2.676 (1.4); 2.672 (1.9); 2.667 (1.4); 2.525 (5.9); 2.512 (102.7); 2.507 (200.2); 2.503 (260.4); 2.498 (190.6); 2.494 (93.7); 2.334 (1.3); 2.330 (1.7); 2.325 (1.2); 1.584 (0.4); 1.576 (0.4); 1.546 (0.4); 0.000 (3.2). |
| I-5 | ¹H-NMR, Solvent [D₆]-DMSO, spectrometer: 399.95 MHz:<br>δ = 9.429 (13.3); 8.185 (7.8); 8.166 (8.3); 7.922 (16.0); 7.872 (3.4); 7.853 (7.2); 7.836 (4.5); 7.833 (4.5); 7.670 (5.7); 7.651 (9.7); 7.632 (4.9); 7.611 (6.6); 7.591 (5.7); 7.548 (13.2); 3.892 (0.5); 3.868 (0.5); 3.843 (0.5); 3.841 (0.5); 3.823 (0.5); 3.750 (0.7); 3.744 (0.7); 3.718 (0.8); 3.693 (0.8); 3.661 (0.9); 3.639 (0.9); 3.629 (0.9); 3.604 (0.9); 3.579 (1.0); 3.560 (0.9); 3.543 (0.9); 3.507 (1.0); 3.448 (0.9); 3.391 (0.7); 3.382 (0.7); 3.362 (0.7); 3.314 (0.6); 3.245 (0.5); 3.161 (0.4); 2.672 (2.1); 2.503 (286.4); 2.330 (2.0); 2.076 (1.0); 1.576 (3.0); 0.000 (3.1). |
| I-6 | ¹H-NMR, Solvent [D₆]-DMSO, spectrometer: 399.95 MHz:<br>δ = 9.439 (12.7); 9.437 (12.7); 8.219 (7.9); 8.216 (8.3); 8.200 (8.7); 8.196 (8.6); 7.928 (16.0); 7.747 (2.1); 7.743 (2.3); 7.727 (6.3); 7.709 (7.3); 7.706 (7.0); 7.686 (12.8); 7.670 (5.6); 7.666 (4.6); 7.659 (6.3); 7.655 (5.0); 7.639 (7.9); 7.622 (3.8); 7.618 (3.3); 7.588 (13.0); 7.422 (0.4); 5.759 (10.2); 3.691 (0.8); 3.428 (2.8); 3.128 (0.5); 3.053 (0.3); 2.676 (1.9); 2.672 (2.5); 2.667 (1.8); 2.524 (8.2); 2.511 (136.7); 2.507 (258.7); 2.502 (331.6); 2.498 (240.2); 2.334 (1.6); 2.329 (2.1); 2.325 (1.5); 0.000 (3.7). |
| I-7 | ¹H-NMR, Solvent [D₆]-DMSO, spectrometer: 399.95 MHz:<br>δ = 9.564 (0.9); 9.433 (7.5); 9.431 (7.5); 7.918 (9.1); 7.802 (0.8); 7.787 (1.7); 7.781 (1.7); 7.766 (2.9); 7.750 (1.7); 7.745 (1.7); 7.730 (0.8); 7.496 (7.9); 7.384 (0.5); 7.363 (0.4); 7.339 (5.2); 7.316 (8.0); 7.293 (4.5); 7.221 (1.3); 7.219 (1.3); 4.064 (0.3); 4.046 (0.3); 4.021 (0.3); 3.988 (0.4); 3.960 (0.4); 3.939 (0.4); 3.918 (0.4); 3.891 (0.5); 3.862 (0.4); 3.852 (0.4); 3.844 (0.4); 3.827 (0.4); 3.818 (0.4); 3.798 (0.4); 3.779 (0.4); 3.772 (0.4); 3.767 (0.4); 3.759 (0.4); 3.752 (0.4); 3.744 (0.4); 3.713 (0.5); 3.689 (0.4); 3.677 (0.4); 3.644 (0.4); 3.621 (0.4); 3.589 (0.4); 3.568 (0.3); 2.676 (1.1); 2.672 (1.5); 2.667 (1.2); 2.507 (153.3); 2.503 (196.7); 2.498 (149.6); 2.334 (1.0); 2.329 (1.3); 2.325 (1.0); 2.076 (0.9); 1.583 (16.0); 1.333 (0.4); 1.317 (0.4); 0.930 (0.5); 0.000 (1.9). |
| I-8 | ¹H-NMR, Solvent [D₆]-DMSO, spectrometer: 399.95 MHz:<br>δ = 9.457 (2.4); 7.956 (1.6); 7.952 (1.7); 7.936 (1.9); 7.931 (2.3); 7.928 (3.2); 7.713 (0.7); 7.709 (0.8); 7.691 (1.4); 7.674 (0.9); 7.670 (0.9); 7.632 (3.2); 7.255 (2.1); 7.234 (1.9); 7.191 (1.1); 7.173 (2.0); 7.153 (1.0); 3.860 (16.0); 3.339 (3.9); 2.676 (0.3); 2.671 (0.4); 2.524 (1.4); 2.511 (25.9); 2.507 (49.8); 2.502 (64.4); 2.498 (47.0); 2.493 (23.0); 2.329 (0.4); 0.000 (0.4). |
| I-9 | ¹H-NMR, Solvent CD₃CN, spectrometer: 600 MHz:<br>δ = 8.926 (8.4); 8.924 (8.6); 8.090 (2.1); 8.086 (15.0); 8.083 (6.2); 8.075 (5.7); 8.071 (16.0); 7.638 (2.3); 7.634 (16.0); 7.630 (6.4); 7.622 (5.5); 7.619 (14.9); 7.595 (0.4); 7.584 (10.4); 7.582 (10.8); 7.257 (13.2); 7.256 (13.6); 7.107 (0.3); 5.447 (1.1); 2.052 (0.3); 1.966 (1.8); 1.958 (3.1); 1.953 (4.2); 1.950 (18.9); 1.946 (32.5); 1.941 (46.9); 1.937 (32.8); 1.933 (17.0); 1.601 (4.9); 1.576 (0.9); 1.266 (0.4); 0.005 (1.3); 0.000 (29.0); −0.006 (1.4). |
| I-10 | ¹H-NMR, Solvent [D₆]-DMSO, spectrometer: 399.95 MHz:<br>δ = 9.433 (3.1); 8.088 (2.0); 8.085 (2.1); 8.068 (2.2); 8.065 (2.2); 7.930 (4.0); 7.627 (0.8); 7.624 (0.9); 7.608 (2.0); 7.605 (2.1); 7.590 (1.4); 7.587 (1.3); 7.532 (5.0); 7.494 (1.3); 7.475 (2.1); 7.457 (0.9); 7.431 (2.2); 7.412 (1.9); 5.757 (0.6); 3.411 (0.4); 3.394 (0.4); 2.673 (0.4); 2.636 (16.0); 2.526 (0.9); 2.512 (18.6); 2.508 (37.0); 2.504 (48.3); 2.499 (35.0); 2.495 (17.0); 1.756 (0.4); 0.000 (0.7). |
| I-11 | ¹H-NMR, Solvent [D₆]-DMSO, spectrometer: 399.95 MHz:<br>δ = 9.428 (11.7); 9.426 (11.2); 8.135 (13.6); 8.129 (13.8); 7.916 (14.9); 7.914 (14.2); 7.821 (5.7); 7.815 (5.4); 7.800 (8.6); 7.793 (8.3); 7.721 (16.0); 7.700 (10.5); 7.522 (13.8); 3.187 (0.6); 2.512 (55.8); 2.508 (120.5); 2.504 (164.9); 2.499 (128.9); 2.495 (72.6); 2.335 (1.6); 2.330 (1.9); 2.326 (1.6); 1.757 (0.6); 1.546 (0.5); 0.000 (3.6). |
| I-12 | ¹H-NMR, Solvent [D₆]-DMSO, spectrometer: 399.95 MHz:<br>δ = 9.444 (11.1); 9.442 (11.1); 8.317 (0.3); 8.013 (6.8); 8.008 (13.0); 8.003 (8.8); 7.985 (6.6); 7.965 (7.2); 7.924 (14.2); 7.922 (14.2); 7.830 (4.6); 7.827 (4.4); 7.825 (4.1); 7.812 (5.7); 7.810 (6.1); 7.807 (6.1); 7.711 (8.4); 7.691 (12.9); 7.671 (5.5); 7.447 (16.0); 5.758 (10.7); 3.187 (1.9); 2.772 (1.1); 2.760 (1.2); 2.676 (1.2); 2.672 (1.7); 2.667 (1.2); 2.663 (0.5); 2.525 (5.3); 2.512 (100.2); 2.507 (200.5); 2.503 (264.5); 2.498 (194.2); 2.494 (96.4); 2.339 (0.8); 2.334 (1.4); 2.330 (1.9); 2.325 (1.4); 2.321 (0.8); 2.076 (0.6); 1.755 (1.3); 1.546 (0.4); 1.006 (0.4); 0.988 (0.9); 0.970 (0.4); 0.000 (6.4). |
| I-13 | ¹H-NMR, Solvent [D₆]-DMSO, spectrometer: 399.95 MHz:<br>δ = 9.443 (10.8); 9.441 (10.9); 8.041 (14.0); 8.023 (16.0); 8.019 (11.6); 7.927 (13.9); 7.926 (13.9); 7.758 (2.5); 7.739 (7.8); 7.721 (5.9); 7.677 (11.4); 7.657 (15.7); 7.639 (6.0); 7.474 (16.0); 7.319 (0.4); 7.202 (0.4); 5.758 (11.5); 3.892 (0.4); 3.637 (0.4); 3.402 (1.3); 2.676 (1.5); 2.672 (2.0); 2.667 (1.5); 2.511 (117.5); 2.507 (218.7); 2.502 (278.4); 2.498 (202.5); 2.494 (100.2); 2.334 (1.3); 2.329 (1.8); 2.325 (1.3); 2.076 (0.5); 1.755 (0.9); 1.576 (4.9); 1.545 (0.8); 1.309 (0.3); 0.008 (1.4); 0.000 (29.6); −0.008 (1.2). |
| I-14 | ¹H-NMR, Solvent [D₆]-DMSO, spectrometer: 399.95 MHz:<br>δ = 9.427 (8.6); 9.425 (8.5); 8.316 (0.5); 8.201 (16.0); 7.920 (16.0); 7.912 (11.4); 7.514 (8.3); 7.219 (0.4); 7.217 (0.4); 5.757 (10.0); 2.677 (0.8); 2.672 (1.2); 2.668 (0.8); 2.525 (2.3); 2.512 (76.8); 2.507 (158.4); 2.503 (212.1); 2.498 (157.9); 2.494 (80.1); 2.334 (1.2); 2.330 (1.6); 2.325 (1.3); 1.755 (0.6); 1.584 (4.8); 0.146 (0.5); 0.008 (3.8); 0.000 (132.9); −0.008 (6.0); −0.150 (0.7). |
| I-15 | ¹H-NMR, Solvent [D₆]-DMSO, spectrometer: 399.95 MHz:<br>δ = 12.425 (0.4); 9.491 (9.5); 7.947 (12.2); 7.578 (16.0); 3.580 (0.3); 3.407 (58.8); 3.352 (3.0); 3.231 (0.5); 2.676 (0.6); 2.672 (0.8); 2.507 (98.4); 2.503 (124.9); 2.499 (93.8); 2.334 (0.6); 2.330 (0.8); 2.326 (0.6); 1.755 (0.3); 0.000 (17.3) |
| I-16 | ¹H-NMR, Solvent [D₆]-DMSO, spectrometer: 399.95 MHz:<br>δ = 9.493 (4.0); 9.490 (3.9); 7.949 (5.2); 7.946 (5.1); 7.581 (7.0); 7.579 (6.9); 3.565 (1.8); 3.547 (6.1); 3.528 (6.2); 3.510 (1.9); 3.338 (4.6); 2.676 (0.4); 2.672 (0.6); 2.667 (0.4); 2.525 (1.8); 2.512 (33.4); 2.507 (65.9); 2.503 (85.4); 2.498 (60.7); 2.494 (28.6); 2.334 (0.4); 2.329 (0.6); 2.325 (0.4); 1.297 (7.0); 1.279 (16.0); 1.261 (6.8); 0.008 (0.6); 0.000 (15.5); −0.009 (0.5). |

TABLE 3-continued

| Example | NMR data |
|---|---|
| I-17 | $^1$H-NMR, Solvent [D$_6$]-DMSO, spectrometer: 399.95 MHz:<br>δ = 12.379 (0.9); 9.483 (10.3); 8.316 (0.4); 7.948 (13.2); 7.553 (16.0); 5.757 (5.2); 3.337 (14.4); 3.168 (1.4); 3.164 (1.3); 3.152 (2.5); 3.144 (2.8); 3.132 (4.7); 3.120 (2.9); 3.113 (2.7); 3.100 (1.3); 2.676 (1.1); 2.671 (1.4); 2.667 (1.1); 2.507 (173.3); 2.502 (220.2); 2.498 (161.3); 2.329 (1.4); 2.325 (1.0); 1.214 (1.8); 1.199 (6.1); 1.193 (8.1); 1.184 (10.2); 1.174 (3.9); 1.157 (5.4); 1.148 (7.1); 1.142 (7.1); 1.128 (7.7); 1.108 (1.7); 0.000 (31.4); −0.008 (1.3). |
| I-18 | $^1$H-NMR, Solvent [D$_6$]-DMSO, spectrometer: 399.95 MHz:<br>δ = 9.413 (7.2); 9.410 (7.3); 8.316 (0.6); 7.911 (8.7); 7.909 (8.7); 7.672 (5.8); 7.668 (7.0); 7.650 (16.0); 7.608 (5.9); 7.591 (4.0); 7.586 (3.1); 7.569 (2.1); 7.519 (5.8); 3.929 (0.5); 3.892 (0.4); 3.802 (0.4); 3.785 (0.4); 3.768 (0.4); 3.729 (0.5); 3.712 (0.6); 3.675 (0.5); 3.668 (0.5); 3.639 (0.5); 3.609 (0.5); 3.594 (0.5); 3.579 (0.5); 3.506 (0.6); 3.499 (0.5); 3.393 (0.5); 3.355 (0.4); 3.303 (0.3); 3.187 (1.6); 3.010 (0.4); 2.770 (1.3); 2.757 (1.4); 2.676 (1.2); 2.671 (1.7); 2.667 (1.1); 2.545 (0.4); 2.542 (0.7); 2.525 (3.3); 2.511 (83.5); 2.507 (170.6); 2.502 (224.9); 2.498 (161.6); 2.493 (77.2); 2.334 (1.1); 2.329 (1.5); 2.325 (1.1); 2.075 (2.5); 1.235 (0.6); 1.006 (0.5); 0.988 (1.0); 0.970 (0.5); 0.146 (1.0); 0.008 (9.0); 0.000 (254.3); −0.009 (8.7); −0.025 (0.4); −0.032 (0.3); −0.150 (1.1). |
| I-19 | $^1$H-NMR, Solvent [D$_6$]-DMSO, spectrometer: 399.95 MHz:<br>δ = 8.496 (7.2); 8.228 (4.4); 8.224 (4.8); 8.208 (4.8); 8.204 (5.1); 7.813 (8.1); 7.809 (8.3); 7.757 (1.3); 7.753 (1.4); 7.737 (3.7); 7.733 (3.7); 7.715 (16.0); 7.695 (5.7); 7.692 (7.7); 7.675 (3.5); 7.669 (4.4); 7.665 (3.2); 7.649 (4.6); 7.631 (2.3); 7.628 (2.1); 7.608 (0.4); 5.757 (1.4); 3.171 (0.6); 2.678 (0.4); 2.673 (0.5); 2.669 (0.4); 2.513 (28.2); 2.509 (56.0); 2.504 (74.5); 2.500 (56.5); 2.496 (29.7); 2.335 (0.4); 2.331 (0.5); 2.327 (0.4); 0.146 (0.4); 0.008 (3.5); 0.000 (82.0); −0.008 (4.5); −0.150 (0.4). |
| I-20 | $^1$H-NMR, Solvent [D$_6$]-DMSO, spectrometer: 399.95 MHz:<br>δ = 8.462 (8.7); 8.317 (0.4); 8.048 (14.0); 8.027 (16.0); 7.838 (0.8); 7.824 (9.5); 7.821 (9.4); 7.755 (15.5); 7.734 (13.2); 7.668 (0.6); 7.647 (0.4); 7.576 (15.3); 7.467 (0.5); 3.724 (0.3); 3.713 (0.3); 3.635 (0.5); 3.608 (0.5); 3.536 (0.6); 3.510 (0.6); 3.468 (0.6); 3.451 (0.6); 3.435 (0.6); 3.419 (0.6); 3.400 (0.6); 3.362 (0.4); 3.343 (0.4); 3.311 (0.3); 3.188 (1.7); 3.171 (1.3); 2.822 (0.4); 2.810 (0.4); 2.673 (0.8); 2.508 (89.5); 2.504 (114.0); 2.500 (85.6); 2.335 (0.5); 2.331 (0.7); 2.326 (0.5); 0.146 (0.6); 0.007 (6.6); 0.000 (114.3); −0.150 (0.6). |
| I-21 | $^1$H-NMR, Solvent [D$_6$]-DMSO, spectrometer: 399.95 MHz:<br>δ = 8.495 (7.3); 7.808 (7.7); 7.804 (7.6); 7.699 (13.6); 7.693 (8.7); 7.675 (16.0); 7.636 (5.9); 7.619 (4.0); 7.613 (3.3); 7.596 (2.1); 5.757 (1.4); 3.171 (1.4); 2.673 (0.5); 2.508 (64.6); 2.504 (79.6); 2.331 (0.5); 0.146 (0.4); 0.000 (67.8); −0.150 (0.4). |
| I-22 | $^1$H-NMR, Solvent [D$_6$]-DMSO, spectrometer: 399.95 MHz:<br>δ = 8.484 (11.2); 8.143 (9.5); 8.137 (10.2); 7.830 (4.5); 7.824 (4.8); 7.801 (16.0); 7.726 (10.7); 7.705 (7.6); 7.668 (14.4); 7.635 (0.6); 7.617 (0.7); 7.611 (0.7); 7.471 (0.7); 7.464 (0.5); 7.402 (0.7); 7.380 (0.4); 5.757 (0.4); 3.187 (0.4); 2.828 (1.0); 2.816 (1.1); 2.673 (0.6); 2.504 (128.2); 2.398 (0.6); 2.353 (0.4); 2.331 (1.1); 1.185 (0.6); 0.000 (81.3); −0.150 (0.6). |
| I-23 | $^1$H-NMR, Solvent [D$_6$]-DMSO, spectrometer: 399.95 MHz:<br>δ = 8.494 (2.5); 7.810 (2.6); 7.806 (2.8); 7.707 (3.6); 7.661 (2.8); 7.653 (3.0); 7.594 (2.3); 7.572 (2.7); 7.321 (1.4); 7.313 (1.4); 7.299 (1.2); 7.291 (1.2); 3.874 (16.0); 3.817 (0.3); 3.188 (0.5); 3.170 (0.7); 2.508 (27.5); 2.504 (36.7); 2.499 (28.8); 0.008 (1.6); 0.000 (37.0). |
| I-24 | $^1$H-NMR, Solvent [D$_6$]-DMSO, spectrometer: 399.95 MHz:<br>δ = 8.489 (10.6); 7.988 (0.3); 7.825 (1.3); 7.812 (12.9); 7.809 (13.3); 7.789 (4.5); 7.774 (2.7); 7.768 (2.7); 7.753 (1.2); 7.656 (16.0); 7.359 (7.2); 7.336 (11.5); 7.314 (6.6); 7.289 (0.3); 7.266 (0.3); 5.757 (2.0); 3.188 (0.9); 2.673 (0.5); 2.504 (107.9); 2.500 (88.7); 2.391 (0.3); 2.331 (0.9); 0.146 (0.4); 0.000 (86.5); −0.150 (0.5). |
| I-25 | $^1$H-NMR, Solvent [D$_6$]-DMSO, spectrometer: 399.95 MHz:<br>δ = 8.944 (4.5); 8.926 (4.6); 8.426 (6.1); 8.317 (0.5); 7.913 (1.4); 7.688 (5.2); 7.684 (6.8); 7.666 (16.0); 7.628 (6.8); 7.612 (3.9); 7.606 (5.4); 7.589 (2.0); 7.536 (1.0); 7.518 (0.8); 7.514 (0.8); 7.496 (8.8); 7.340 (3.7); 7.335 (4.0); 7.321 (3.6); 7.316 (3.9); 6.993 (0.4); 6.974 (0.4); 5.756 (5.6); 3.910 (1.0); 3.785 (0.4); 3.187 (5.6); 3.170 (0.6); 2.677 (0.6); 2.672 (0.9); 2.668 (0.7); 2.526 (2.1); 2.512 (46.0); 2.508 (94.5); 2.503 (127.6); 2.499 (95.5); 2.494 (48.3); 2.335 (0.6); 2.330 (0.8); 2.325 (0.6); 0.146 (0.7); 0.008 (5.7); 0.000 (159.7); −0.008 (7.4); −0.150 (0.7) |
| I-26 | $^1$H-NMR, Solvent [D$_6$]-DMSO, spectrometer: 399.95 MHz:<br>δ = 8.950 (3.9); 8.932 (4.0); 8.422 (5.4); 8.136 (5.9); 8.130 (6.5); 7.945 (0.5); 7.940 (0.5); 7.833 (2.5); 7.827 (2.7); 7.812 (3.8); 7.806 (4.2); 7.729 (7.1); 7.708 (5.0); 7.488 (7.5); 7.340 (3.1); 7.335 (3.5); 7.321 (3.1); 7.316 (3.4); 6.993 (0.4); 6.974 (0.4); 3.911 (0.7); 3.789 (0.3); 3.188 (4.5); 3.171 (16.0); 2.678 (0.4); 2.673 (0.5); 2.509 (55.1); 2.504 (73.4); 2.500 (57.7); 2.331 (0.5); 1.231 (0.6); 0.146 (0.4); 0.007 (3.1); 0.000 (69.5); −0.008 (4.9); −0.150 (0.3). |
| I-27 | $^1$H-NMR, Solvent [D$_6$]-DMSO, spectrometer: 399.95 MHz:<br>δ = 8.953 (1.5); 8.935 (1.5); 8.428 (2.1); 7.649 (2.8); 7.641 (2.9); 7.590 (2.4); 7.568 (2.8); 7.512 (3.1); 7.343 (1.4); 7.339 (1.4); 7.325 (1.4); 7.319 (1.6); 7.317 (1.8); 7.309 (1.4); 7.294 (1.2); 7.287 (1.2); 3.869 (16.0); 3.817 (1.2); 3.188 (1.1); 3.170 (0.4); 2.512 (13.7); 2.508 (27.5); 2.504 (36.5); 2.499 (27.5); 2.495 (14.2); 0.008 (1.5); 0.000 (38.8); −0.008 (2.0). |
| I-28 | $^1$H-NMR, Solvent [D$_6$]-DMSO, spectrometer: 399.95 MHz:<br>δ = 12.426 (0.7); 12.419 (0.7); 8.507 (10.8); 7.837 (11.5); 7.682 (16.0); 3.584 (0.4); 3.467 (0.9); 3.450 (1.7); 3.411 (49.5); 3.235 (0.6); 3.189 (0.3); 3.170 (0.5); 2.673 (0.6); 2.504 (87.0); 2.331 (0.6); 1.074 (0.7); 1.057 (1.3); 1.040 (0.7); 0.000 (47.3). |
| I-29 | $^1$H-NMR, Solvent [D$_6$]-DMSO, spectrometer: 399.95 MHz:<br>δ = 12.271 (2.2); 8.985 (6.6); 8.967 (6.8); 8.438 (9.3); 8.316 (0.4); 7.502 (16.0); 7.364 (5.6); 7.359 (6.3); 7.345 (5.7); 7.340 (6.2); 5.756 (1.0); 3.910 (0.3); 3.339 (4.6); 3.188 (0.4); 3.170 (3.5); 3.152 (1.2); 3.140 (2.6); 3.133 (2.9); 3.121 (5.1); 3.109 (3.3); 3.101 (3.0); 3.089 (1.5); 2.677 (0.5); 2.672 (0.7); 2.668 (0.6); 2.508 (79.9); 2.503 (109.9); 2.499 (89.8); 2.334 (0.5); 2.330 (0.7); 2.326 (0.6); 1.210 (1.8); 1.190 (8.3); 1.178 (10.8); 1.171 (4.4); 1.161 (2.2); 1.149 (4.2); 1.137 (8.2); 1.133 (6.8); 1.118 (8.2); 1.113 (6.6); 1.103 (2.1); 1.099 (1.8); 0.146 (0.5); 0.008 (4.4); 0.000 (109.5); −0.150 (0.5). |
| I-30 | $^1$H-NMR, Solvent [D$_6$]-DMSO, spectrometer: 399.95 MHz:<br>δ = 8.314 (11.9); 7.868 (10.9); 7.795 (6.7); 7.776 (7.6); 7.579 (11.9); 7.575 (12.3); 7.539 (4.0); 7.519 (7.6); 7.489 (7.7); 7.469 (9.8); 7.450 (3.8); 7.438 (0.6); 7.418 (0.5); 7.242 (16.0); 3.332 (14.5); 3.222 (0.4); 3.214 (0.4); 3.170 (2.7); 2.673 (0.9); 2.504 (144.5); 2.331 (1.0); 1.990 (0.3); 1.353 (0.6); 1.337 (1.3); 1.299 (2.8); 1.259 (3.7); 1.250 (2.2); 1.234 (3.2); 1.194 (0.4); 1.188 (0.4); 1.176 (0.4); 0.866 (0.4); 0.853 (0.6); 0.835 (0.4); 0.146 (0.6); 0.000 (121.7); −0.150 (0.7). |
| I-31 | $^1$H-NMR, Solvent [D$_6$]-DMSO, spectrometer: 399.95 MHz:<br>δ = 12.384 (1.0); 8.498 (8.5); 7.841 (9.1); 7.837 (9.3); 7.666 (16.0); 5.756 (0.5); 3.342 (5.5); 3.170 (1.5); 3.156 (2.1); 3.149 (2.4); 3.137 (4.1); 3.125 (2.6); 3.117 (2.4); 3.105 (1.2); 2.673 (0.5); 2.508 (61.3); 2.504 (81.2); 2.499 (63.8); 2.335 (0.4); 2.331 (0.6); 1.225 (1.4); 1.205 (6.7); 1.194 (8.5); 1.185 (3.4); 1.175 (1.7); 1.163 (3.3); 1.152 (6.7); 1.147 (5.2); 1.132 (6.7); 1.127 (5.1); 1.118 (1.6); 1.113 (1.4); 0.146 (0.4); 0.008 (3.2); 0.000 (80.3); −0.150 (0.4). |
| I-32 | $^1$H-NMR, Solvent [D$_6$]-DMSO, spectrometer: 399.95 MHz:<br>δ = 8.442 (4.9); 7.749 (4.7); 7.745 (4.9); 7.540 (5.5); 3.429 (1.5); 3.411 (4.2); 3.392 (4.3); 3.374 (1.8); 3.327 (6.6); 3.170 (0.3); 2.677 (0.3); 2.673 (0.4); 2.668 (0.4); 2.508 (50.2); 2.504 (67.2); 2.499 (52.5); 2.330 (0.4); 1.352 (0.4); 1.337 (0.4); 1.299 (2.5); 1.259 (3.5); 1.250 (7.5); 1.232 (16.0); 1.213 (6.8); 0.008 (2.3); 0.000 (61.5). |

TABLE 3-continued

| Example | NMR data |
|---|---|
| I-33 | $^1$H-NMR, Solvent [D$_6$]-DMSO, spectrometer: 399.95 MHz:<br>δ = 8.932(8.7); 8.914(8.9); 8.401(12.2); 8.383(12.2); 8.378(12.7); 8.314(1.6); 8.109(5.2); 8.105(5.2); 8.088(6.5); 8.084(6.4); 7.934(10.5); 7.913(8.4); 7.889(0.5); 7.442(16.0); 7.319(7.6); 7.314(7.7); 7.301(7.4); 7.296(7.5); 5.754(2.6); 4.341(0.3); 4.290(0.4); 4.281(0.4); 4.274(0.4); 4.222(0.4); 4.210(0.4); 4.172(0.5); 4.159(0.5); 4.027(0.7); 4.004(0.8); 3.910(1.1); 3.900(1.1); 3.799(1.4); 3.773(1.5); 3.735(1.5); 3.690(1.6); 3.655(1.6); 3.643(1.6); 3.586(1.6); 3.572(1.5); 3.494(1.3); 3.188(0.7); 3.111(0.4); 3.081(0.3); 2.676(2.1); 2.672(3.0); 2.667(2.2); 2.525(5.8); 2.511(180.6); 2.507(372.5); 2.503(498.0); 2.498(374.2); 2.494(192.2); 2.334(2.8); 2.329(3.7); 2.325(2.8); 2.241(0.4); 2.193(0.4); 2.182(0.3); 0.146(0.7); 0.008(4.8); 0.000(170.1); −0.008(8.2); −0.150(0.8) |
| I-34 | $^1$H-NMR, Solvent [D$_6$]-DMSO, spectrometer: 399.95 MHz:<br>δ = 8.949(2.6); 8.931(2.9); 8.423(3.7); 8.314(0.4); 7.627(4.8); 7.619(5.3); 7.566(2.5); 7.544(3.1); 7.506(3.4); 7.467(0.3); 7.334(2.2); 7.316(2.3); 7.291(1.7); 7.284(2.0); 7.269(1.6); 7.262(1.8); 4.157(1.9); 4.140(6.1); 4.123(6.2); 4.105(2.2); 3.789(0.4); 3.545(0.4); 3.467(1.1); 3.450(1.7); 3.433(2.1); 3.415(2.1); 3.356(3.6); 3.188(0.5); 2.676(0.7); 2.672(1.0); 2.667(0.8); 2.507(115.4); 2.502(151.2); 2.498(115.3); 2.334(0.7); 2.329(1.0); 2.325(0.7); 1.386(7.7); 1.369(16.0); 1.351(7.5); 1.074(0.7); 1.057(1.3); 1.039(0.7); 0.000(44.7); −0.063 (0.4) |
| I-35 | $^1$H-NMR, Solvent [D$_6$]-DMSO, spectrometer: 399.95 MHz:<br>δ = 8.933(3.6); 8.426(5.2); 7.637(5.6); 7.630(5.9); 7.590(0.5); 7.567(4.7); 7.545(5.6); 7.528(0.6); 7.511(7.4); 7.341(3.1); 7.337(3.1); 7.323(3.1); 7.318(3.1); 7.303(3.1); 7.295(3.0); 7.281(2.6); 7.273(2.5); 5.754(2.2); 4.048(4.4); 4.032(8.9); 4.016(4.5); 3.996(0.4); 3.979(0.5); 2.672(0.9); 2.507(95.2); 2.503(117.9); 2.499(93.4); 2.330(0.7); 1.816(0.6); 1.798(2.5); 1.781(5.0); 1.763(5.2); 1.746(2.8); 1.729(0.8); 1.021(8.1); 1.002(16.0); 0.984(7.5); 0.959(0.4); 0.000(29.5) |
| I-36 | $^1$H-NMR, Solvent [D$_6$]-DMSO, spectrometer: 399.95 MHz:<br>δ = 8.949(2.9); 8.931(3.0); 8.426(4.2); 8.018(5.8); 7.575(12.9); 7.573(12.6); 7.550(0.5); 7.517(6.7); 7.342(2.7); 7.337(2.7); 7.324(2.6); 7.319(2.7); 3.478(0.3); 3.469(0.4); 3.451(0.5); 3.434(0.5); 3.416(0.4); 3.386(0.4); 2.772(1.9); 2.753(5.8); 2.734(6.0); 2.715(2.0); 2.681(0.4); 2.676(0.4); 2.672(0.5); 2.668(0.4); 2.664(0.4); 2.526(1.2); 2.508(57.2); 2.503(75.1); 2.499(57.1); 2.335(0.4); 2.330(0.5); 2.326(0.4); 1.242(7.5); 1.223(16.0); 1.204(7.4); 1.188(0.8); 1.169(0.3); 0.008(0.9); 0.000(24.0); −0.008(1.4) |
| I-37 | $^1$H-NMR, Solvent [D$_6$]-DMSO, spectrometer: 399.95 MHz:<br>δ = 8.948(1.5); 8.929(1.6); 8.427(2.1); 7.749(2.5); 7.727(2.7); 7.694(2.8); 7.686(2.9); 7.526(3.0); 7.339(1.3); 7.334(1.3); 7.321(1.3); 7.316(1.3); 7.230(1.3); 7.222(1.3); 7.208(1.3); 7.200(1.2); 3.864(16.0); 3.815(0.7); 2.671(0.4); 2.507(47.0); 2.502(63.3); 2.498(48.7); 2.329(0.4); 2.324(0.3); 0.008(0.7); 0.000(20.4) |
| I-38 | $^1$H-NMR, Solvent [D$_6$]-DMSO, spectrometer: 399.95 MHz:<br>δ = 8.956(1.8); 8.938(1.9); 8.421(2.7); 7.480(4.2); 7.447(1.2); 7.439(1.6); 7.433(1.6); 7.425(2.3); 7.402(2.2); 7.379(1.6); 7.346(2.4); 7.342(2.4); 7.337(2.1); 7.328(2.5); 7.323(2.5); 7.314(1.1); 7.306(0.5); 3.841(16.0); 3.794(0.5); 3.468(0.4); 3.452(0.5); 3.433(0.5); 3.415(0.5); 3.315(0.3); 2.503(41.5); 0.000(17.2); −0.006(3.9) |
| I-39 | $^1$H-NMR, Solvent [D$_6$]-DMSO, spectrometer: 399.95 MHz:<br>δ = 8.819(1.9); 8.801(2.0); 8.312(1.8); 8.230(2.7); 7.285(1.4); 7.265(3.3); 7.245(2.8); 7.179(2.6); 7.161(1.7); 7.136(2.8); 7.133(2.5); 7.117(2.2); 7.114(1.9); 7.094(1.9); 7.089(1.9); 7.076(1.8); 7.071(1.9); 7.039(4.6); 3.315(324.7); 2.780(0.4); 2.679(1.3); 2.675(2.5); 2.670(3.5); 2.666(2.6); 2.606(0.3); 2.524(9.1); 2.519(14.2); 2.510(184.8); 2.506(377.8); 2.501(509.7); 2.497(380.8); 2.492(190.0); 2.337(1.2); 2.333(2.5); 2.328(3.5); 2.324(2.7); 2.319(1.9); 2.310(16.0); 2.268(0.6); 2.117(0.5); 2.086(0.4); 1.398(1.3); 1.236(0.8); 1.140(1.2); 0.146(1.6); 0.008(11.8); 0.000(354.9); −0.009(13.4); −0.150(1.6) |
| I-40 | $^1$H-NMR, Solvent [D$_6$]-DMSO, spectrometer: 399.95 MHz:<br>δ = 8.943(3.3); 8.925(3.4); 8.427(4.7); 8.314(0.4); 7.665(0.6); 7.543(1.4); 7.522(3.8); 7.505(8.2); 7.489(4.8); 7.471(1.8); 7.426(0.4); 7.403(0.4); 7.384(3.6); 7.381(3.6); 7.365(3.1); 7.362(3.0); 7.335(2.9); 7.317(2.8); 7.312(2.9); 3.468(2.0); 3.450(2.0); 3.433(2.2); 3.415(1.9); 3.345(6.5); 3.220(0.4); 3.187(0.6); 3.030(2.0); 3.012(6.0); 2.994(6.2); 2.975(2.4); 2.956(0.6); 2.946(0.5); 2.937(0.4); 2.927(0.5); 2.671(1.2); 2.667(1.0); 2.507(130.3); 2.502(168.1); 2.498(130.9); 2.334(0.8); 2.329(1.0); 2.325(0.8); 1.279(7.5); 1.261(16.0); 1.242(7.3); 1.190(0.4); 1.172(0.6); 1.121(0.8); 1.074(1.3); 1.056(2.5); 1.039(1.2); 0.146(0.4); 0.008(4.7); 0.000(92.5); −0.149 (0.4) |
| I-41 | $^1$H-NMR, Solvent [D$_6$]-DMSO, spectrometer: 399.95 MHz:<br>δ = 8.944(1.9); 8.925(1.9); 8.429(2.5); 8.313(0.6); 7.636(0.9); 7.590(1.1); 7.569(2.1); 7.539(1.4); 7.520(2.6); 7.511(2.7); 7.501(1.5); 7.486(0.6); 7.464(0.4); 7.445(0.5); 7.424(0.4); 7.407(2.2); 7.387(1.6); 7.377(0.6); 7.357(0.4); 7.328(1.5); 7.310(1.4); 3.714(0.5); 3.697(1.0); 3.681(1.3); 3.665(1.0); 3.649(0.5); 3.622(0.3); 3.589(0.3); 3.467(0.5); 3.449(1.1); 3.432(1.3); 3.414(1.0); 3.331(60.2); 3.187(0.4); 2.675(1.5); 2.670(1.9); 2.666(1.6); 2.506(222.1); 2.502(288.1); 2.497(225.0); 2.333(1.4); 2.328(1.8); 2.324(1.4); 1.282(2.9); 1.265(3.2); 1.250(16.0); 1.234(15.6); 1.197(0.3); 1.123(0.6); 1.073(0.9); 1.056(1.6); 1.038(0.8); 0.146(0.7); 0.000(147.6); −0.150 (0.7) |
| I-42 | $^1$H-NMR, Solvent [D$_6$]-DMSO, spectrometer: 399.95 MHz:<br>δ = 8.841(1.5); 8.822(1.5); 8.268(1.7); 7.144(1.7); 7.128(1.9); 6.449(0.7); 6.430(0.7); 6.223(0.5); 6.201(0.7); 6.177(0.5); 3.639(0.5); 3.624(0.7); 3.610(0.5); 3.316(8.3); 2.675(0.5); 2.671(0.6); 2.666(0.5); 2.524(1.7); 2.511(35.8); 2.506(72.0); 2.502(96.4); 2.497(71.8); 2.493(36.0); 2.333(0.5); 2.328(0.7); 2.324(0.5); 1.398(1.9); 1.236(0.9); 1.171(16.0); 1.156(15.9); 1.141(0.6); 0.008(2.1); 0.000(61.9); −0.008 (2.6) |
| I-43 | $^1$H-NMR, Solvent [D$_6$]-DMSO, spectrometer: 399.95 MHz:<br>δ = 8.951(6.3); 8.933(6.4); 8.427(9.1); 8.314(0.4); 7.937(0.6); 7.741(2.0); 7.727(2.4); 7.720(4.4); 7.707(4.5); 7.700(3.0); 7.686(2.6); 7.539(7.5); 7.519(6.2); 7.496(16.0); 7.471(4.0); 7.468(4.4); 7.446(2.9); 7.345(5.6); 7.340(5.7); 7.326(5.4); 7.321(5.5); 5.754(4.3); 3.910(0.5); 3.753(0.6); 3.700(0.3); 3.619(0.4); 3.602(0.4); 3.562(0.4); 3.538(0.4); 3.525(0.4); 3.483(0.4); 3.432(0.4); 3.420(0.6); 3.303(0.3); 3.188(0.7); 2.676(1.0); 2.672(1.3); 2.668(1.0); 2.507(141.7); 2.503(179.6); 2.499(136.2); 2.334(0.9); 2.330(1.1); 2.325(0.9); 0.146(0.5); 0.008(5.8); 0.000(100.7); −0.150(0.5) |
| I-44 | $^1$H-NMR, Solvent [D$_6$]-DMSO, spectrometer: 399.95 MHz:<br>δ = 8.492(5.7); 8.317(0.3); 7.804(5.8); 7.696(5.8); 7.637(5.9); 7.629(6.0); 7.567(4.0); 7.545(4.6); 7.292(2.6); 7.285(2.7); 7.270(2.3); 7.263(2.2); 4.161(2.4); 4.144(7.1); 4.127(7.2); 4.109(2.4); 3.389(5.9); 3.187(0.5); 3.139(0.4); 2.672(1.3); 2.503(182.1); 2.330(1.2); 1.390(7.9); 1.373(16.0); 1.355(7.8); 0.146(0.4); 0.000(81.2); −0.150(0.4) |
| I-45 | $^1$H-NMR, Solvent [D$_6$]-DMSO, spectrometer: 399.95 MHz:<br>δ = 8.488(6.0); 8.317(0.5); 7.800(6.1); 7.683(5.5); 7.642(6.3); 7.635(6.0); 7.603(1.4); 7.558(3.9); 7.537(4.4); 7.509(0.7); 7.467(0.7); 7.461(0.6); 7.292(3.0); 7.286(2.9); 7.270(2.6); 7.184(0.3); 4.102(0.4); 4.048(5.3); 4.032(9.3); 4.016(5.0); 3.995(1.1); 3.978(1.3); 3.962(0.8); 3.934(0.4); 3.913(0.4); 3.868(0.4); 3.844(0.5); 3.780(0.6); 3.764(0.6); 3.665(0.9); 3.356(141.1); 3.162(1.4); 3.024(0.6); 2.997(0.5); 2.992(0.5); 2.987(0.5); 2.954(0.5); 2.927(0.4); 2.898(0.4); 2.884(0.5); 2.879(0.4); 2.824(0.6); 2.798(0.6); 2.788(0.6); 2.673(0.8); 2.503(352.2); 2.330(2.5); 1.818(6.0); 1.801(3.1); 1.783(5.8); 1.766(6.0); 1.749(3.6); 1.732(1.4); 1.073(0.5); 1.056(1.0); 1.023(8.7); 1.005(16.0); 0.987(8.0); 0.958(1.0); 0.147(0.4); 0.000(56.5); −0.149(0.3) |
| I-46 | $^1$H-NMR, Solvent [D$_6$]-DMSO, spectrometer: 399.95 MHz:<br>δ = 8.217(5.3); 8.214(5.7); 8.198(5.8); 8.195(6.0); 8.114(10.2); 8.109(10.5); 7.752(1.7); 7.734(4.7); 7.717(5.0); 7.714(5.0); 7.691(9.1); 7.674(4.3); 7.665(4.7); 7.642(14.6); 7.637(10.9); 7.628(3.1); 7.423(16.0); 5.759(1.4); 3.426(1.2); 2.674(0.8); 2.508(85.6); 2.505(105.9); 2.331(0.7); 0.000(11.3) |

TABLE 3-continued

| Example | NMR data |
|---|---|
| I-47 | $^1$H-NMR, Solvent [D$_6$]-DMSO, spectrometer: 399.95 MHz:<br>δ = 8.317(1.3); 8.121(14.7); 8.115(15.2); 8.089(15.8); 8.084(16.0); 7.944(0.4); 7.938(0.4); 7.807(5.0); 7.801(5.4); 7.785(7.4); 7.779(7.3); 7.706(14.9); 7.684(9.4); 7.614(13.3); 7.608(13.2); 7.346(14.6); 5.758(3.4); 4.038(0.4); 4.036(0.4); 4.028(0.4); 3.979(0.5); 3.964(0.5); 3.911(0.9); 3.834(0.9); 3.767(1.2); 3.749(1.3); 3.699(1.8); 3.443(11.8); 3.187(2.1); 3.138(1.4); 3.110(1.3); 3.064(0.9); 2.944(0.5); 2.933(0.4); 2.867(0.3); 2.676(2.8); 2.672(4.0); 2.668(2.9); 2.525(8.0); 2.507(470.0); 2.503(614.4); 2.499(452.7); 2.377(0.7); 2.366(0.7); 2.334(3.4); 2.330(4.4); 2.325(3.4); 2.275(0.5); 2.200(0.4); 2.180(0.4); 2.161(0.3); 0.146(0.3); 0.008(2.4); 0.000(77.5); −0.008(3.3); −0.149(0.4) |
| I-48 | $^1$H-NMR, Solvent [D$_6$]-DMSO, spectrometer: 399.95 MHz:<br>δ = 8.114(7.9); 8.109(8.2); 7.697(5.7); 7.693(6.8); 7.675(16.0); 7.637(11.2); 7.620(4.1); 7.614(3.2); 7.598(2.0); 7.413(11.5); 5.759(2.4); 3.912(0.5); 3.695(0.3); 3.683(0.3); 3.644(0.4); 3.632(0.4); 3.617(0.4); 3.573(0.4); 3.562(0.4); 3.537(0.4); 3.491(0.4); 3.411(0.3); 2.673(0.7); 2.508(73.9); 2.505(92.5); 2.331(0.6); 0.000(10.2) |
| I-49 | $^1$H-NMR, Solvent [D$_6$]-DMSO, spectrometer: 399.95 MHz:<br>δ = 8.113(2.9); 8.108(2.9); 7.651(3.0); 7.642(4.5); 7.636(2.8); 7.595(2.3); 7.573(2.7); 7.418(4.0); 7.320(1.4); 7.313(1.4); 7.298(1.2); 7.291(1.2); 3.871(16.0); 3.724(0.5); 3.450(0.5); 3.432(0.6); 3.415(0.5); 3.392(0.5); 3.375(0.4); 3.360(0.4); 2.508(32.3); 2.504(41.1); 2.500(30.4); 0.000(3.0) |
| I-50 | $^1$H-NMR, Solvent [D$_6$]-DMSO, spectrometer: 399.95 MHz:<br>δ = 9.353(1.8); 8.057(1.3); 8.034(1.5); 7.648(2.8); 7.640(2.9); 7.595(2.3); 7.580(1.4); 7.573(3.1); 7.556(1.2); 7.553(1.3); 7.414(2.9); 7.319(1.4); 7.311(1.3); 7.297(1.2); 7.289(1.1); 3.869(16.0); 3.816(0.5); 3.723(0.6); 3.467(0.8); 3.449(1.3); 3.432(1.6); 3.414(1.5); 3.395(1.5); 2.677(0.3); 2.672(0.4); 2.668(0.3); 2.526(1.1); 2.521(1.6); 2.512(23.4); 2.508(48.0); 2.503(63.1); 2.499(45.5); 2.494(21.7); 2.330(0.4); 1.074(0.5); 1.056(1.1); 1.038(0.5); 0.000(4.6) |
| I-51 | $^1$H-NMR, Solvent [D$_6$]-DMSO, spectrometer: 399.95 MHz:<br>δ = 9.343(10.6); 8.317(0.8); 8.131(13.9); 8.125(14.7); 8.047(7.5); 8.023(8.3); 7.943(0.8); 7.938(0.8); 7.827(5.6); 7.820(5.5); 7.805(8.7); 7.799(9.5); 7.725(16.0); 7.712(1.6); 7.704(11.9); 7.681(0.3); 7.613(0.5); 7.607(0.7); 7.570(7.2); 7.567(7.3); 7.546(6.5); 7.543(6.7); 7.471(0.4); 7.464(0.4); 7.402(0.7); 7.377(15.8); 4.078(0.4); 4.022(0.4); 3.948(0.6); 3.912(0.9); 3.810(1.0); 3.800(1.1); 3.671(2.1); 3.491(4.2); 3.467(5.1); 3.449(7.1); 3.432(7.0); 3.415(4.6); 3.301(2.0); 3.187(1.5); 3.137(0.9); 3.110(0.8); 3.066(0.6); 3.027(0.5); 2.994(0.5); 2.961(0.4); 2.944(0.4); 2.920(0.3); 2.910(0.3); 2.796(0.4); 2.784(0.3); 2.772(0.3); 2.677(1.6); 2.672(2.2); 2.668(1.7); 2.526(4.0); 2.512(116.4); 2.508(242.8); 2.503(325.9); 2.499(244.8); 2.495(126.3); 2.378(0.5); 2.334(1.8); 2.330(2.4); 2.326(1.9); 1.073(3.2); 1.056(6.3); 1.038(3.1); 0.008(0.6); 0.000(20.7); −0.009(1.0) |
| I-52 | $^1$H-NMR, Solvent [D$_6$]-DMSO, spectrometer: 399.95 MHz:<br>δ = 9.332(6.6); 8.318(0.3); 8.056(4.5); 8.032(5.0); 7.691(5.5); 7.687(6.8); 7.669(16.0); 7.631(6.1); 7.614(4.0); 7.608(3.4); 7.591(2.2); 7.578(4.4); 7.575(4.5); 7.554(3.9); 7.551(4.1); 7.400(9.2); 3.467(1.9); 3.450(3.3); 3.432(3.3); 3.415(1.8); 3.188(0.4); 2.677(0.8); 2.673(1.1); 2.668(0.7); 2.508(121.4); 2.504(158.5); 2.499(119.6); 2.335(0.8); 2.330(1.1); 2.326(0.9); 1.074(2.2); 1.056(4.3); 1.039(2.1); 0.146(0.4); 0.008(3.2); 0.000(79.6); −0.008(3.9); −0.150(0.4) |
| I-53 | $^1$H-NMR, Solvent [D$_6$]-DMSO, spectrometer: 399.95 MHz:<br>δ = 8.319(0.4); 8.184(6.5); 8.161(7.0); 8.141(10.6); 8.135(10.8); 7.944(0.7); 7.939(0.7); 7.835(3.9); 7.829(3.9); 7.814(5.9); 7.808(6.0); 7.730(16.0); 7.713(8.8); 7.709(9.7); 7.522(11.1); 7.477(4.5); 7.455(5.4); 7.436(3.7); 5.759(0.3); 3.915(1.2); 3.808(0.6); 3.642(0.7); 3.603(0.7); 3.528(0.7); 3.498(0.7); 3.468(0.7); 3.450(0.8); 3.433(0.7); 3.415(0.6); 3.314(0.5); 3.217(0.3); 3.187(0.4); 2.673(1.4); 2.508(170.4); 2.504(215.9); 2.500(164.9); 2.434(0.4); 2.335(1.1); 2.331(1.5); 2.327(1.2); 1.056(0.4); 0.146(0.5); 0.000(108.8); −0.150(0.5) |
| I-54 | $^1$H-NMR, Solvent [D$_6$]-DMSO, spectrometer: 399.95 MHz:<br>δ = 9.450(5.2); 9.447(5.4); 7.941(0.5); 7.930(0.4); 7.856(6.4); 7.853(6.7); 7.251(6.8); 6.975(0.3); 5.758(0.7); 5.666(0.3); 5.584(0.5); 5.556(0.5); 5.539(0.5); 5.523(0.5); 5.516(0.5); 5.507(0.5); 5.390(0.3); 3.930(0.8); 3.217(1.6); 3.187(2.4); 2.795(0.5); 2.783(0.7); 2.677(0.3); 2.673(0.5); 2.669(0.4); 2.526(1.1); 2.513(29.2); 2.508(59.6); 2.504(79.9); 2.499(60.9); 2.495(31.5); 2.335(0.4); 2.331(0.6); 2.326(0.4); 2.060(7.3); 2.013(16.0); 1.986(0.9); 1.965(8.2); 1.939(1.6); 1.892(0.9); 1.233(0.5); 0.008(2.4); 0.000(70.7); −0.008(3.0); −0.150(0.3) |
| I-55 | $^1$H-NMR, Solvent [D$_6$]-DMSO, spectrometer: 399.95 MHz:<br>δ = 9.446(5.0); 9.444(5.1); 8.232(0.7); 8.217(1.1); 8.213(1.1); 8.198(0.7); 7.928(0.5); 7.776(6.4); 7.774(6.4); 6.995(8.6); 6.973(1.4); 6.237(0.6); 6.175(0.4); 3.930(1.3); 3.217(1.6); 3.186(16.0); 2.796(0.8); 2.785(1.1); 2.773(0.5); 2.678(0.4); 2.673(0.5); 2.669(0.4); 2.509(58.3); 2.504(75.8); 2.500(57.3); 2.336(0.4); 2.331(0.5); 2.327(0.4); 2.209(0.7); 1.233(0.5); 0.839(0.4); 0.008(2.5); 0.000(58.2) |
| I-56 | $^1$H-NMR, Solvent [D$_6$]-DMSO, spectrometer: 399.95 MHz:<br>δ = 8.383(9.3); 8.379(10.0); 8.314(0.6); 8.211(0.5); 8.103(4.2); 8.082(16.0); 8.077(13.9); 8.011(0.3); 7.931(8.0); 7.910(6.4); 7.889(1.1); 7.606(9.2); 7.601(9.7); 7.339(13.9); 5.755(12.2); 4.255(0.3); 4.102(0.3); 4.072(0.4); 4.036(0.4); 3.910(0.6); 2.672(2.0); 2.667(1.6); 2.507(232.8); 2.503(307.9); 2.498(237.4); 2.329(2.1); 2.325(1.6); 2.086(0.9); 0.146(1.6); 0.008(13.3); 0.000(335.9); −0.150(1.6) |
| I-57 | $^1$H-NMR, Solvent [D$_6$]-DMSO, spectrometer: 399.95 MHz:<br>δ = 8.109(5.9); 8.103(6.0); 7.634(6.9); 7.630(9.5); 7.623(6.5); 7.571(4.9); 7.549(5.7); 7.414(8.5); 7.297(2.9); 7.289(2.8); 7.275(2.5); 7.267(2.4); 4.160(2.2); 4.143(7.1); 4.126(7.1); 4.108(2.1); 3.468(0.4); 3.451(0.8); 3.433(0.8); 3.416(0.4); 2.677(0.5); 2.672(0.7); 2.667(0.5); 2.525(2.3); 2.507(70.9); 2.503(92.7); 2.499(69.3); 2.334(0.4); 2.330(0.5); 2.326(0.4); 1.388(7.7); 1.370(16.0); 1.353(7.5); 1.074(0.5); 1.057(1.0); 1.039(0.5); 0.146(0.5); 0.008(4.1); 0.000(94.2); −0.008(4.4); −0.150(0.5) |
| I-58 | $^1$H-NMR, Solvent [D$_6$]-DMSO, spectrometer: 399.95 MHz:<br>δ = 8.108(5.2); 8.103(5.3); 7.638(6.2); 7.633(6.3); 7.630(8.5); 7.567(4.2); 7.545(4.9); 7.412(7.0); 7.304(2.5); 7.296(2.4); 7.282(2.1); 7.274(2.0); 4.048(3.9); 4.032(8.1); 4.016(4.0); 3.910(0.6); 3.552(0.5); 3.544(0.7); 3.512(0.4); 3.472(0.5); 3.450(0.6); 3.433(0.6); 3.415(0.5); 3.404(0.5); 3.391(0.5); 3.355(0.4); 2.676(0.6); 2.671(0.8); 2.667(0.6); 2.563(0.5); 2.524(2.5); 2.511(44.3); 2.507(87.8); 2.502(116.5); 2.498(87.0); 2.333(0.5); 2.329(0.7); 2.324(0.5); 1.816(0.5); 1.798(2.1); 1.781(4.3); 1.763(4.5); 1.746(2.3); 1.728(0.6); 1.021(7.8); 1.002(16.0); 0.984(7.2); 0.146(0.7); 0.008(5.3); 0.000(136.6); −0.008(6.4); −0.150 (0.6) |
| I-59 | $^1$H-NMR, Solvent [D$_6$]-DMSO, spectrometer: 399.95 MHz:<br>δ = 8.110(6.1); 8.106(6.1); 8.022(7.1); 7.635(5.8); 7.630(5.6); 7.578(15.6); 7.551(0.7); 7.526(0.3); 7.426(9.1); 3.911(0.4); 2.773(2.3); 2.754(6.8); 2.735(6.9); 2.716(2.5); 2.673(0.7); 2.503(82.6); 2.330(0.5); 1.244(8.0); 1.225(16.0); 1.206(8.0); 1.188(0.9); 1.169(0.4); 0.146(0.4); 0.000(71.1); −0.150(0.4) |
| I-60 | $^1$H-NMR, Solvent [D$_6$]-DMSO, spectrometer: 399.95 MHz:<br>δ = 8.106(3.0); 8.101(3.0); 7.943(3.1); 7.941(3.1); 7.632(2.9); 7.627(2.8); 7.611(0.6); 7.591(6.9); 7.565(0.3); 7.406(4.1); 5.754(0.4); 2.672(0.4); 2.574(16.0); 2.503(49.8); 0.000(37.7) |

TABLE 3-continued

| Example | NMR data |
|---|---|
| I-61 | ¹H-NMR, Solvent [D₆]-DMSO, spectrometer: 399.95 MHz:<br>δ = 8.116(6.3); 8.111(6.6); 7.634(6.2); 7.629(6.2); 7.552(1.4); 7.532(4.2); 7.513(4.9); 7.498(5.2); 7.480(2.0); 7.447(0.5); 7.427(9.7); 7.391(4.1); 7.375(3.1); 7.372(3.2); 5.754(6.1); 3.532(0.3); 3.415(0.7); 3.036(2.1); 3.018(6.6); 3.000(6.9); 2.981(2.5); 2.962(0.5); 2.673(0.6); 2.507(70.3); 2.503(91.6); 2.499(72.0); 2.330(0.6); 1.285(7.6); 1.267(16.0); 1.248(7.4); 1.203(0.4); 1.185(0.7); 1.166(0.3); 1.121(0.5); 0.146(0.4); 0.000(78.0); −0.150(0.4) |
| I-62 | ¹H-NMR, Solvent [D₆]-DMSO, spectrometer: 399.95 MHz:<br>δ = 8.495(5.1); 8.031(6.3); 7.808(5.6); 7.804(5.2); 7.718(7.6); 7.580(13.9); 3.468(0.4); 3.464(0.3); 3.451(0.5); 3.434(0.4); 2.777(2.1); 2.758(6.3); 2.739(6.5); 2.721(2.2); 2.672(0.7); 2.508(72.2); 2.503(89.0); 2.500(66.1); 2.330(0.5); 1.248(7.8); 1.229(16.0); 1.211(7.4); 0.146(0.4); 0.000(75.6); −0.149(0.4) |
| I-63 | ¹H-NMR, Solvent [D₆]-DMSO, spectrometer: 399.95 MHz:<br>δ = 8.495(5.0); 8.314(0.6); 7.799(5.2); 7.795(5.0); 7.704(4.9); 7.545(1.1); 7.525(3.3); 7.506(4.0); 7.494(4.3); 7.475(1.6); 7.388(3.3); 7.370(2.7); 3.584(0.4); 3.467(2.0); 3.450(3.8); 3.432(4.5); 3.414(4.3); 3.377(6.0); 3.188(0.6); 3.173(0.3); 3.033(2.0); 3.015(6.0); 2.997(6.1); 2.979(2.3); 2.964(0.6); 2.675(1.5); 2.671(2.0); 2.667(1.5); 2.557(0.5); 2.506(225.3); 2.502(288.0); 2.498(213.5); 2.333(1.3); 2.329(1.8); 2.324(1.4); 1.286(7.5); 1.268(16.0); 1.250(7.3); 1.207(0.5); 1.189(0.8); 1.170(0.4); 1.120(1.0); 1.074(2.0); 1.056(3.9); 1.039(1.9); 0.146(1.2); 0.008(11.4); 0.000(254.1); −0.041(0.3); −0.150(1.3) |
| I-64 | ¹H-NMR, Solvent [D₆]-DMSO, spectrometer: 399.95 MHz:<br>δ = 8.507(3.4); 7.810(3.6); 7.726(4.4); 7.637(0.4); 7.609(1.5); 7.589(2.7); 7.556(1.7); 7.537(2.6); 7.517(1.3); 7.425(2.6); 7.406(2.0); 5.755(1.5); 3.729(0.5); 3.712(1.2); 3.696(1.6); 3.679(1.3); 3.663(0.6); 3.468(1.2); 3.451(1.9); 3.433(2.1); 3.415(1.9); 3.272(0.4); 2.672(0.5); 2.503(83.0); 2.330(0.6); 1.296(1.1); 1.282(1.0); 1.257(16.0); 1.240(15.8); 1.212(0.5); 1.196(0.4); 1.124(0.6); 1.074(0.8); 1.057(1.4); 1.039(0.7); 0.000(57.8) |
| I-65 | ¹H-NMR, Solvent [D₆]-DMSO, spectrometer: 399.95 MHz:<br>δ = 8.490(10.5); 8.314(0.4); 7.805(11.1); 7.802(11.2); 7.741(2.0); 7.727(2.3); 7.720(4.5); 7.707(4.7); 7.700(3.2); 7.678(16.0); 7.540(7.8); 7.520(6.4); 7.496(3.8); 7.469(4.5); 7.447(3.2); 5.755(1.1); 3.468(0.4); 3.451(0.9); 3.433(0.9); 3.416(0.5); 2.819(0.5); 2.807(0.5); 2.672(1.1); 2.508(139.7); 2.503(183.9); 2.499(141.7); 2.334(1.0); 2.330(1.3); 1.075(0.7); 1.057(1.3); 1.040(0.7); 0.146(0.8); 0.008(6.5); 0.000(165.8); −0.150(0.9) |
| I-66 | ¹H-NMR, Solvent [D₆]-DMSO, spectrometer: 399.95 MHz:<br>δ = 8.106(3.1); 8.101(3.2); 7.633(3.0); 7.627(3.0); 7.412(0.6); 7.398(5.5); 7.374(1.1); 7.353(0.6); 6.682(1.8); 6.659(1.7); 6.429(1.0); 6.409(1.0); 6.401(1.1); 6.381(1.0); 3.809(0.4); 3.794(0.9); 3.778(1.3); 3.763(0.9); 3.747(0.4); 2.507(30.2); 2.503(39.9); 2.499(30.0); 1.397(1.7); 1.238(16.0); 1.223(15.0); 0.008(1.5); 0.000(38.9); −0.008(1.8) |
| I-67 | ¹H-NMR, Solvent [D₆]-DMSO, spectrometer: 399.95 MHz:<br>δ = 8.104(10.4); 7.937(0.4); 7.746(1.7); 7.733(1.9); 7.726(3.8); 7.712(3.9); 7.705(2.6); 7.691(2.3); 7.637(9.6); 7.632(9.5); 7.544(6.3); 7.524(5.2); 7.500(3.0); 7.476(3.2); 7.473(3.6); 7.451(2.6); 7.398(16.0); 5.754(2.1); 2.677(0.4); 2.673(0.6); 2.668(0.4); 2.526(0.8); 2.512(40.9); 2.508(84.3); 2.504(113.5); 2.499(86.9); 2.335(0.7); 2.330(0.9); 2.326(0.7); 0.146(0.5); 0.008(3.9); 0.000(123.8); −0.008(7.9); −0.037(0.5); −0.052(0.4); −0.150(0.7) |
| I-68 | ¹H-NMR, Solvent [D₆]-DMSO, spectrometer: 399.95 MHz:<br>δ = 8.095(2.5); 8.090(2.6); 7.629(2.2); 7.624(2.2); 7.445(1.1); 7.437(1.3); 7.431(1.3); 7.423(1.3); 7.414(0.7); 7.391(1.6); 7.367(1.2); 7.351(3.0); 7.334(0.7); 7.325(1.2); 7.316(0.7); 7.302(0.6); 7.293(0.3); 3.839(16.0); 3.793(0.6); 3.401(1.1); 2.671(0.8); 2.506(95.4); 2.502(125.8); 2.498(95.5); 2.329(0.8); 0.008(2.1); 0.000(59.1) |
| I-69 | ¹H-NMR, Solvent [D₆]-DMSO, spectrometer: 399.95 MHz:<br>δ = 8.113(2.9); 8.108(3.0); 7.754(2.6); 7.732(2.8); 7.698(2.9); 7.690(3.1); 7.635(2.7); 7.630(2.8); 7.444(4.4); 7.237(1.4); 7.229(1.4); 7.215(1.3); 7.207(1.3); 3.867(16.0); 3.816(0.6); 3.451(0.5); 3.434(0.5); 2.525(0.4); 2.508(24.3); 2.503(32.4); 2.499(24.8); 1.075(0.4); 1.057(0.8); 1.040(0.4); 0.008(0.6); 0.000(17.3) |
| I-70 | ¹H-NMR, Solvent [D₆]-DMSO, spectrometer: 399.95 MHz:<br>δ = 8.493(2.4); 7.802(2.6); 7.798(2.5); 7.750(2.3); 7.728(3.6); 7.724(3.5); 7.705(2.9); 7.697(2.9); 7.232(1.3); 7.224(1.2); 7.210(1.2); 7.202(1.1); 3.868(16.0); 3.815(0.4); 3.510(0.3); 3.468(0.5); 3.450(0.7); 3.433(0.7); 3.415(0.4); 2.676(0.4); 2.672(0.5); 2.507(55.4); 2.502(71.2); 2.498(52.8); 2.333(0.4); 2.329(0.5); 1.074(0.3); 1.057(0.7); 1.039(0.3); 0.008(1.4); 0.000(34.9) |
| I-71 | ¹H-NMR, Solvent [D₆]-DMSO, spectrometer: 399.95 MHz:<br>δ = 8.495(13.7); 8.314(0.9); 7.802(15.6); 7.755(0.8); 7.742(2.2); 7.724(2.0); 7.707(16.0); 7.662(0.5); 7.636(0.4); 7.576(4.5); 7.555(10.3); 7.535(7.6); 7.517(1.1); 7.508(1.4); 7.488(0.8); 7.478(5.6); 7.448(10.1); 7.427(7.2); 7.389(10.5); 7.370(8.4); 7.246(1.8); 7.226(1.5); 3.796(0.4); 3.723(0.5); 3.467(4.4); 3.450(6.4); 3.432(6.9); 3.415(5.7); 3.187(0.8); 3.181(0.7); 3.107(0.4); 3.090(0.5); 3.073(0.4); 3.062(0.4); 3.027(0.3); 3.020(0.3); 3.000(0.5); 2.983(0.5); 2.962(0.5); 2.942(0.5); 2.926(0.4); 2.777(3.3); 2.730(0.6); 2.671(3.1); 2.506(348.8); 2.502(438.0); 2.486(82.2); 2.452(10.9); 2.419(1.1); 2.329(2.8); 2.310(0.4); 1.411(0.3); 1.296(2.2); 1.258(0.3); 1.236(0.3); 1.118(2.0); 1.100(0.4); 1.074(2.0); 1.056(4.0); 1.039(2.0); 0.851(0.4); 0.832(0.6); 0.643(0.6); 0.146(0.9); 0.000(176.5); −0.150(1.0) |
| I-72 | ¹H-NMR, Solvent [D₆]-DMSO, spectrometer: 399.95 MHz:<br>δ = 8.475(10.5); 8.400(9.4); 8.396(9.8); 8.126(4.4); 8.121(4.4); 8.105(5.3); 8.100(5.2); 7.948(8.4); 7.927(6.7); 7.891(0.4); 7.789(11.5); 7.785(10.7); 7.652(16.0); 5.755(4.7); 2.674(0.8); 2.670(0.6); 2.509(89.5); 2.505(118.2); 2.501(91.8); 2.336(0.5); 2.332(0.7); 2.328(0.6); 0.008(2.4); 0.000(62.1); −0.150(0.3) |
| I-73 | ¹H-NMR, Solvent [D₆]-DMSO, spectrometer: 399.95 MHz:<br>δ = 8.933(8.1); 8.914(8.2); 8.409(12.0); 8.403(14.4); 8.397(12.1); 8.314(0.6); 8.119(7.6); 8.098(10.6); 7.998(6.5); 7.993(6.5); 7.977(4.7); 7.972(4.6); 7.863(0.4); 7.476(16.0); 7.326(7.0); 7.321(7.1); 7.307(6.8); 7.302(6.8); 5.755(0.4); 4.202(0.3); 4.172(0.3); 4.146(0.3); 4.131(0.3); 4.119(0.3); 4.098(0.4); 4.078(0.4); 4.061(0.4); 4.055(0.4); 4.042(0.4); 4.036(0.4); 4.029(0.4); 4.018(0.4); 3.993(0.4); 3.969(0.4); 3.921(0.4); 3.910(0.4); 3.874(0.4); 3.851(0.4); 3.844(0.4); 3.826(0.4); 3.816(0.4); 3.804(0.4); 3.797(0.4); 3.773(0.4); 3.755(0.3); 3.742(0.3); 2.677(1.1); 2.672(1.6); 2.668(1.1); 2.508(214.1); 2.503(282.4); 2.499(213.8); 2.334(1.6); 2.330(2.1); 2.326(1.7); 0.146(0.6); 0.008(5.0); 0.000(142.6); −0.007(9.3); −0.045(0.4); −0.150(0.8) |
| I-74 | ¹H-NMR, Solvent [D₆]-DMSO, spectrometer: 399.95 MHz:<br>δ = 8.486(2.6); 7.812(2.8); 7.808(2.7); 7.663(4.2); 7.461(1.1); 7.453(1.5); 7.447(1.4); 7.439(1.4); 7.431(0.9); 7.408(2.0); 7.384(1.4); 7.351(0.8); 7.342(1.4); 7.334(0.9); 7.320(0.8); 7.311(0.4); 3.847(16.0); 3.469(1.4); 3.452(4.0); 3.434(4.1); 3.417(1.4); 2.508(24.8); 2.504(31.5); 2.500(24.5); 1.075(4.0); 1.058(7.8); 1.040(3.9); 0.000(14.3) |
| I-75 | ¹H-NMR, Solvent [D₆]-DMSO, spectrometer: 399.95 MHz:<br>δ = 8.314(0.4); 8.089(4.0); 8.084(4.1); 8.051(0.5); 8.046(0.6); 8.008(1.0); 8.003(1.1); 7.894(3.7); 7.869(0.4); 7.633(3.8); 7.628(3.9); 7.611(1.0); 7.605(1.0); 7.454(1.6); 7.435(2.1); 7.340(5.2); 7.327(3.2); 7.307(2.5); 7.241(0.9); 7.198(1.8); 4.850(0.4); 4.841(0.4); 4.795(0.4); 4.779(0.4); 3.432(0.4); 3.341(8.7); 3.022(0.4); 3.003(0.4); 2.718(1.3); 2.699(4.1); 2.680(4.5); 2.661(1.9); 2.639(0.4); 2.621(0.4); 2.585(16.0); 2.536(1.8); 2.506(140.2); 2.502(179.5); 2.498(138.6); 2.382(1.4); 2.329(1.2); 1.228(5.6); 1.209(11.7); 1.190(5.5); 1.160(0.5); 1.141(0.9); 1.122(0.4); 0.146(0.9); 0.000(172.1); −0.150(0.9) |

TABLE 3-continued

| Example | NMR data |
|---|---|
| I-76 | ¹H-NMR, Solvent [D₆]-DMSO, spectrometer: 399.95 MHz:<br>δ = 8.314(0.6); 8.126(0.5); 8.111(12.1); 8.106(11.7); 7.682(0.4); 7.631(11.5); 7.626(10.9); 7.588(0.3); 7.575(3.8); 7.555(8.7); 7.535(6.4); 7.523(1.4); 7.514(1.1); 7.506(0.7); 7.500(0.5); 7.485(0.4); 7.480(0.4); 7.472(0.4); 7.445(8.8); 7.432(3.2); 7.418(16.0); 7.389(8.1); 7.370(6.6); 7.262(0.4); 7.243(0.7); 7.222(0.7); 5.754(3.1); 3.911(1.2); 3.719(0.3); 3.622(0.6); 3.613(0.6); 3.605(0.7); 3.468(3.2); 3.450(6.6); 3.433(6.7); 3.415(3.2); 3.257(0.5); 3.187(0.4); 2.981(0.4); 2.770(4.2); 2.676(1.4); 2.672(1.9); 2.667(1.5); 2.622(0.6); 2.507(200.9); 2.503(263.6); 2.498(198.7); 2.484(50.9); 2.451(3.7); 2.426(0.4); 2.413(0.4); 2.333(1.2); 2.329(1.6); 2.325(1.2); 1.292(2.3); 1.234(0.7); 1.118(0.9); 1.074(5.0); 1.057(9.9); 1.039(4.9); 0.855(0.4); 0.850(0.4); 0.831(0.6); 0.146(1.3); 0.008(10.9); 0.000(273.2); −0.008(14.3); −0.150(1.3) |
| I-77 | ¹H-NMR, Solvent [D₆]-DMSO, spectrometer: 399.95 MHz:<br>δ = 8.473(4.4); 8.374(0.4); 7.914(4.3); 7.889(0.6); 7.802(4.9); 7.766(0.5); 7.645(6.4); 7.526(0.3); 7.480(0.9); 7.463(2.2); 7.445(2.6); 7.364(0.5); 7.336(3.3); 7.316(2.5); 3.474(0.3); 3.455(0.4); 3.437(0.4); 3.420(0.3); 3.036(0.4); 3.017(0.4); 2.725(1.7); 2.706(4.3); 2.687(4.5); 2.669(1.9); 2.637(0.5); 2.598(16.0); 2.506(30.8); 2.390(1.5); 1.234(5.4); 1.216(10.3); 1.197(5.1); 1.168(0.6); 1.150(0.9); 1.131(0.5); 0.000(9.3) |
| I-78 | ¹H-NMR, Solvent [D₆]-DMSO, spectrometer: 399.95 MHz:<br>δ = 8.892(0.8); 8.874(0.8); 8.322(1.0); 7.824(1.2); 7.689(4.2); 7.664(0.4); 7.337(0.9); 7.329(1.8); 7.325(2.0); 7.305(4.7); 7.297(8.0); 7.275(4.9); 7.255(2.6); 7.213(1.1); 3.311(10.9); 2.954(0.4); 2.935(0.4); 2.683(0.6); 2.665(2.0); 2.659(2.1); 2.640(5.1); 2.621(5.0); 2.602(1.7); 2.550(6.7); 2.538(20.3); 2.505(46.4); 2.501(60.9); 2.497(46.5); 2.348(0.5); 2.327(1.9); 2.085(1.1); 1.398(1.6); 1.353(0.3); 1.336(0.8); 1.259(0.5); 1.250(1.1); 1.236(2.6); 1.219(2.7); 1.208(1.1); 1.200(11.5); 1.190(1.9); 1.182(16.0); 1.163(6.6); 1.101(0.4); 0.008(0.5); 0.000(11.0) |

Intermediates of Compounds of General Formula (II):

TABLE 4

(II)

$Z = O$ and $R^2 = H$

| Example | R¹ | n | Remarks | Code | BCS |
|---|---|---|---|---|---|
| II-1 | 4-Cl, 6-CF₃ | 2 | NMR | | |
| II-2 | 5-CF₃, 7-Cl | 2 | NMR | | |
| II-3 | 5-CF₃ | 1 | NMR | | |
| II-4 | 5-Cl, 7-Cl | 2 | NMR | MKH24284-1-1 | BCS-CY75362 neu |
| II-5 | 6-CF₃ | 1 | NMR | MKH24306-1-1 | BCS-CY80142 neu |
| II-6 | 7-CF₃ | 1 | NMR | MKH24442-1-1 | BCS-CY80139 neu |

¹H-NMR Data of Compounds of General Formula (II):

TABLE 5

| Example | NMR data |
|---|---|
| II-1 | ¹H-NMR, Solvent [D₆]-DMSO, spectrometer: 399.95 MHz:<br>δ = 13.593 (1.6); 9.518 (9.9); 9.516 (9.9); 9.434 (0.7); 8.316 (0.9); 8.006 (0.6); 7.983 (0.6); 7.895 (12.7); 7.893 (12.9); 7.542 (0.5); 7.538 (0.5); 7.518 (0.5); 7.514 (0.5); 7.240 (16.0); 7.219 (1.3); 3.860 (0.6); 3.411 (0.5); 3.322 (104.5); 2.676 (2.2); 2.671 (3.0); 2.667 (2.2); 2.524 (8.0); 2.511 (162.5); 2.507 (325.3); 2.502 (433.9); 2.498 (320.4); 2.493 (156.8); 2.333 (2.1); 2.329 (2.9); 2.324 (2.1); 0.146 (0.9); 0.008 (7.2); 0.000 (210.4); −0.008 (7.1); −0.150 (0.9) |
| II-2 | ¹H-NMR, Solvent [D₆]-DMSO, spectrometer: 399.95 MHz:<br>δ = 8.535 (1.2); 8.420 (7.8); 7.939 (1.4); 7.934 (1.5); 7.783 (9.0); 7.778 (9.4); 7.480 (16.0); 5.758 (0.6); 2.676 (0.4); 2.529 (1.1); 2.515 (23.3); 2.511 (47.4); 2.507 (63.9); 2.502 (49.8); 2.498 (27.4); 2.333 (0.4); 1.912 (0.4); 1.230 (0.6); 0.146 (0.3); 0.008 (2.8); 0.000 (73.5); −0.150 (0.3) |
| II-3 | ¹H-NMR, Solvent [D₆]-DMSO, spectrometer: 399.95 MHz:<br>δ = 13.387 (0.4); 13.332 (0.8); 13.258 (0.3); 8.986 (6.5); 8.967 (6.7); 8.383 (0.3); 8.361 (9.3); 7.379 (0.5); 7.320 (16.0); 7.313 (7.8); 7.308 (7.1); 7.294 (6.1); 7.289 (6.2); 6.485 (0.3); 6.482 (0.3); 4.040 (0.5); 4.022 (0.5); 3.913 (2.1); 3.883 (0.6); 3.453 (0.6); 3.435 (0.7); 3.386 (0.9); 3.372 (0.9); 2.676 (0.4); 2.672 (0.4); 2.548 (0.4); 2.511 (48.1); 2.507 (64.2); 2.502 (50.7); 2.338 (0.3); 2.334 (0.4); 2.329 (0.4); 1.992 (2.1); 1.913 (0.7); 1.231 (0.8); 1.195 (0.6); 1.177 (1.1); 1.159 (0.6); 0.008 (3.0); 0.000 (67.1); −0.150 (0.3) |
| II-4 | ¹H-NMR, Solvent [D₆]-DMSO, spectrometer: 399.95 MHz:<br>δ = 8.056(0.3); 8.039(8.3); 8.033(8.6); 7.642(0.3); 7.636(0.4); 7.600(8.8); 7.594(8.8); 7.259(0.6); 7.192(16.0); 5.761(0.7); 3.914(1.7); 3.377(0.3); 3.339(0.5); 3.173(0.5); 2.530(0.5); 2.526(0.8); 2.517(12.0); 2.512(25.0); 2.508(33.6); 2.503(25.3); 2.499(12.9); 2.090(0.6); 1.992(0.6); 1.228(0.6); 1.178(0.4); 0.008(1.0); 0.000(30.9); −0.009(1.3) |
| II-5 | ¹H-NMR, Solvent [D₆]-DMSO, spectrometer: 399.95 MHz:<br>δ = 13.246(0.7); 9.436(8.9); 8.009(6.9); 7.985(7.4); 7.542(6.6); 7.539(6.4); 7.519(5.9); 7.516(5.8); 7.223(16.0); 6.631(1.3); 6.457(0.4); 5.949(0.3); 5.759(0.5); 3.915(1.1); 3.392(0.4); 3.338(4.7); 2.680(0.4); 2.676(0.5); 2.511(60.9); 2.507(77.5); 2.503(58.8); 2.422(1.1); 2.338(0.5); 2.334(0.6); 2.089(0.9); 1.992(0.5); 1.913(1.1); 0.939(0.5); 0.007(2.8); 0.000(51.8) |
| II-6 | ¹H-NMR, Solvent [D₆]-DMSO, spectrometer: 399.95 MHz:<br>δ = 13.290(0.6); 8.146(4.9); 8.124(5.0); 7.716(4.6); 7.698(5.3); 7.465(3.5); 7.443(4.0); 7.425(2.9); 7.394(0.5); 7.318(16.0); 4.040(0.6); 4.022(0.6); 3.918(1.4); 3.340(3.5); 2.512(35.5); 2.508(46.4); 2.503(36.0); 2.334(0.3); 1.992(2.4); 1.913(1.8); 1.195(0.6); 1.177(1.3); 1.160(0.6); 0.008(1.4); 0.000(29.1) |

Biological Examples

*Meloidogyne incognita*—Test
Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined on the basis of the percentage of gall formation. 100% means no galls were found and 0% means the number of galls found on the roots of the treated plants was equal to that in untreated control plants.

In this test, for example, the following compounds from the preparation examples showed good activity of 100% at an application rate of 20 ppm: I-1, I-3, I-9, I-16, I-17, I-18, I-19, I-21, I-22, I-23, I-25, I-26, I-27, I-30, I-33, I-34, I-35, I-36, I-37, I-38, I-39, I-40, I-41, I-42, I-43, I-45, I-57, I-58, I-59, I-60, I-62, I-63, I-64, I-65, I-68, I-69, I-70, I-71, I-72, I-73, I-74, I-75, I-77, I-78

In this test, for example, the following compounds from the preparation examples showed good activity of 90% at an application rate of 20 ppm: I-2, I-3, I-4, I-5, I-8, I-9, I-10, I-12, I-14, I-15, I-20, I-29, I-30, I-32, I-44, I-46, I-49, I-51, I-52, I-66, I-67, I-76

*Meloidogyne incognita*—Test
Solvent: 7 parts by weight of dimethylformamide
Emulsifier: 2.5 parts by weight of alkylarylpolyglycolether To produce a suitable preparation of active compound, 1 part by weight of active compound is mixed with the stated amount of solvent and emulsifier and is diluted with water to the desired concentration. In the calculation of the concentration the soil volume has to be included. Care has to be taken that the emulsifier concentration in the soil does not exceed 20 ppm. Further test concentrations are prepared by dilution with water.

The compound solution is poured into pots filled with soil (loamy sand). A suspension containing eggs and larvae of the southern root-knot nematode (*Meloidogyne incognita*) is added, salad seeds are spread on the soil surface and covered with quartz sand. The salad seeds germinate and the seedlings grow. Galls develop on the roots.

After 21 days the nematicidal activity is determined on the basis of the percentage of gall formation. 100% means no galls were found; 0% means the number of galls found on the roots of the treated plants was equal to that in untreated control plants.

In this test, for example, the following compounds from the preparation examples showed good activity of 80% at an application rate of 8 ppm: 1-47

*Myzus persicae*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 6 days mortality in % is determined. 100% means all aphids have been killed and 0% means none of the aphids have been killed.

In this test, for example, the following compounds from the preparation examples showed good activity of 100% at an application rate of 500 g/ha: I-15

In this test, for example, the following compounds from the preparation examples showed good activity of 90% at an application rate of 500 g/ha: I-46

*Tetranychus Urticae*—Spray Test OP-Resistant
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

French bean (*Phaseolus vulgaris*) leaf disks which are heavily infested with all stages of the two spotted spidermite (*Tetranychus urticae*), are sprayed with a preparation of the active ingredient of the desired concentration.

After 6 days mortality in % is determined. 100% means all spider mites have been killed and 0% means none of the spider mites have been killed.

In this test, for example, the following compounds from the preparation examples showed good activity of 85% at an application rate of 500 g/ha: I-15

The invention claimed is:
1. A compound of formula (I)

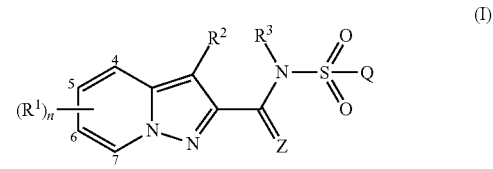

wherein
Z is O or S;
each $R^1$ is independently H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$;

$R^2$ is H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$, $C_2$-$C_6$-alkoxyalkyl, $OC(O)R^{7a}$ and $N(R^{10})C(O)R^{7a}$;

$R^3$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $OR^{4a}$, and $S(O)_m R^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or $C_1$-$C_6$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

Q is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C_4$-$C_8$-cycloalkylalkyl, phenyl, naphthalenyl or a 5- or 6-membered heteroaromatic ring or an 8- to 10-membered heteroaromatic bicyclic ring system, each optionally substituted with 1 to 5 substituents independently selected from the group consisting of halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)2R^9$, $OS(O)2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

or Q is selected from the group consisting of (U-1) to (U-61), (U-81) to (U-87), (U-89) to (U-103) and (U-105) to (U-123):

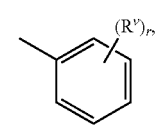

U-1

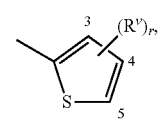

U-2

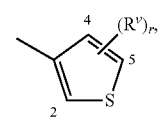

U-3

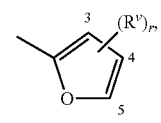

U-4

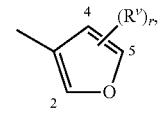

U-5

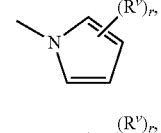

U-6

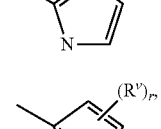

U-7

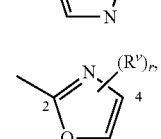

U-8

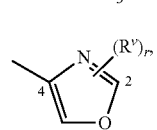

U-9

U-10

-continued
U-11 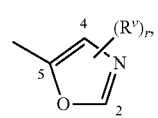
U-12 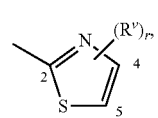
U-13 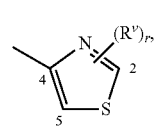
U-14 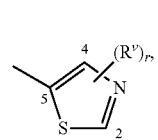
U-15 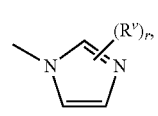
U-16 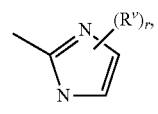
U-17 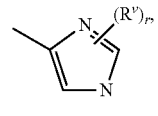
U-18 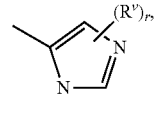
U-19 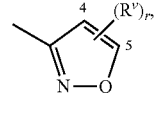
U-20 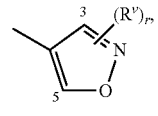
U-21 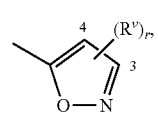
U-22 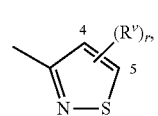
U-23 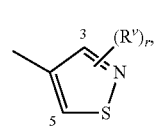
U-24 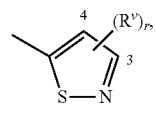
U-25 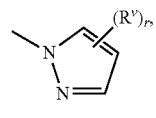
U-26 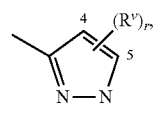
U-27 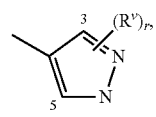
U-28 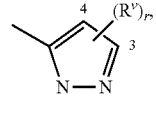
U-29 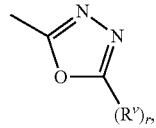
U-30 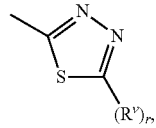
U-31 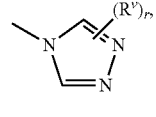
U-32 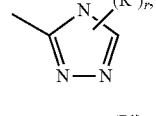
U-33 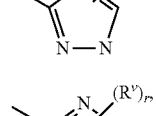
U-34 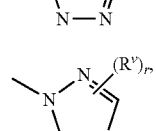
U-35 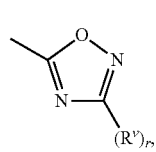
U-36

U-37 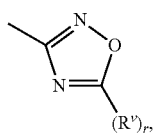
U-38 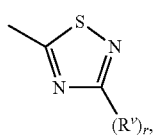
U-39 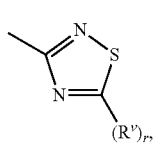
U-40 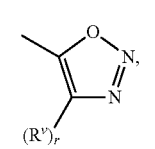
U-41 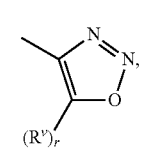
U-42 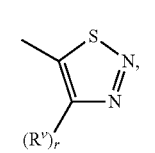
U-43 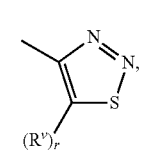
U-44 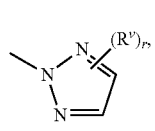
U-45 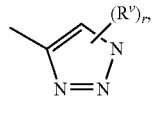
U-46 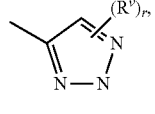
U-47 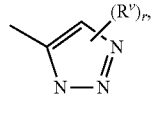
U-48 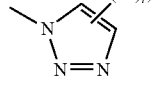
U-49 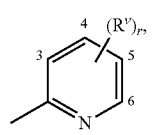
U-50 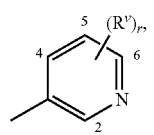
U-51 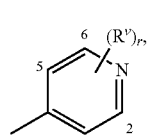
U-52 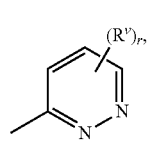
U-53 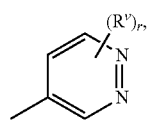
U-54 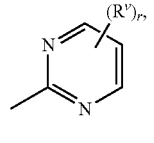
U-55 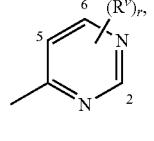
U-56 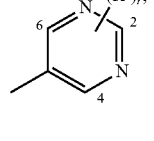
U-57 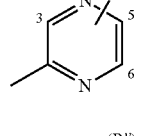
U-58 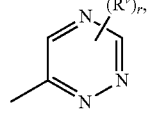
U-59 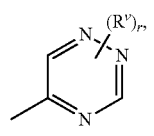

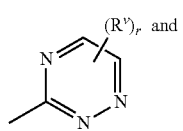  U-60
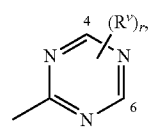  U-61
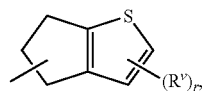  U-81
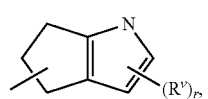  U-82
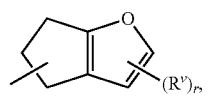  U-83
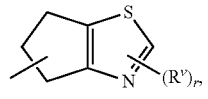  U-84
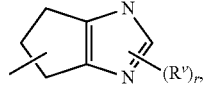  U-85
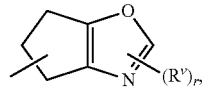  U-86
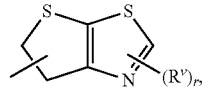  U-87
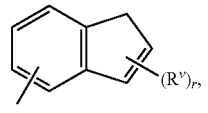  U-89
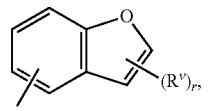  U-90
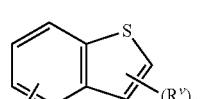  U-91
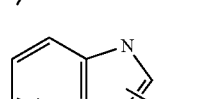  U-92
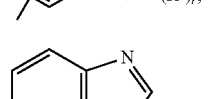  U-93
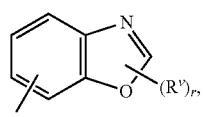  U-94
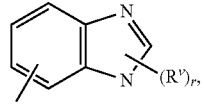  U-95
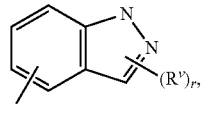  U-96
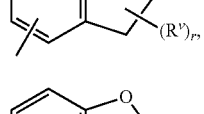  U-97
U-98
U-99
U-100
U-101
U-102
U-103
U-105
U-106
U-107

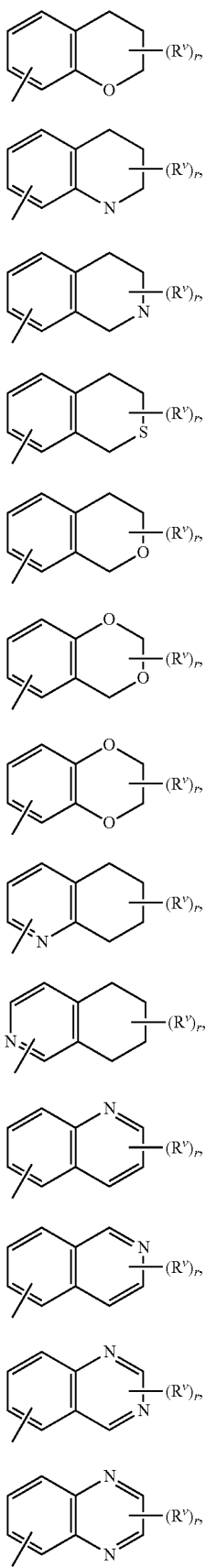

wherein each $R^v$ is independently any substituent as defined for $R^1$, $R^2$ or $R^3$ and r is 0, 1, 2, 3, 4 or 5, limited by the number of available positions on each U group;

each $R^4$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{4a}$ is independently H, $C_1$-$C_6$-alkyl or $C_1$-$C_6$-haloalkyl;

each $R^5$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{5a}$ is independently H or $C_1$-$C_6$-alkyl;

each $R^6$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

each $R^{6a}$ is independently H, $C_1$-$C_6$-alkyl, $C(O)R^{13}$ or $C(O)OR^{13}$;

each $R^7$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{7a}$ is independently $C_1$-$C_6$-alkyl or $C_1$-$C_6$-haloalkyl;

each $R^8$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{8a}$ is independently $C_1$-$C_6$-alkyl or $C_1$-$C_6$-haloalkyl;

each $R^9$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{9a}$ is independently $C_1$-$C_6$-alkyl or $C_1$-$C_6$-haloalkyl;

each $R^{10}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^{7a}$, $C(O)OR^{8a}$, $C(O)NR^{11}R^{12}$, $S(O)_mR^{9a}$ or $S(O)_2NR^{11}R^{12}$;

each $R^{11}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11a}R^{12}$, $S(O)_mR^{9a}$ and $S(O)_2NR^{11a}R^{12}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11a}R^{12}$, $OR^{4a}$, $C_2$-$C_6$-alkoxyalkyl, $S(O)_mR^{9a}$, $S(O)_2NR^{11a}R^{12}$, $NR^{5a}R^{6a}$, $OC(O)R^{7a}$ and $N(R^{10})C(O)R^{7a}$;

each $R^{11a}$ is independently H, $C_1$-$C_6$-alkyl, $C_2$-$C_6$-alkenyl or $C_2$-$C_6$-alkynyl;

each $R^{12}$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{13}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

each $R^{14}$ is independently $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$; or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$; or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

each $R^{15}$ is independently $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_m R^{9a}$; or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

X is O or S;

each m is independently 0, 1 or 2; and n is 0, 1, 2, 3 or 4.

2. A compound according to claim 1, wherein each $R^1$ is independently halogen, cyano, $OR^4$, $C_1$-$C_4$-alkyl, $C_1$-$C_4$-haloalkyl; or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

$R^2$ is H, halogen, cyano, $S(O)_mR^9$ or $S(O)_2NR^{11}R^{12}$; or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl; or $C_1$-$C_4$-alkyl substituted with 1 to 2 substituents independently selected from the group consisting of cyano, $OR^4$ and $S(O)_mR^9$;

$R^3$ is H, $C_1$-$C_4$-alkyl, $C_2$-$C_3$-alkenyl, $C(X)R^7$ or $C(O)OR^8$; or $C_1$-$C_2$-alkyl substituted with $OR^4$; or $C_1$-$C_2$-alkyl substituted with phenyl;

Q is $C_1$-$C_6$-alkyl, $C_1$-$C_6$-haloalkyl, $C_3$-$C_7$-cycloalkyl, phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$ and $S(O)_2NR^{11}R^{12}$;

or Q is selected from the group consisting of (U-1) to (U-61), (U-81) to (U-87), (U-89) to (U-103) and (U-105) to (U-123);

each $R^v$ is independently halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$;

r is 0, 1, 2 or 3, limited by the number of available positions on each U group;

each $R^4$ is independently H, $C_1$-$C_4$-alkyl or $C_1$-$C_4$-haloalkyl;

each $R^7$ is independently H, $C_1$-$C_4$-alkyl or $C_1$-$C_4$-haloalkyl; or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl;

each $R^8$ is independently $C_1$-$C_2$-alkyl or $C_1$-$C_2$-haloalkyl;

each $R^9$ is independently $C_1$-$C_2$-alkyl or $C_1$-$C_2$-haloalkyl;

each $R^{11}$ is independently H, $C_1$-$C_4$-alkyl, $C_1$-$C_4$-haloalkyl;

each $R^{12}$ is independently H, $C_1$-$C_4$-alkyl or $C_1$-$C_4$-haloalkyl;

X is O;

Z is O;

m is 0, 1 or 2; and n is 1, 2 or 3.

3. A compound according to claim 1, wherein each $R^1$ is independently chlorine or trifluoromethyl;

$R^2$ is hydrogen;

$R^3$ is hydrogen;

Q is methyl, ethyl or cyclopropyl or is selected from the group consisting of (U-1), (U-49) and (U-103);

each $R^v$ is independently fluor, chlor, methoxy, trifluoromethyl, trifluoromethoxy or methyl;

r is 1, 2 or 3, limited by the number of available positions on each U group;

each $R^4$ is independently methyl, ethyl, propyl, isopropyl, difluoromethyl or trifluoromethyl;

Z is O; and n is 1 or 2.

4. A compound according to claim 1 which is represented by formula (Ia):

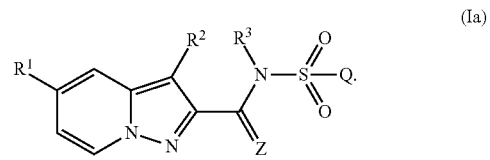

(Ia)

5. A compound according to claim 4 which is represented by formula (Ia-1):

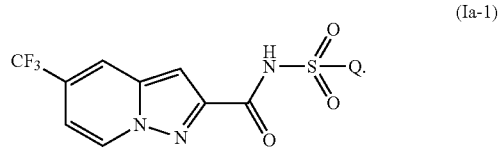

(Ia-1)

6. A compound according to claim 1 which is represented by formula (Ib):

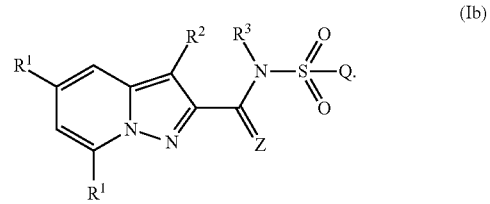

(Ib)

7. A compound according to claim 6 which is represented by formula (Ib-1):

8. A compound according to claim 6 which is represented by formula (Ib-2):

(Ib-2)

9. A compound according to claim 1 which is represented by formula (Ic):

(Ic)

10. A compound according to claim 1 which is represented by formula (Id):

(Id)

11. A compound according to claim 10 which is represented by formula (Id-1):

(Id-1)

12. A compound according to claim 1 which is represented by formula (Ie):

(Ie)

13. A compound according to claim 12 which is represented by formula (Ie-1):

(Ie-1)

14. A compound according to claim 1 which is represented by formula (If):

(If)

15. A compound according to claim 14 which is represented by formula (If-1):

(If-1)

16. A formulation comprising at least one compound of formula (I) according to claim 1.

17. A formulation according to claim 16 which further comprises at least one extender and/or at least one surfactant.

18. A formulation according to claim 16, wherein the compound of the formula (I) is present in a mixture with at least one other active compound.

19. A method for controlling an animal pest selected from the group consisting of insects, arachnids, helminths, nematodes, and molluscs, comprising applying an effective amount of a compound of formula (I) according to claim 1 or a formulation thereof to the animal pest and/or a habitat thereof.

20. A method according to claim 19, wherein the animal pest comprises a nematode or is a nematode.

21. A method according to claim 19, wherein said controlling of said animal pest is in crop protection.

22. A method according to claim 19, wherein said controlling of said animal pest is in the animal health field.

23. A method for protecting a seed and/or a geminating plant from attack by a pest, wherein the pest is selected from the group consisting of insects, arachnids, helminths, nematodes, and molluscs, comprising contacting the seed with a compound of formula (I) according to claim 1 or with a formulation thereof.

24. A seed obtained by a method according to claim 23.

25. A method according to claim 23 wherein the pest is a nematode.

\* \* \* \* \*